United States Patent [19]

Gosteli et al.

[11] 4,447,360
[45] May 8, 1984

[54] INTERMEDIATES FOR THIA-AZA COMPOUNDS WITH A β-LACTAM RING

[75] Inventors: Jacques Gosteli, Basel; Ivan Ernest, Birsfelden, both of Switzerland; Robert B. Woodward, Cambridge, Mass.

[73] Assignee: Ciba-Geigy Corporation, Ardsley, N.Y.

[21] Appl. No.: 214,316

[22] Filed: Dec. 8, 1980

Related U.S. Application Data

[62] Division of Ser. No. 902,639, May 4, 1978, Pat. No. 4,331,676.

[30] Foreign Application Priority Data

May 9, 1977 [LU] Luxembourg .............................. 77306

[51] Int. Cl.$^3$ ................. C07D 205/08; C07D 401/12; C07D 405/12; C07D 409/12
[52] U.S. Cl. ............................. 260/239 A; 260/245.4; 260/330.3; 260/330.9; 546/208; 546/275
[58] Field of Search ............. 260/239 A, 245.4, 330.3, 260/330.9; 546/208, 275

[56] References Cited

U.S. PATENT DOCUMENTS

| | | | |
|---|---|---|---|
| 4,169,833 | 10/1979 | Menard | 260/239 A |
| 4,192,801 | 3/1980 | Ueda | 260/239 A |
| 4,272,437 | 6/1981 | Menard | 260/239 A |
| 4,282,150 | 8/1981 | Menard et al. | 260/239 A |

*Primary Examiner*—Mark L. Berch
*Attorney, Agent, or Firm*—Michael W. Glynn; Prabodh I. Almaula

[57] ABSTRACT

2-Penem-3-carboxylic acid compounds of the formula

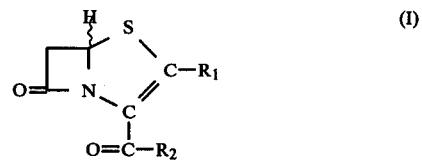

in which
  $R_1$ represents hydrogen, an organic radical bonded by a carbon atom to the ring carbon atom or an etherified mercapto group and
  $R_2$ represents hydroxy or a radical $R_2^A$ forming together with the carbonyl grouping —C(=O)— a protected carboxyl group, 1-oxides thereof, as well as salts of such compounds having salt-forming groups, in racemic and optically active form, processes for their preparation, pharmaceutical compositions containing such compounds, and their use as antibiotics, and intermediates and their processes which are useful in the production of the compounds of the formula I.

3 Claims, No Drawings

INTERMEDIATES FOR THIA-AZA COMPOUNDS WITH A β-LACTAM RING

This is a divisional of application Ser. No. 902,639 filed on May 4, 1978, U.S. Pat. No. 4,331,676.

The present invention relates to new bicyclic thia-aza compounds containing a β-lactam ring unsubstituted in the 3-position and having antibiotic properties.

Since the discovery of penicillin, numerous bicyclic thia-aza compounds having a β-lactam structure have become known. A survey of earlier works reveals E. H. Flynn, "Cephalosporins and Penicillins", Academic Press, New York and London, 1972. Very recent developments are described by J. Cs. Jaszberenyi et al., Progr. Med. Chem., Vol. 12, 1975, 395–477, and P. G. Sammas, Chem. Rev. 1976, Vol. 76, No. 1, 113–155. At the symposium "Recent Advances in the Chemistry of β-lactam Antibiotics" from 28th to 30th June, 1976, held in Cambridge, England, 6-acylamino-2-penem-3-carboxylic acid compounds having an antibiotic action and containing the novel 2-penem ring system were described by R. B. Woodward.

Apart from the usual penam and cephem compounds carrying an acylamino group in the 6- or 7-position, such compounds that are unsubstituted in these positions have also become known, for example 3-carboxy-2,2-dimethylpenam (J. P. Clayton, J. Chem. Soc., 1969, 2123) and 3-methyl-4-carboxy-3-cephem (K. Kühlein, Liebigs Ann., 1974, page 369 and D. Bormann, ibid., page 1391). None of these compounds, however, has any substantial antibiotic activity. 2-penem compounds that are unsubstituted in the 6-position are so far unknown.

The problem underlying the present invention is to produce bicyclic thia-aza compounds containing a β-lactam ring that possess the 2-penem ring system unsubstituted in the 6-position and that are active against normal and against resistant bacteria.

The manufacture according to the invention of the novel compounds and the new intermediate products required therefor open up new fields in which research into other commercially valuable compounds can be carried out.

The ring system of the compounds of the present invention has the formula

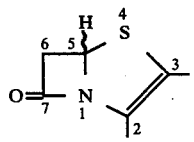

and may systematically be called 7-oxo-4-thia-1-azabicyclo[3,2,0]hept-2-ene. For the sake of simplicity it is referred to hereinafter as "2-penem", wherein the following numbering derived from penam and customary in penicillin chemistry shall be used:

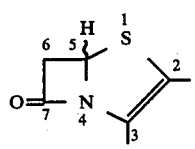

The 2-penem ring system has an asymmetrically substituted carbon atom in the 5-position, so that corresponding compounds, according to the Cahn-Ingold-Prelog designation, may occur in the (5R)-, (5S)- or the racemic (5R,S)-configuration.

The subject of the present invention is 2-penem-3-carboxylic acid compounds of the formula

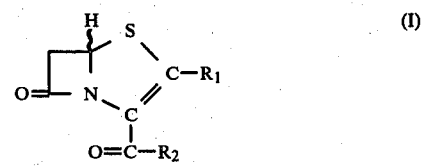

in which
$R_1$ represents hydrogen, an organic radical bonded by a carbon atom to the ring carbon atom, or an etherified mercapto group, and
$R_2$ represents hydroxy or a radical $R_2^A$ forming together with the carbonyl grouping —C(=O)— a protected carboxyl group, 1-oxides thereof, as well as salts of such compounds having salt-forming groups, processes for the manufacture of such compounds, also pharmaceutical preparations containing compounds of the formula I having pharmacological properties, and the use of the new compounds either as pharmacologically active substances, preferably in the form of pharmaceutical preparations, or as intermediate products.

An organic radical $R_1$ bonded by a carbon atom to the ring carbon atom is primarily an optionally substituted aliphatic, cycloaliphatic, cycloaliphatic-aliphatic, aromatic or araliphatic hydrocarbon radical having up to 18, preferably up to 10, carbon atoms, especially optionally substituted lower alkyl, optionally functionally modified carboxyl, cycloalkyl, cycloalkyl-lower alkyl, phenyl, naphthyl or phenyl-lower alkyl. Examples of substituents of such radicals are optionally functionally modified, such as optionally etherified or esterified, hydroxy or mercapto groups, for example hydroxy, lower alkoxy, for example methoxy or ethoxy, lower alkanoyloxy, for example acetoxy or propionyloxy, halogen, for example chlorine or bromine, or lower alkylthio, for example methylthio or tert.-butylthio, or optionally functionally modified carboxyl groups, such as carboxyl, lower alkoxycarbonyl, for example methoxycarbonyl or ethoxycarbonyl, carbamoyl or cyano; also nitro; or amino optionally mono- or di-substituted, such as by lower alkyl, for example methyl or ethyl, or optionally disubstituted by lower alkylene, for example 1,4-butylene or 1,5-pentylene, or protected, such as acylated.

A lower alkyl radical $R_1$ contains, for example, up to 7, especially up to 4, carbon atoms, and is, inter alia, methyl, ethyl, propyl, isopropyl, butyl, isobutyl, tert.-butyl or pentyl. Substituted lower alkyl is, primarily, substituted methyl, or ethyl or propyl that are substituted in the 1- or especially in the ω-position, such as hydroxymethyl or hydroxyethyl; lower alkoxymethyl or lower alkoxyethyl, for example methoxymethyl or methoxyethyl; lower alkanoyloxymethyl or lower alkanoyloxyethyl, for example acetoxymethyl, propionyloxymethyl or acetoxyethyl; halomethyl or haloethyl, for example chloromethyl or bromomethyl or chloroethyl or bromoethyl; lower alkylthiomethyl or lower alkylthioethyl, such as methylthiomethyl, tert.-butylthiomethyl, methylthioethyl or methylthiopropyl; lower alkoxycarbonylmethyl or lower alkoxycarbonylethyl, for example methoxycarbonylmethyl, ethoxycarbonylmethyl or methoxycarbonylethyl; cyanomethyl or cyanoethyl; or aminomethyl, aminoethyl or aminopropyl that are optionally protected, for example by a semi-ester of carbonic acid, such as by tert.-butoxycarbonyl, benzyloxycarbonyl or p-nitrobenzyloxycarbonyl, or acylated, such as by optionally substituted acetyl, for example phenoxyacetyl.

An optionally functionally modified carboxyl group $R_1$ is a free carboxyl group or one of the for example esterified or amidated carboxyl groups mentioned under the groups —C(=O)—$R_2^A$, such as lower alkoxycarbonyl, for example methoxy-, ethoxy- or tert.-butoxycarbonyl; aryl-lower alkoxycarbonyl, such as benzyloxy-, p-nitrobenzyloxy- or diphenylmethoxycarbonyl; aryloxycarbonyl, such as phenoxycarbonyl optionally substituted for example by halogen, such as chlorine, by lower alkoxy, such as methoxy, or by nitro, such as phenoxycarbonyl, o-, m- or p-chlorophenoxycarbonyl, pentachlorophenoxycarbonyl, o-, m- or p-methoxyphenoxycarbonyl or p-nitrophenoxycarbonyl; aminocarbonyl or aminocarbonyl mono- or disubstituted by, for example, lower alkyl, for example methyl or ethyl.

A cycloalkyl radical $R_1$ has, for example, 3 to 7 carbon atoms and is, for example, cyclopropyl, cyclobutyl, cyclopentyl or cyclohexyl, whereas a cycloalkyl-lower alkyl radical $R_1$ contains, for example, 4 to 7 carbon atoms and is, for example, cyclopropylmethyl, cyclobutylmethyl, cyclopentylmethyl or cyclohexylmethyl.

A phenyl or naphthyl radical $R_1$, for example a 1- or 2-naphthyl radical, or a phenyl-lower alkyl radical $R_1$, for example a benzyl or 1- or 2-phenylethyl radical, may be substituted preferably in the aromatic radical, for example by lower alkyl such as methyl or ethyl, by lower alkoxy, such as methoxy, or by halogen, such as fluorine or chlorine, further by nitro, amino or substituted amino, such as di-lower alkyl-amino, for example dimethylamino.

The radical $R_1$ may alternatively be a heterocyclic or heterocyclic-aliphatic radical, preferably of aromatic character, bonded by a carbon atom, for example such a radical having 5 or 6 ring members and nitrogen, oxygen or sulphur as hetero atoms, such as pyridyl, for example 2-, 3- or 4-pyridyl, thienyl, for example 2-thienyl, or furyl, for example 2-furyl, or a corresponding pyridyl-, thienyl- or furyl-lower alkyl, especially -methyl, radical.

An etherified mercapto group $R_1$ is etherified by an optionally substituted aliphatic, cycloaliphatic, cycloaliphatic-aliphatic, aromatic or araliphatic hydrocarbon radical having up to 18, preferably up to 10, carbon atoms, and is especially optionally substituted lower alkylthio, lower alkenylthio, cycloalkylthio, cycloalkyl-lower alkylthio, phenylthio or phenyl-lower alkylthio. Substituents of such radicals are, for example, optionally functionally modified, such as optionally etherified or esterified, hydroxy or mercapto, for example hydroxy, lower alkoxy, for example methoxy or ethoxy, lower alkanoyloxy, for example acetoxy or propionyloxy, halogen, for example chlorine or bromine, or lower alkylthio, for example methylthio; or optionally functionally modified carboxyl groups, such as carboxyl, lower alkoxycarbonyl, for example methoxycarbonyl or ethoxycarbonyl, carbamoyl or cyano; also nitro; or amino optionally mono- or di-substituted such as by lower alkyl, for example methyl or ethyl, or by acyl, such as lower alkanoyl, for example acetyl; or amino optionally di-substituted by lower alkylene, for example by 1,4-butylene or 1,5-pentylene.

A lower alkylthio radical $R_1$ contains up to 7, especially up to 4, carbon atoms, and is, for example, methylthio, ethylthio, propylthio, isopropylthio, butylthio, isobutylthio, tert.-butylthio or pentylthio. Substituted lower alkylthio $R_1$ is, primarily, substituted methylthio, ethylthio or propylthio, the substituents standing in the 1-, 2- or 3-position, such as methoxymethylthio, ethoxymethylthio, methoxyethylthio or methoxypropylthio; lower alkanoyloxymethylthio, lower alkanoyloxyethylthio or lower alkanoyloxypropylthio, such as acetoxymethylthio, acetoxyethylthio or acetoxypropylthio; halomethylthio, haloethylthio or halopropylthio, for example chloroethylthio or bromoethylthio, or chloropropylthio or bromopropylthio; lower alkoxycarbonylmethylthio or lower alkoxycarbonylethylthio, for example methoxycarbonylethylthio; cyanomethylthio; cyanoethylthio; or optionally protected, for example acetylated, aminomethylthio, aminoethylthio or aminopropylthio.

A lower alkenylthio radical $R_1$ contains 2 to 7, especially 2 to 4, carbon atoms and is especially 1-lower alkenylthio, for example, vinylthio, 1-propenylthio, 1-butenylthio or 1-pentenylthio or also 2-lower alkenylthio, for example allylthio. Substituted lower alkenylthio $R_1$ is, primarily, substituted in the 2-position, wherein the substituents that chiefly come into consideration are lower alkoxy, lower alkanoyloxy and optionally protected amino. Thus $R_1$ is, for example, 2-methoxyvinylthio, 2-acetoxyvinylthio, 2-acetylaminovinylthio or correspondingly substituted 1-propenylthio.

A cycloalkylthio group $R_1$ has, for example, 3 to 7 carbons atoms, and is, for example, cyclopropylthio, cyclobutylthio, cyclopentylthio or cyclohexylthio.

A cycloalkyl-lower alkylthio radical $R_1$ has, for example, 4 to 7 carbon atoms and is, for example, cyclopropylmethylthio, cyclobutylmethylthio, cyclopentylmethylthio or cyclohexylmethylthio.

A phenylthio radical $R_1$ or a phenyl-lower alkylthio radical $R_1$, for example benzyl- or 1- or 2-phenylethylthio radical, may be substituted, preferably in the aromatic radical, for example by lower alkyl, such as methyl or ethyl, by lower alkoxy, such as methoxy, by halogen, such as fluorine or chlorine, or by nitro or amino.

A protected carboxyl group of the formula —C(=O)—$R_2^A$ is primarily an esterified carboxyl group in which $R_2^A$ represents a hydroxy group etherified by an organic radical or an organic silyl or stannyl group. Organic radicals, also as substituents in organic silyl or stannyl groups, are aliphatic, cycloaliphatic, cycloaliphatic-aliphatic, aromatic or araliphatic radicals, especially optionally substituted hydrocarbon radicals of this type, and heterocyclic or heterocyclic-aliphatic radicals, preferably having up to 18 carbon atoms.

An etherified hydroxy group $R_2^A$ forms together with the carbonyl grouping an esterified carboxyl group that can preferably be readily split, for example by reduction, such as by hydrogenolysis, or by solvolysis, such as acid hydrolysis or, especially, basic or neutral hydrolysis, oxidatively, or under physiological conditions, or an esterified carboxyl group that is readily convertible into another functionally modified carboxyl group, such as into another esterified carboxyl group or into a hydrozinocarbonyl group. Such a group $R_2^A$ is, for example, 2-halo-lower alkoxy, in which the halogen preferably has an atomic weight of more than 19, for example 2,2,2-trichloroethoxy or 2-iodoethoxy, also 2-chloroethoxy or 2-bromoethoxy which may readily be converted into the latter, or 2-lower alkylsulphonyl-lower alkoxy, for example, 2-methylsulphonylethoxy. The group $A_2^4$ is furthermore a methoxy group polysubstituted by optionally substituted hydrocarbon radicals, especially saturated aliphatic or aromatic hydrocarbon radicals, such as lower alkyl, for example methyl, and/or phenyl, or is a methoxy group monosubstituted by an unsaturated aliphatic hydrocarbon radical, such as lower alkenyl, for example 1-lower alkenyl, such as vinyl, by a carbocyclic aryl group having electron-donating substituents, or by a heterocyclic group of aromatic character having oxygen or sulphur as ring member. Examples of such groups $R_2^4$ are tert.-lower alkoxy, for example tert.-butoxy or tert.-pentoxy; optionally substituted diphenylmethoxy, for example diphenylmethoxy or 4,4'-dimethoxydiphenylmethoxy; lower alkenyloxy, especially 2-lower alkenyloxy, for example allyloxy; lower alkoxyphenyl-lower alkoxy, for example lower alkoxybenzyloxy, such as methoxybenzyloxy (in which methoxy is, primarily, in the 3-, 4- and/or 5-position), primarily 3- or 4-methoxybenzyloxy or 3,4-dimethoxybenzyloxy; or, above all, nitrobenzyloxy, for example, 4-nitrobenzyloxy, 2-nitrobenzyloxy or 4,5-dimethoxy-2-nitrobenzyloxy; or furfuryloxy, such as 2-furfuryloxy. The group $R_2^4$ is furthermore a 2-oxoethoxy group that is optionally substituted in the 2-position by lower alkyl, such as methyl, by lower alkoxy, such as methoxy or ethoxy, by aralkyl, such as benzyl, or by aryl, such as phenyl, and is optionally substituted in the 1-position by lower alkyl, such as methyl, lower alkoxycarbonyl, such as methoxycarbonyl, lower alkylcarbonyl, such as methylcarbonyl, aralkylcarbonyl, such as benzylcarbonyl, or arylcarbonyl, such as benzoyl. Thus $R_2^4$ represents, for example, acetonyloxy, phenacyloxy, 2,4-dioxo-3-pentoxy, 1-methoxycarbonyl-2-oxopropoxy or 1-ethoxycarbonyl-2-oxopropoxy. The group $R_2^4$ is alternatively a 2-cyanoethoxy group that is optionally substituted in the 1- and/or in the 2-position, for example by lower alkyl, such as methyl, or by aryl, such as optionally substituted phenyl, and represents, for example, 2-cyanoethoxy or 2-cyano-2-cyano-2-phenylethoxy. $R_2^4$ is alternatively a 2-$(S_1)(S_2)(S_3)$-silylethoxy group, in which each of the substituents $S_1$, $S_2$ and $S_3$ independently of one another represents an optionally substituted hydrocarbon radical and the individual radicals may be linked by a single C—C bond. A hydrocarbon radical $S_1$, $S_2$, $S_3$ is, for example, an alkyl radical, a cycloalkyl radical or an aryl radical, preferably such a radical having a maximum of 12 carbon atoms, wherein the radical of one kind may be substituted by a radical of a different kind, or by lower alkoxy, such as methoxy, or by halogen, such as fluorine or chlorine; and is especially lower alkyl having up to 7, preferably up to 4, carbon atoms, such as methyl, ethyl, propyl or butyl; cycloalkyl having up to 7 carbon atoms, such as cyclopropyl or cyclohexyl; cycloalkylalkyl, such as cyclopentylmethyl; aryl having up to 10 carbon atoms, such as phenyl, tolyl or xylyl; or aryl-lower alkyl, such as benzyl or phenylethyl. Radicals $R_2^4$ of this kind to be singled out are 2-tri-lower alkylsilylethoxy, such as 2-trimethylsilylethoxy or 2-(dibutylmethylsilyl)-ethoxy, and 2-triarylsilylethoxy, such as 2-triphenylsilylethoxy.

$R_2^4$ may alternatively be 2-oxa- or 2-thia-cycloalkoxy or -cycloalkenyloxy having 5–7 ring members, such as 2-tetrahydrofuryloxy, 2-tetrahydropyranyloxy or 2,3-dihydro-2-pyranyloxy or a corresponding thia group, or $R_2^4$ forms together with the —C(=O)— grouping an activated ester group and is, for example, nitrophenoxy, for example 4-nitrophenoxy or 2,4-dinitrophenoxy, or polyhalophenoxy, for example pentachlorophenoxy. $R_2^4$ may, however, alternatively be an unbranched lower alkoxy, for example methoxy or ethoxy.

An organic silyloxy or organic stannyloxy group $R_2^4$ is especially a silyloxy or stannyloxy group substituted by 1 to 3 optionally substituted hydrocarbon radicals, preferably having up to 18 carbon atoms. It contains as substituents preferably optionally substituted, for example by lower alkoxy, such as methoxy, or by halogen, such as chlorine, aliphatic, cycloaliphatic, aromatic or araliphatic hydrocarbon radicals, such as lower alkyl, halogen-lower alkyl, cycloalkyl, phenyl or phenyl-lower alkyl and represents primarily tri-lower alkylsilyloxy, for example, trimethylsilyloxy, halo-lower alkoxy-lower alkylsilyloxy, for example, chloromethoxymethylsilyloxy, or tri-lower alkylstannyloxy, for example tri-n-butylstannyloxy.

The group $R_2^4$ may alternatively be an etherified hydroxy group that together with the carbonyl grouping —C(=O)— forms an esterified carboxyl group that can be split under physiological conditions, primarily an acyloxymethoxy group, in which acyl represents, for example, the radical of an organic carboxylic acid, primarily an optionally substituted lower alkanecarboxylic acid, or in which acyloxymethyl forms the radical of a lactone. Hydroxy groups etherified in this manner are lower alkanoyloxymethoxy, for example acetoxymethoxy or pivaloyloxymethoxy; amino-lower alkanoyloxymethoxy, especially α-amino-lower alkanoyloxymethyl, for example glycyloxymethoxy, L-valyloxymethoxy, L-leucyloxymethoxy, and also phthalidyloxy. In other ester groups —C(=O)—$R_2^4$ that can be physiologically split, $R_2^4$ is a 2-aminoethoxy group, in which amino is substituted by two lower alkyl groups or by alkylene optionally containing an oxa group, and represents, for example 2-dimethylaminoethoxy, 2diethylaminoethoxy or 2-(1-morpholino)-ethoxy.

A radical $R_2^4$ forming with a —C(=O)-grouping an optionally substituted hydrazinocarbonyl group is, for example, hydrazino or 2-lower alkylhydrazino, for example 2-methylhydrazino.

Preferred groups $R_2^4$ are those that can be converted into a free hydroxy group under neutral, basic or physiological conditions.

Salts are especially those of compounds of the formula I with an acid grouping such as a carboxyl group, primarily metal or ammonium salts, such as alkali metal and alkaline earth metal salts, for example sodium, potassium, magnesium or calcium salts; as well as ammonium salts with ammonia or suitable organic amines, primarily aliphatic, cycloaliphatic, cycloaliphatic-aliphatic or araliphatic primary, secondary or tertiary mono-, di- or polyamines, or heterocyclic bases, such as lower alkylamines, for example triethylamine; hydroxy-lower alkylamines, for example 2-hydroxyethylamine, di-(2-hydroxyethyl)-amine or tri-(2-hydroxyethyl)-amine; basic aliphatic esters of carboxylic acids, for example 4-aminobenzoic acid 2-diethylaminoethyl ester; lower alkyleneamines, for example 1-ethylpiperidine; cycloalkylamines, for example bicyclohexylamine;

or benzylamines, for example N,N'-dibenzylethylenediamine; and also, bases of the pyridine type, for example pyridine, collidine or quinoline. Compounds of the formula I that have a basic group may likewise form acid addition salts, for example with inorganic acids, such as hydrochloric acid, sulphuric acid or phosphoric acid, or with suitable organic carboxylic or sulphonic acids, for example trifluoroacetic acid or p-toluenesulphonic acid. Compounds of the formula I having an acid and a basic group may also occur in the form of inner salts, that is in the zwitterion form. 1-oxides of compounds of the formula I having slat-forming groups may likewise form salts as described above. Salts that can be used pharmaceutically are preferred.

The penem compounds of the formula I may, on account of the asymmetric carbon atom in the 5-position, occur in the (5R)-, (5S)- or (5 R,S)-configuration. The (5R)-compounds are preferred.

The compounds of the present invention have valuable pharmacological properties or may be used as intermediate products for the manufacture of compounds having such properties. Compounds of the formula I, in which $R_1$ has the meaning given above and $R_2$ represents hydroxy or an etherified hydroxy group, $R_2^A$ forming together with the carbonyl group an esterified carboxyl group that can be readily split preferably under physiological conditions, or pharmacologically usable salts of such compounds having salt-forming groups, inhibit, for example, the growth of gram-positive and gram-negative bacteria, such as *Staphylococcus aureus* and penicillin-resistant *Staphylococcus aureus*, *Escherichia coli*, *Proteus vulgaris*, *Pseudomonas aeruginosa* and *Pseudomonas aeruginosa R*.

Using the compounds of the formula I according to the invention in the disc-plate test with the specified bacteria with a 0.5% strength solution on filter paper (6 mm diameter) inhibiting zones of approximately 16 to 33 mm diameter are found, whereas Penicillin V tested analogously at the same time, in the case of normal *Staphylococcus aureus* bacteria causes inhibiting zones of 31 to 32 mm diameter and in the case of resistant bacteria inhibiting zones of only 10 to 11 mm.

The compounds of the formula I according to the invention are effective in vitro in the following dosage ranges: against cocci (inclusive of penicillinase-formers), from <0.1 to 64 mcg/ml; against entero bacteria (inclusive of β-lactamase-formers), from 0.5 to 128 mcg/ml; and against *Pseudomonas aeruginosa*, from 2 to 128 mcg/ml. In vivo (mouse) they are effective with subcutaneous administration against streptococcus in a dosage range of from 8 to 50 mg/kg.

Attention is drawn in particular to the activity against *Pseudomonas aeruginosa*, against which neither Penicillin V nor Penicillin G is effective.

The compounds inhibit β-lactamase and have a synergistic effect in combination with other β-lactam antibiotics.

These new compounds, especially the preferred ones, or their pharmacologically usable salts, may therefore be used, for example, in the form of antibiotically-active preparations, in the treatment of human or animal bodies for corresponding systemic or organ infections, as fodder additives, for preserving foodstuffs or as disinfectants.

1-oxides of compounds of the formula I, in which $R_1$ and $R_3$ have the meaning given in connection with formula I, or compounds of the formula I in which $R_1$ has the meaning given above and $R_2$ represents a radical $R_2^A$ forming together with the —C(=O)— grouping a protected carboxyl group that can preferably be readily split, wherein a carboxyl group protected in this manner is different from a carboxyl group that can be split physiologically, are valuable intermediate products that can be converted in a simple manner, for example as described below, into the above-mentioned, pharmacologically active compounds.

The invention relates especially to the 2-penem compounds of the formula I, in which $R_1$ represents hydrogen; a lower alkyl optionally substituted by etherified or esterified hydroxy or mercapto, such as lower alkoxy, lower alkanoyloxy or lower alkylthio, by functionally modified carboxyl, such as lower alkoxycarbonyl, or by optionally substituted, for example acylated, amino; or represents phenyl-lower alkyl or phenyl optionally substituted by lower alkyl, lower alkoxy, halogen, nitro, amino or di-lower alkylamino; an aromatic heterocyclic radical, or an etherified mercapto group, such as lower alkylthio; and $R_2$ represents hydroxy; a hydroxy group etherified by an organic radical or an organic silyl or stannyl group, that can be split under basic or neutral conditions or physiologically; or represents an optionally substituted hydrazino group $R_2^A$, and relates to salts of such compounds with salt-forming groups.

In a 2-penem compound of the formula I or in a salt of such a compound having salt-forming groups, $R_1$ primarily represents hydrogen; lower alkyl having up to 7 carbon atoms, for example methyl, isopropyl or pentyl; lower alkoxy-lower alkyl, in which lower alkyl in each case contains up to 4 carbon atoms, for example methoxymethyl; lower alkanoyloxy-lower alkyl, in which lower alkyl in each case contains up to 4 carbon atoms, for example acetoxymethyl; lower alkylthio-lower alkyl, in which lower alkyl in each case contains up to 4 carbon atoms, for example methylthiomethyl or tert.-butylthiomethyl; lower alkoxycarbonyl-lower alkyl, in which lower alkyl in each case contains up to 4 carbon atoms, such as lower alkoxycarbonylmethyl or lower alkoxycarbonylethyl, for example methoxycarbonylethyl; amino-lower alkyl, in which lower alkyl contains up to 4 carbon atoms and in which the amino group is optionally acylated by a semi-ester of carbonic acid or by a substituted acetyl group, for example aminomethyl, aminoethyl or aminopropyl, or the corresponding aminomethyl, aminoethyl or aminopropyl N-acylated by benzyloxycarbonyl, p-nitrobenzyloxycarbonyl or phenoxyacetyl; or phenyl optionally substituted by lower alkyl, halogen, nitro, amino or di-lower alkylamino, for example phenyl or dimethylaminophenyl; phenyl-lower alkyl, for example benzyl; an aromatic heterocyclyl radical containing 5 or 6 ring members with a nitrogen, an oxygen or a sulphur atom as hetero atom, for example pyridyl, furyl or thienyl; or lower alkylthio, for example ethylthio; and $R_2$ primarily represents hydroxy, or an etherified hydroxy group that can be split under basic or neutral conditions or physiologically, such as optionally α-polybranched lower alkoxy, for example tert.-butyloxy, 2-substituted 2-oxoethoxy, for example acetonyloxy, or phenacyloxy, 2-cyanoethoxy, 2-$(S_1)(S_2)(S_3)$-silylethoxy, in which each of $S_1$, $S_2$ and $S_3$ represents lower alkyl, such as methyl, or phenyl, such as 2-trimethylsilylethoxy or 2-triphenylsilylethoxy, 1-phenyl-lower alkoxy having 1–3 phenyl radicals optionally substituted by lower alkoxy and/or nitro, for example 4-methoxybenzyloxy, 4-nitrobenzyloxy, 2-nitro-4,5-dimethoxybenzyloxy, diphenylmethoxy, 4,4'-dimethoxydiphenylmethoxy or trityloxy, lower alkanoyloxymethoxy, for example acetoxymethoxy or pivaloyloxymethoxy, α-amino-lower alkanoyloxymethoxy, for example glycyloxymethoxy, 2-phthalidyloxy, pentachlorophenoxy, also tri-lower alkylsilyloxy, for example trimethylsilyloxy, and lower alkenyloxy, especially 2-lower alkenyloxy, for example allyloxy.

The invention relates primarily to 2-penem compounds of the formula I in which $R_1$ represents hydrogen, lower alkyl having up to 5 carbon atoms, such as methyl, isopropyl, or pentyl; lower alkoxy-lower alkyl having up to 4 carbon atoms, for example, methoxymethyl; or lower alkanoyloxy-lower alkyl having up to 4 carbon atoms, for example, acetoxymethyl; lower alkylthio-lower alkyl having up to 5 carbon atoms, for example, methylthiomethyl or tert.-butylthiomethyl; lower alkoxycarbonyl-lower alkyl having up to 5 carbon atoms, for example 2-methoxycarbonylethyl; aminolower alkyl such as aminomethyl, 2-aminoethyl or 3-aminopropyl, optionally N-acylated by benzyloxycarbonyl, p-nitrobenzyloxycarbonyl or by phenoxyacetyl; phenyl optionally substituted by dimethylamino; benzyl; pyridyl, for example 2-, 4- or especially 3-pyridyl; furyl, for example 3-furyl or especially 2-furyl; or thienyl, for example 3- or especially 2-thienyl; or lower alkylthio having up to 4 carbon atoms, for example, ethylthio; and $R_2$ primarily represents hydroxy, the above-mentioned etherified hydroxy groups that can be split under basic or neutral conditions or physiologically, especially p-nitrobenzyloxy or acetonyloxy, and to salts, especially pharmacologically usable non-toxic salts, of such compounds having salt-forming groups, such as the alkali metal, for example sodium, or alkaline earth metal, for example calcium, salts, or ammonium salts, inclusive of those with amines, of compounds of the formula I, in which $R_2$ represents hydroxy.

The invention relates primarily to 2-$R_1$-2-penem-3-carboxylic acid compounds, in which $R_1$ represents hydrogen, methyl, pentyl, acetoxymethyl, tert.-butylthiomethyl, 2-methoxycarbonylethyl, 2-aminoethyl, 3-aminopropyl, phenoxyacetylaminomethyl, 3-(2-phenoxyacetylamino)-propyl, phenyl, 3-dimethylaminophenyl, benzyl, 2-furyl, 3-pyridyl or ethylthio, and to the salts, especially the pharmaceutically usable salts of such compounds having salt-forming groups.

The new compounds may be produced by ring-closing an ylid compound of the formula

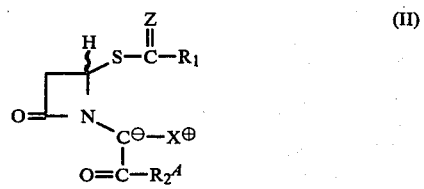

(II)

in which

Z represents oxygen or sulphur and $R_1$ and $R_2^A$ have the meanings given above, wherein functional groups in these radicals are preferably present in the protected form, and wherein $X^\oplus$ represents either a phosphonio group substituted three times, or a phosphono group esterified twice together with a cation, and, if desired or necessary, converting the protected carboxyl group of the formula —C(=O)—$R_2^A$ in a compound of the formula I obtained into the free or into a different protected carboxyl group, and/or, if desired, converting a compound of the formula I obtained into the corresponding 1-oxide and, if desired, converting this into a compound of the formula I, and/or, if desired, within the definition converting a compound of the formula I obtained into a different compound of the formula I, and/or, if desired, converting a compound obtained having a salt-forming group into a salt, or a salt obtained into the free compound or into a different salt, and/or, if desired, separating a mixture of isomeric compounds obtained into the individual isomers.

In the starting material of the formula II, $R_1$ is especially one of the preferred, optionally substituted hydrocarbon radicals, wherein functional groups are usually present in the protected form, amino, for example, in acylated form or alternatively in the form of the nitro or azido group.

In a starting material of the formula II, $R_2^A$ preferably represents an etherified hydroxy group forming together with the —C(=O)-grouping an esterified carboxyl group that can readily be split, especially under mild conditions, wherein functional groups that are optionally present in a carboxyl protective group $R_2^A$ may be protected in a manner known per se, for example as indicated above. A group $R_2^A$ is inter alia lower alkoxy, especially α-polybranched lower alkoxy, for example methoxy or tert.-butyloxy; lower alkenyloxy, especially 2-lower alkenyloxy, for example allyloxy; or 2-halo-lower alkoxy, for example 2,2,2-trichloroethoxy, 2-bromoethoxy, or 2-iodoethoxy; 2-lower alkylsulphonyl-lower alkoxy, for example 2-methylsulphonylethoxy; or an optionally substituted, such as lower alkoxy-, for example methoxy- or nitro-containing, 1-phenyl-lower alkoxy group, such as diphenylmethoxy or benzyloxy optionally substituted, for example as mentioned, for example benzyloxy, 4-methoxybenzyloxy, 4-nitrobenzyloxy, diphenylmethoxy or 4,4'-dimethoxydiphenylmethoxy; pentachlorophenoxy; acetonyloxy; 2-cyanoethoxy; a 2-($S_1$)($S_2$)($S_3$)-silylethoxy group, such as 2-trimethylsilylethoxy, 2-(dibutylmethylsilyl)-ethoxy or 2-triphenylsilylethoxy; also an organic silyloxy or stannyloxy group, such as tri-lower alkylsilyloxy, for example trimethylsilyloxy; or one of the mentioned etherified hydroxy groups that can be split physiologically.

The group $X^\oplus$ in the starting material of the formula II is one of the phosphonio or phosphono groups customary in the Wittig condensation reaction, especially a triaryl-, for example triphenyl-, or tri-lower alkyl-, for example tributylphosphonio group, or a phosphono group esterified twice by lower alkyl, for example ethyl, wherein the symbol $X^\oplus$ in the case of the phosphono group additionally includes the cation of a strong base, especially a suitable metal, such as alkali metal, for example a lithium, sodium or potassium, ion. Preferred as group $X^\oplus$ is in one case triphenylphosphonio and in the other case diethylphosphono together with an alkali metal ion, for example a sodium ion.

In phosphonium compounds of the formula II, which in the isomeric ylene form are alternatively called phosphorane compounds, the negative charge is neutralised by the positively charged phosphonio group. In phosphono compounds of the formula II, which in their isomeric form can alternatively be called phosphonate compounds, the negative charge is neutralised by the cation of a strong base, which cation, depending on the method of production of the phosphono starting material, may be, for example, an alkali metal ion, for example, a sodium, lithium or potassium ion. The phosphonate starting substances are therefore used as salts in the reaction.

Formula II shows the starting material in the form in which the ring closure takes place. Normally the corresponding phosphoranylidene compound of the formula

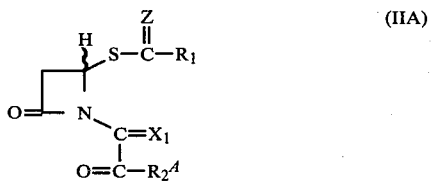

in which $X_1$ represents a tri-substituted, especially a triaryl-, for example triphenyl-, or a tri-lower alkyl-, for example tri-n-butyl-phosphoranylidene radical, or the corresponding phosphono compound of the formula

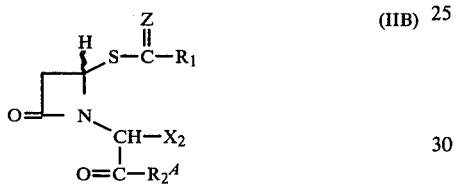

in which $X_2$ represents a phosphono-, especially a dialkylphosphono-, for example, a diethylphosphono group, is used, wherein a phosphono starting material of the formula IIB is converted into the form suitable for the ring closure, that is into the compound of the formula II, by treating with a suitable basic reagent, such as an inorganic base, for example an alkali metal carbonate, such as sodium or potassium carbonate, or with an organic base, such as a tri-lower alkylamine, for example triethylamine, or a cyclic base of the amidine type, such as an appropriate diaza-bicycloalkene compound, for example 1,5-diaza-bicyclo[5,4,0]undec-5-ene.

Preferred starting materials are the phosphoranylidene compounds of the formula IIA.

The ring closure can take place spontaneously, that is to say during the production of the starting materials, or by heating, for example in a temperature range of approximately 30° C. to approximately 160° C., preferably of approximately 50° C. to approximately 100° C.

The reaction is preferably carried out in the presence of a suitable inert solvent, such as in an aliphatic, cycloaliphatic or aromatic hydrocarbon, for example hexane, cyclohexane, benzene or toluene; a halogenated hydrocarbon, for example methylene chloride; an ether, for example diethyl ether; a lower alkylene glycol di-lower alkyl ether, for example dimethoxyethane or diethylene glycol dimethyl ether, or a cyclic ether, for example dioxan or tetrahydrofuran; a carboxylic acid amide, for example dimethylformamide; a di-lower alkyl sulphoxide, for example dimethyl sulphoxide; or a lower alkanol, for example methanol, ethanol or tert.-butanol; or in a mixture thereof, and, if necessary, in an inert gas atmosphere, for example an argon or nitrogen atmosphere. If necessary the reaction can be carried out in the presence of an antioxidant, such as a sterically hindered phenol, for example 2,6-di-tert.-butylcresol, or an optionally substituted 1,4-dihydroxybenzene, especially hydroquinone.

In a compound of the formula I obtainable according to the invention having a protected, especially an esterified, carboxyl group of the formula $—C(=O)—R_2^A$, the latter can be converted in a manner known per se, for example depending on the type of group $R_2^A$, into the free carboxyl group. For example, a carboxyl group esterified by a suitable 2-halo-lower alkyl group, an arylcarbonylmethyl group or a 4-nitrobenzyl group can be converted into the free carboxyl group for example by treating with a chemical reducing agent, such as a metal, for example zinc, or a reducing metal salt, such as a chromium(II) salt, for example chromium(II) chloride, usually in the presence of a hydrogen-yielding agent, which together with the metal enables the nascent hydrogen to be produced, such as an acid, chiefly acetic or formic acid, or an alcohol, wherein water is preferably added; a carboxyl group esterified by an arylcarbonylmethyl group can be converted into the free carboxyl group by treating with a nucleophilic, preferably salt-forming reagent, such as sodium thiophenolate or sodium iodide; and also a carboxyl group esterified by 4-nitrobenzyl can be converted into the free carboxyl group by treating with an alkali metal dithionite, for example sodium dithionite. A carboxyl group esterified by a 2-lower alkylsulphonyl-lower alkyl group can be split and released, for example by treating with a basic agent, for example one of the nucleophilic-reacting bases mentioned further below; a carboxyl group esterified by a suitable arylmethyl grouping can be split and released, for example by radiation, preferably with ultra-violet light, for example of less than 290 mµ when the arylmethyl group is, for example, a benzyl radical optionally substituted in the 3-, 4- and/or 5-position for example by lower alkoxy and/or nitro groups, or with longer-wave ultraviolet light, for example of above 290 mµ when the arylmethyl group is, for example, a benzyl radical substituted in the 2-position by a nitro group; a carboxyl group esterified by a suitably substituted methyl group, such as tert.-butyl or diphenylmethyl, can be split and released, for example, by treating with a suitable acid medium, such as formic acid or trifluoroacetic acid, optionally with the addition of a nucleophilic compound, such as phenol or anisole; and an esterified carboxyl group that can be split by hydrogenolysis, for example benzyloxycarbonyl or 4-nitrobenzyloxycarbonyl, can be split and released by hydrogenolysis, for example by treating with hydrogen in the presence of a noble metal, for example a palladium, catalyst. In addition, a carboxyl group esterified with a lower alkenyl group, such as with 2-lower alkenyl, especially allyl, can be converted oxidatively, for example by treating with ozone, followed by a reducing agent, for example dimethyl sulphide, into a formylmethoxycarbonyl group, from which the carboxyl group can be released by treating with a base, such as a secondary amine, for example dimethylamine; or a 2-lower alkenyloxycarbonyl group, for example allyloxycarbonyl, can be isomerised, for example by treating with tris-triphenylphosphine rhodium chloride, palladium-on-carbon, or an alkali metal lower alkanolate, for example, tert.-butylene, in dimethyl sulphoxide to form a 1-lower alkenyloxycarbonyl group and this can be split hydrolytically under weakly acidic or weakly basic conditions. A 2-oxoethoxycarbonyl or 2-cyanoethoxycarbonyl group optionally substituted in the 2-position by lower alkyl or by aryl, for example the acetonyloxycarbonyl or 2-cyanoethoxycarbonyl group, can be converted under mild conditions, that is at room temperature or while cooling, by treatment with a suitable base, into the corresponding salt of this carboxyl group, from which the free carboxyl group can be obtained by acidification. Suitable bases are nucleophilic-reacting metal, such as alkaline earth metal, and especially alkali metal, bases, such as corresponding hydroxides, carbonates, bicarbonates, alkoxides, phenolates, mercaptides, thiophenolates or amides, for example sodium hydroxide, sodium carbonate, sodium bicarbonate, sodium ethanolate, sodium thiophenolate, sodium amide or sodium morpholide, or corresponding lithium or potassium compounds, which are used in water in aqueous or hydroxyl group-containing solvents or alternatively in polar inert solvents with subsequent treatment with water. To split the 2-cyanoethoxycarbonyl groups, it is also possible to use tertiary amines, such as tri-lower alkylamine, for example triethylamine or Hünig base, or cyclic or bicyclic amines or imines, such as N-methylmorpholine or 1,5-diazabicyclo[5,4,0]undec-5-ene, in an inert solvent, such as methylene chloride or tetrahydrofuran, wherein the corresponding ammonium salt of the carboxyl compound are obtained directly. A substituted silylethoxycarbonyl group can be converted into the free carboxyl group by treatment with a salt of hydrofluoric acid that yields fluoride anions, such as an alkali metal fluoride, for example sodium or potassium fluoride, in the presence of a macrocyclic polyether ("Crown ether"), or with a fluoride of an organic quaternary base, such as tetraalkylammonium fluoride or trialkylarylammonium fluoride, for example tetraethylammonium fluoride or tetrabutylammonium fluoride, in the presence of an aprotic polar solvent, such as dimethyl sulphoxide or N,N-dimethylacetamide. A pentachlorophenyloxycarbonyl group can be converted into a free carboxyl group under mild conditions, for example by dilute sodium carbonate solution or sodium bicarbonate solution or by an organic base in the presence of water.

A carboxyl group protected, for example, by silylation or stannylation, can be released in the usual manner by solvolysis for example by treating with water or an alcohol.

If there is more than one protected carboxyl group present in a compound obtainable in accordance with the invention, these may be converted into free carboxyl groups either jointly or selectively.

In a compound of the formula I obtainable in accordance with the process that contains a free carboxyl group of the formula —C(=O)—OH, such a group can be converted in a manner known per se into a protected carboxyl group. For example, esters are obtained, for example by treating with a suitable diazo compound, such as a diazo-lower alkane, for example diazomethane or diazobutane, or a phenyldiazo-lower alkane, for example diphenyldiazomethane, if necessary in the presence of a Lewis acid, such as, for example, boron trifluoride, or by reacting with an alcohol suitable for esterification in the presence of an esterifying agent, such as a carbodiimide, for example dicyclohexylcarbodiimide, or carbonyldiimidazole, or further with an N,N'-disubstituted O- or S-substituted isourea or isothiourea, in which an O- and S-substituent is, for example, lower alkyl, especially tert.-butyl, phenyl-lower alkyl or cycloalkyl, and N- or N'-substituents are, for example, lower alkyl, especially isopropyl, cycloalkyl or phenyl, or according to any other known and suitable method of esterification, such as reacting a salt of the acid with a reactive ester of an alcohol and a strong inorganic acid or strong organic sulphonic acid. Further, acid halides, such as acid chlorides (produced, for example, by treating with oxalyl chloride, activated esters (formed, for example, with an N-hydroxy nitrogen compound, such as N-hydroxysuccinimide) or mixed anhydrides (obtained, for example, with haloformic acid lower alkyl esters, such as chloroformic acid ethyl ester or chloroformic acid isobutyl ester, or with haloacetic acid halides, such as trichloroacetic acid chloride) can be converted into an esterified carboxyl group by reacting with alcohols, optionally in the presence of a base, such as pyridine.

In a compound of the formula I having an esterified grouping of the formula —C(=O)—$R_2^4$, this grouping can be converted into a different esterified carboxy group of this formula, for example 2-chloroethoxycarbonyl or 2-bromoethoxycarbonyl can be converted into 2-iodoethoxycarbonyl by treating with an iodine salt, such as sodium iodide, in the presence of a suitable solvent, such as acetone.

In a compound having a free carboxyl group of the formula —C(=O)—OH obtainable according to the process, such a group can also be converted into an optionally substituted hydrazinocarbonyl group, by reacting preferably reactive functionally modified derivatives such as the above-mentioned acid halides, generally esters such as the above-mentioned activated esters, or mixed anhydrides of the corresponding acid with hydrazines.

A carboxyl group protected by an organic silyl or stannyl group can be formed in a manner known per se, for example by treating compounds of the formula I in which $R_2$ represents hydroxy, or salts, such as alkali metal salts, for example sodium salts, thereof, with a suitable silylation or stannylation agent, such as one of the above-mentioned silylation or stannylation agents.

In the process according to the invention, and in additional steps to be carried out where applicable and where necessary, if required free functional groups that do not participate in the reaction are transiently protected in a manner known per se: for example, free amino groups are transiently protected, for example by acylation, tritylation or silylation; free hydroxy groups, for example by etherification or esterification; and free carboxyl groups or sulpho groups, for example by esterification, inclusive of silylation: and can, if desired, be released individually or jointly in a manner known per se after the reaction. For example, amino, hydroxy, mercapto, carboxyl or sulpho groups present in a starting material may be protected, for example in the form of acylamino groups, such as those mentioned above, for example the 2,2,2-trichloroethoxycarbonylamino group, 2-bromoethoxycarbonylamino group, 4-methoxybenzyloxycarbonylamino group, or tert.-butyloxycarbonylamino group, or in the form of aryl- or aryl-lower alkylthioamino groups, for example the 2-nitrophenylthioamino group or arylsulphonylamino group, for example the 4-methylphenylsulphonylamino group, in the form of 1-lower alkoxycarbonyl-2-propylideneamino groups or of the o-nitrophenoxyacetylamino group, or of acyloxy groups, such as those mentioned above, for example the tert.-butyloxycarbonyloxy group, 2,2,2-trichloroethoxycarbonyloxy group, 2-bromoethoxycarbonyloxy group or p-nitrobenzyloxycarbonyloxy group, or corresponding acylmercapto groups, or in the form of esterified carboxy groups, such as those mentioned above, for example the diphenylmethoxycarbonyl group, p-nitrobenzyloxycarbonyl group, acetonyloxycarbonyl group or 2-cyanoethoxycarbonyl group, or of substituted sulpho groups, such as the above-mentioned lower alkylsulpho groups, for example the methylsulpho group, and when the reaction is complete may be released, optionally after converting the protective group. For example, a 2,2,2-trichloroethoxycarbonylamino group or 2-iodoethoxycarbonylamino group or alternatively a p-nitrobenzyloxycarbonylamino group may be split by treating with suitable reducing agents, such as zinc in the presence of aqueous acetic acid or hydrogen in the presence of a palladium catalyst; a diphenylmethoxycarbonylamino group or tert.-butylcarbonylamino group may be split by treating with formic acid or trifluoroacetic acid; an aryl- or aryl-lower alkylthioamino group may be split by treating with a nucleophilic reagent such as sulphurous acid; an arylsulphonylamino group may be split by means of electrolytic reduction; a 1-lower alkoxycarbonyl-2-propylideneamino group by treating with aqueous mineral acid, and a tert.-butyloxycarbonyloxy group by treating with formic or trifluoroacetic acid or a 2,2,2-trichloroethoxycarbonyloxy group or p-nitrobenzyloxycarbonyloxy group may be split by treating with a chemical reducing agent, such as zinc in the presence of aqueous acetic acid, or with hydrogen in the presence of a palladium catalyst; and a diphenylmethoxycarbonyl group that may be split by treating with formic or trifluoroacetic acid or by hydrogenolysis; an acetonyloxy- or cyanoethoxycarbonyl group may be split by treating with bases, such as sodium bicarbonate or 1,5-diazabicyclo[5,4,0]undec-5-ene, and a substituted sulpho group by treating with an alkali metal halide; the splitting may, if desired, in each case be carried out in stages.

Furthermore, in compounds of the formula I that contain in the groups $R_1$ and $R_2$ functional substituents such as free amino, hydroxy, carboxy or sulpho groups, these groups may be functionally modified by processes known per se, for example by acylation or esterification or substitution. For example, an amino group may be converted into a sulphoamino group by treating with sulphur trioxide, preferably in the form of a complex with an organic base such as a tri-lower alkylamine, for example triethylamine. Also, the reaction mixture obtained by reacting an acid addition salt of 4-guanyl-semicarbazide with sodium nitrite can be reacted with a compound of the formula I in which $R_1$ contains an amino group, and the amino group thus converted into a 3-guanylureido group. Furthermore, compounds with aliphatically-bonded halogen, for example with an optionally substituted α-bromoacetyl grouping, can be reacted with esters of phosphorous acid, such as tri-lower alkyl phosphite compounds, and thus be made into corresponding phosphono compounds.

In addition, in resulting compounds functional substituents in the radicals $R_1$ and $R_2^A$ may be converted into other functional groups: a nitro or azido group, for example, may be converted into an amino group by treating with hydrogen that is catalytically activated by, for example, a palladium or platinum oxide catalyst.

The 2-penem compounds of the formula I obtained may be converted in a manner known per se by oxidation with suitable oxidising agents such as hydrogen peroxide, or peracids, for example peracetic acid or 3-chloroperbenzoic acid, into their 1-oxides. The 1-oxides of 2-penem compounds of the formula I obtained may be reduced to the corresponding 2-penem compounds of the formula I in a manner known per se by reducing with suitable reducing agents such as phosphorus trichloride. In these reactions care must be taken that if necessary free functional groups are protected and, if desired, subsequently released again.

Salts of compounds of the formula I may be produced in a manner known per se. For example, salts of such compounds with acid groups can be formed, for example by treating with metal compounds such as alkali metal salts of suitable carboxylic acids, for example the sodium salt of α-ethylcaproic acid, or with ammonia or a suitable organic amine, wherein preferably stoichiometric amounts or only a small excess of the salt-forming medium is used. Acid addition salts of compounds of the formula I with basic groupings are obtained in the usual manner, for example by treating with an acid or a suitable anion exchange reagent. Inner salts of compounds of the formula I which contain, for example, a salt-forming amino group and a free carboxyl group may be formed, for example, by neutralising salts such as acid addition salts to the isoelectric point, for example with weak bases, or by treating with liquid ion exchangers. Salts of 1-oxides of compounds of the formula I with salt-forming groups may be produced in an analogous manner.

Salts may be converted in the usual manner into the free compounds: metal and ammonium salts, for example, by treating with suitable acids, and acid addition salts, for example, by treating with a suitable basic agent.

Mixtures of isomers obtained may be separated into the individual isomers by methods known per se: mixtures of diastereomeric isomers, for example, by fractional crystallisation, adsorption chromatography (column or thin-layer chromatography) or other suitable separating processes. Racemic compounds obtained can be separated into the antipodes in the usual manner, optionally after introducing suitable salt-forming groupings, for example by forming a mixture of diastereoisomeric salts with optically active salt-forming agents, separating the mixture into the diastereoisomeric salts and then into the free compounds, or by fractional crystallisation from optically active solvents.

In all subsequent conversions of the compounds obtained, the reactions that are preferred are those carried out under neutral, alkaline or weakly basic conditions.

The process also includes those embodiments according to which compounds produced as intermediate products are used as starting substances and the remaining process steps are carried out with these, or according to which the process is interrupted at any stage; furthermore, starting substances may be used in the form of derivatives or may be formed in situ, optionally under the conditions of the reaction. For example, a starting material of the formula II in which Z is oxygen may be produced in situ from a compound of the formula II in which Z' is an optionally substituted methylidene group, by ozonisation and subsequent reduction of the ozonide formed, analogously to the method given in stage 2,5, whereupon, especially when $R_1$ is hydrogen, the cyclisation to the compound of the formula I takes place in the reaction solution.

The starting materials of the formula II, and IIA or IIB used in accordance with the invention may be produced, for example, according to the following reaction scheme:

Reaction Scheme 1

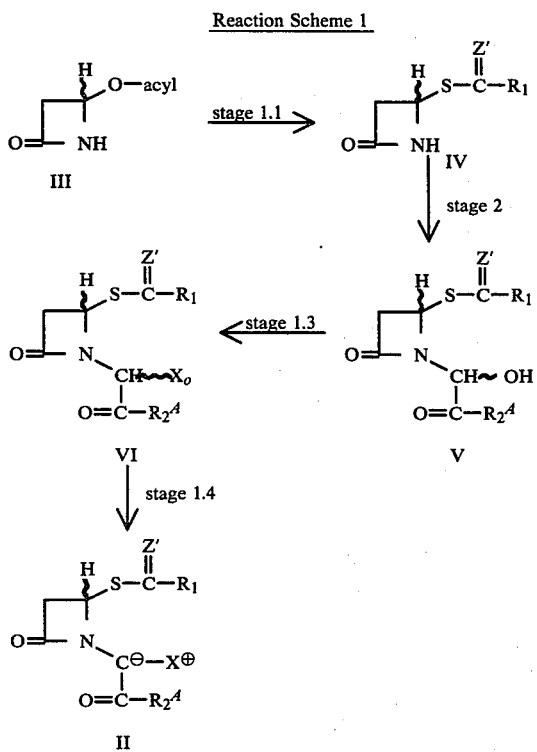

In the compounds of the formulae IV, V, VI and II in the reaction scheme I and in the compounds of the formulae Xa, XI, XII and IVa in the reaction scheme 2, Z' is oxygen, sulphur or alternatively, especially when $R_1$ is hydrogen, a methylidene group optionally substituted by one or two substituents Y, which group can be converted by oxidation into an oxo group Z. A substituent Y of this methylidene group is an organic radical, for example one of the organic radicals mentioned under $R_1$, such as one of the mentioned, optionally substituted, lower-alkyl, cycloalkyl, cycloalkyl-lower-alkyl, phenyl or phenyl-lower alkyl radicals, and especially one of the functionally modified, such as esterified, carboxyl groups. Esterification with an optically active alcohol such as l-menthol is included. This methylidene group preferably carries one of the substituents mentioned. The 2-methoxycarbonylmethylidene and the 2-(l)-menthyloxycarbonylmethylidene group Z' are singled out. The latter can be used for the production of optically active compounds of the formulae IV to VI and II.

Stage 1.1

A thioazetidinone of the formula IV is obtained by treating an acyloxyazetidinone of the formula III with a mercapto compound $R_1$—C(=Z')—SH or with a salt, for example an alkali metal salt such as a sodium salt thereof, and, if desired, separating an isomeric mixture obtained into the individual isomers, if desired converting a group $R_1$ in a compound obtained into a different group $R_1$, and/or, if desired, converting an optionally substituted methylidene group Z' into an oxo group Z.

Acyloxyazetidinones of the formula III are known (German Offenlegungsschrift No. 1 906 401) or can be produced according to known methods. The acyl radical may have the same meaning as the acyl radical $R_1$—CO—. The acyl radical may alternatively be derived from an optically active acid. A preferred acyl radical is acetyl.

This nucleophilic substitution may be carried out under neutral or weakly basic conditions in the presence of water and optionally a water-miscible organic solvent. The basic conditions may be established, for example, by the addition of an inorganic base such as an alkali metal or an alkaline earth metal hydroxide, -carbonate or -bicarbonate, for example sodium, potassium or calcium-hydroxide, -carbonate or -bicarbonate. The organic solvents that may be used are, for example, water-miscible alcohols, for example, lower alkanols such as methanol or ethanol; ketones, for example lower alkanones such as acetone; amides, for example lower alkanecarboxylic acid amides such as dimethylformamide, and the like. The reaction is usually carried out at room temperature but can be carried out at elevated or reduced temperature.

Both an optically inactive (4R,S)-compound of the formula III and a corresponding optically active (4R)- or (4S)-compound can be used in the reaction. A racemic compound of the formula IV obtained can be separated into the optically active compounds. The racemic compound of the formula IV in which $R_1$ is methyl and Z' represents oxygen is known (K. Clauss et al., Liebigs Ann. Chem. 1974, 539-560).

A mercapto compound $R_1$—C(=Z')—SH, in which Z' represents a methylidene group optionally substituted by one or two substituents Y, or a salt thereof, may optionally be produced in situ by treating a corresponding isothiouronium salt of the formula $R_1$—C(=Z')—S—C (NH$_2$)(=NH$_2^\oplus$).A$^\ominus$, in which A$^\ominus$ represents an anion, for example the chloride anion, in water, an alcohol such as methanol or ethanol, or a mixture of water and alcohol, with a base, for example an alkali metal hydroxide such as sodium hydroxide.

Stage 1.2

An α-hydroxy-carboxylic compound of the formula V is obtained by reacting a compound of the formula IV with a glyoxylic acid compound of the formula OH—C—C(=O)—$R_2^A$ or a suitable derivative such as a hydrate, hemihydrate or semiacetal, for example a semiacetal with a lower alkanol, for example, methanol or ethanol, if desired separating a so-obtained isomeric mixture into the individual isomers, if desired converting a group $R_1$ in a compound obtained into a different group $R_1$ and/or, if desired, converting an optionally substituted methylidene group Z' into an oxo group Z.

The compound V is usually obtained as a mixture of the two isomers (with reference to the grouping >CH〜OH). It is possible, however, also to isolate the pure isomers therefrom.

The addition reaction of the glyoxylic acid ester compound to the nitrogen atom of the lactam ring takes place at room temperature or, if necessary, while heating, for example up to approximately 100° C., and in the absence of an actual condensation agent and/or without the formation of a salt. When using the hydrate of the glyoxylic acid compound, water is formed which, if necessary, is removed by distillation, for example azeotropically, or by using a suitable dehydration agent such as a molecular sieve. Preferably the process is carried out in the presence of a suitable solvent, such as, for example, dioxan, toluene or dimethylformamide, or of a solvent mixture, if desired or necessary in an inert gas atmosphere, such as a nitrogen atmosphere.

Both an optically inactive (4R,S)-compound of the formula IV and a corresponding optically active (4R)- or (4S)-compound can be used in the reaction. A racemic compound of the formula V obtained can be separated into the optically active compounds.

Stage 1.3

Compounds of the formula VI, in which $X_o$ represents a reactive esterified hydroxy group, especially halogen or organic sulphonyloxy, are produced by converting the secondary hydroxy group in a compound of the formula V into a reactive esterified hydroxy group, especially into halogen, for example chlorine or bromine, or into an organic sulphonyloxy group such as lower alkylsulphonyloxy, for example methylsulphonyloxy, or arylsulphonyloxy, for example 4-methylphenylsulphonyloxy, if desired separating an isomeric mixture obtained into the individual isomers, if desired converting a group $R_1$ in a compound obtained into a different group $R_1$ and/or, if desired, converting an optionally substituted methylidene group $Z'$ into an oxo group Z.

The compound VI may be obtained in the form of mixtures of the isomers (with reference to the grouping >CH ∼∼∼ $X_o$) or in the form of pure isomers.

The above reaction is carried out by treating with a suitable esterifying agent, using, for example, a halogenating agent such as a thionyl halide, for example the chloride, a phosphorus oxyhalide, especially the chloride, or a halophosphonium halide such as triphenylphosphine dibromide or diiodide, and a suitable organic sulphonic acid halide such as the chloride, preferably in the presence of a basic, primarily an organic basic, agent such as an aliphatic tertiary amine, for example triethylamine, diisopropylethylamine or "polystyrene-Hünig base", or a heterocyclic base of the pyridine type, for example pyridine or collidine. Preferably the reaction is carried out in the presence of a suitable solvent, for example dioxan or tetrahydrofuran, or of a suitable solvent mixture, if necessary while cooling and/or in an inert gas atmosphere, such as a nitrogen atmosphere.

In a compound of the formula IV obtainable in this manner, a reactive esterified hydroxy group $X_o$ can be converted into a different reactive esterified hydroxy group in a manner known per se. For example, a chlorine atom can be exchanged for a bromine or iodine atom by treating the corresponding chlorine compound with a suitable bromine or iodine reagent, especially with an inorganic bromide or iodide salt such as lithium bromide, preferably in the presence of a suitable solvent such as ether.

Both an optically inactive (4R,S)-compound of the formula V and a corresponding optically active (4R)- or (4S)-compound can be used in the reaction. A racemic compound of the formula VI obtained can be separated into the optically active compounds.

Stage 1.4

A starting material of the formula II is obtained by treating a compound of the formula VI in which $X_o$ represents a reactive esterified hydroxy group, with a suitable phosphine compound such as tri-lower alkylphosphine, for example tri-n-butylphosphine, or a triarylphosphine, for example triphenylphosphine or with a suitable phosphite compound such as a tri-lower alkyl phosphite, for example triethyl phosphite, or an alkali metal dimethyl phosphite, or by treating a compound of the formula V with carbon tetrachloride and a phosphine, wherein depending on the choice of reagent a compound of the formula IIA or IIB can be obtained, if desired converting a group $R_1$ in a compound obtained into a different group $R_1$, and/or if desired converting an optionally substituted methylidene group $Z'$ into an oxo group Z.

The reaction using the compound of the formula VI as starting material is preferably carried out in the presence of a suitable inert solvent such as a hydrocarbon, for example hexane, cyclohexane, benzene, toluene or xylene; or an ether, for example dioxan, tetrahydrofuran or diethylene glycol dimethyl ether, or of a solvent mixture. Depending on the reactivity, the operation is carried out while cooling or at elevated temperature, approximately between −10° and +200°, preferably at approximately 20° to 180°, and/or in an inert gas atmosphere, such as a nitrogen atmosphere. In order to prevent oxidation processes, catalytic amounts of an antioxidant, for example p-hydroquinone, may be added.

When using a phosphine compound the reaction is usually carried out in the presence of a basic agent, such as an organic base, for example an amine, such as triethylamine, diisopropylethylamine or "polystyrene-Hünig base", and thus the phosphoranylidene starting material of the formula IIA, which is formed from the corresponding phosphonium salt, is obtained directly.

The reaction using a compound of the formula V as starting material is carried out in a solvent under mild conditions, that is to say, at temperatures of −10° to approximately 40°, preferably at room temperature. An excess of carbon tetrachloride especially to which methylene chloride may additionally be added, is used as solvent. The above-mentioned tri-lower alkyl- or triarylphosphines, especially triphenylphosphine, of which two equivalents are used, are suitable phosphines.

Both an optically inactive (4R,S)-compound of the formula VI or V and a corresponding optionally active (4R)- or (4S)-compound may be used in the reaction. A racemic compound of the formula II obtained can be separated into the optically active compounds.

The above-mentioned racemic compounds are split into their optical antipodes by methods known per se.

One of these methods consists in reacting a racemic compound with an optically active auxiliary substance, separating the resulting mixture of two diastereoisomeric compounds by means of suitable physical/chemical methods and then splitting the individual diastereoisomeric compounds into the optically active starting materials.

Particularly suitable racemic compounds for separating into antipodes are those that possess an acidic group, for example the racemic compound of the compound of the formula I. Others of the described racemic compounds can be converted into acidic racemic compounds by simple reactions. For example, racemic compounds carrying aldehyde or keto groups react with a hydrazine derivative carrying acid groups, for example 4-(4-carboxyphenyl)-semicarbazide to form the corresponding hydrazone derivatives, or compounds containing alcohol groups react with a dicarboxylic acid anhydride, for example phthalic acid anhydride, to form the racemic compound of an acid semiester.

These acidic racemic compounds may be reacted with optically active bases, for example esters of optically active amino acids, or (−)-brucine, (+)-quinidine, (−)-quinine, (+)-cinchonine, (+)-dehydroabietylamine, (+)- and (−)-ephedrine, (+)- and (−)-1-phenylethylamine or their N-mono- or dialkylated derivatives to form mixtures consisting of two diastereoisomeric salts.

In racemic compounds containing carboxyl groups, for example in racemic compounds that contain a functionally modified carboxymethylidene group Z', this carboxyl group may already be esterified by, or esterification may be carried out by, an optically active alcohol such as (−)-menthol, (+)-borneol, (+)- or (−)-2-octanol, whereupon after subsequent isolation of the desired diastereoisomer, the carboxyl group is released, or the part of the molecule containing the esterified carboxyl group, for example the esterified carboxymethylidene radical, is split off.

Racemic compounds containing hydroxy groups may likewise be split into their optical antipodes, for which, especially, optically active acids or their reactive functional derivates that form diastereoisomeric esters with the said alcohols are used. Such acids are, for example, (−)-abietic acid, D(+)- and L(−)-malic acid, N-acylated optically active amino acids, (+)- and (−)-camphanic acid, (+)- and (−)-ketopinic acid, L(+)-ascorbic acid, (+)-camphoric acid, (+)-camphor-10-sulphonic acid($\beta$), (+)- or (−)-$\alpha$-bromocamphor-$\pi$-sulphonic acid, D(−)-quinic acid, D(−)-isoascorbic acid, D(−)- and L(+)-mandelic acid, (+)-1-menthoxy acetic acid, D(−)- and L(+)-tartaric acid and their di-O-benzoyl- and di-O-p-toluyl derivatives. The acyl radicals of the optically active acids mentioned may be present, for example, as acyl in compounds of the formula III or as ($R_1$—C(=O))— in compounds of the formulae II and IV to VI, and render possible the splitting of the racemates of such compounds. If desired or necessary, when the splitting of the racemic compound is complete the optically active group $R_1$—C(=O)— can be converted into a desired optically inactive group $R_1$—C(=O)—.

Racemic compounds containing hydroxy groups may be converted into a mixture of diastereoisomeric urethanes, for example by reacting with optically active isocyanates, such as with (+)- or (−)-1-phenylethyl isocyanate.

Basic racemic compounds can form diastereoisomeric salts with the above-mentioned acids. Racemic compounds containing double bonds may be converted, for example by platinum chloride and (+)-1-phenyl-2-aminopropane, into mixtures of diastereoisomeric complex salts.

Physical/chemical methods, chiefly fractional crystallisation, are suitable for separating the diastereoisomeric mixtures. It is also possible, however, to use chromatographic methods, above all solid-liquid chromatography. Readily volatile diastereoisomeric mixtures may also be separated by distillation or gas chromatography.

Splitting the separated diastereoisomers into the optically active starting materials is likewise carried out according to customary methods. The acids or the bases are freed from the salts, for example by treating with stronger acids or bases respectively than those originally used. The desired optically active compounds are obtained from the esters and urethanes, for example by alkaline hydrolysis or by reduction with a complex hydride such as lithium aluminium hydride.

A further method of separating the racemic compounds consists in the chromatography on optically active absorption layers, for example on unrefined sugar.

According to a third method, the racemic compounds are dissolved in optically active solvents and the more sparingly soluble antipode is crystallised out.

In a fourth method the different reactivity of the optical antipodes in comparison with the biological material, such as microorganisms or isolated enzymes, is used.

According to a fifth method, the racemic compounds are dissolved and one of the optical antipodes is crystallised out by injecting a small amount of an optically active product obtained according to the above methods.

Optically active trans-compounds of the formula IVa that can be used according to the invention may also be produced in accordance with the following reaction scheme:

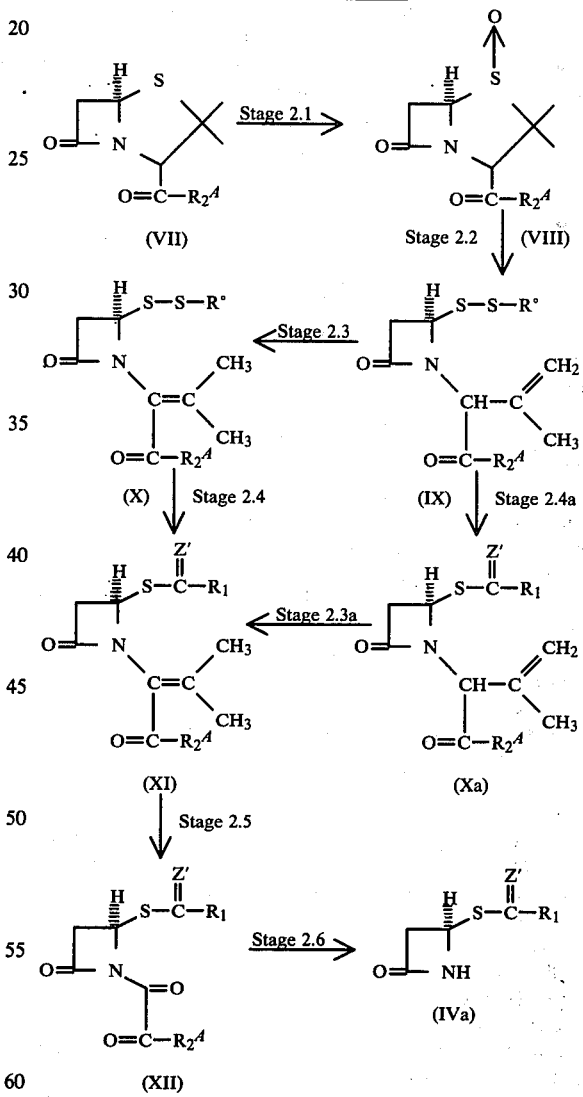

Reaction scheme 2

In the compounds of the formulae VII to XII, $R_2^A$ preferably represents lower alkoxy, especially methoxy.

Stage 2.1

An oxide of a penicillanic acid compound of the formula VIII is obtained by oxidising a penicillanic acid compound of the formula VII in the 1-position. The oxidation is carried out in a manner known per se with suitable oxidising agents, such as hydrogen peroxide or inorganic or organic peracids. Suitable inorganic peracids are, for example, periodic or persulphuric acid. Suitable organic peracids are, for example, percarboxylic acids, such as performic acid, peracetic acid, trifluoroperacetic acid, permaleic acid, perbenzoic acid, 3-chloroperbenzoic acid or monoperphthalic acid, or persulphonic acids, for example p-toluenepersulphonic acid. The peracids may also be produced in situ from hydrogen peroxide and the corresponding acids. The oxidation is carried out under mild conditions, for example at temperatures of approximately −50° to approximately +100°, preferably at approximately −10° to approximately +40°, in an inert solvent.

Starting compounds of the formula VII are known or can be produced according to known processes. For example, they may be obtained by hydrogenation of potassium-6α-bromopenicillanic acid and subsequent esterification of the carboxyl group [E. Evrard, M. Claesen and H. Vanderhaege, Nature 201, 1124 (1964)] or by hydrogenation of 6,6-dibromopenicillanic acid esters, for example the methyl ester [J. P. Clayton, J. Chem. Soc. (C), 2123 (1969)].

Stage 2.2

A 3-methylenebutyric acid compound of the formula IX is obtained by treating a 1-oxide of a penicillanic acid compound of the formula VIII with a mercapto compound R°-SH.

In the mercapto compound R°-SH and in the reaction product of the formula IX, R° is an optionally substituted aromatic heterocyclic radical having up to 15, preferably up to 9, carbon atoms, and at least one ring nitrogen atom, and optionally a further ring hetero atom, such as oxygen or sulphur, which radical is bonded to the thio group —S— by one of its ring carbon atoms that is bonded to a ring nitrogen atom by a double bond. Radicals of this type are monocyclic or bicyclic and may be substituted, for example by lower alkyl, such as methyl or ethyl, lower alkoxy, such as methoxy or ethoxy, halogen, such as fluorine or chlorine, or aryl, such as phenyl.

Radicals R° of this type are, for example, monocyclic five-membered thiadiazacyclic, thiatriazacyclic, oxadiazacyclic or oxatriazacyclic radicals of aromatic character, especially monocyclic five-membered diazacyclic, oxazacyclic and thiazacyclic radicals of aromatic character, and/or primarily the corresponding benzdiazacyclic, benzoxazacyclic or benzthiazacyclic radicals, in which the heterocyclic part is five-membered and has an aromatic character, wherein in R° radicals a substitutable ring nitrogen atom may be substituted, for example by lower alkyl. Representative of such R° groups are 1-methylimidazol-2-yl, 1,3-thiazol-2-yl, 1,3,4-thiadiazol-2-yl, 1,3,4,5-thiatriazol-2-yl, 1,3-oxazol-2-yl, 1,3,4-oxadiazol-2-yl, 1,3,4,5-oxatriazol-2-yl, 2-quinolyl, 1-methylbenzimidazol-2-yl, benzoxazol-2-yl and especially benzthiazol-2-yl.

The reaction is carried out in an inert solvent, such as an aliphatic or aromatic hydrocarbon, for example benzene or toluene, while warming up to the reflux temperature of the solvent used.

Stage 2.3

A 3-methylcrotonic acid compound of the formula X is obtained by isomerising a 3-methylenebutyric acid compound of the formula IX by treating with a suitable basic agent.

Suitable basic agents are, for example, organic nitrogen bases such as tertiary amines, for example tri-lower alkylamines such as triethylamine or H/ünig base, or inorganic bases, which are used in an inert solvent, such as an optionally halogenated hydrocarbon, for example methylene chloride, at room temperature or optionally slightly reduced or elevated temperature.

Stage 2.4

A thio compound of the formula XI is obtained by treating a compound of the formula X with a suitable reducing agent and simultaneously or subsequently reacting with an acylation derivative of a carboxylic acid of the formula $R_1$—C(=Z)—OH, or, when Z' represents a methylidene group optionally substituted by Y, reacting with an alkyne of the formula $R_1$—C≡C—Y, and, if desired, converting a group $R_1$ in a compound so obtained into a different group $R_1$, and/or, if desired, converting an optionally substituted methylidene group Z' into an oxo group Z.

Suitable reducing agents are, for example, hydride reducing agents such as alkali metal borohydrides, for example sodium borohydride, or also zinc in the presence of a carboxylic acid, for example a carboxylic acid of the formula $R_1$—C(=Z)—OH. The hydride reducing agents are usually used in the presence of suitable solvents, such as dimethylformamide. The hydride reduction is preferably carried out in dimethylformamide with sodium borohydride at temperatures of approximately −50° to approximately −10°, preferably at approximately −20°, whereupon at the same temperature the acylating agent and optionally a tertiary base, such as pyridine, are added. The reduction with zinc and a carboxylic acid is optionally carried out in a solvent, for which the carboxylic acid, if liquid, can itself be used, at temperatures of approximately −10° to approximately +50°, preferably at approximately 0° to room temperature. The acylating agent can be added to the reduction mixture from the beginning or when reduction is complete and optionally after evaporating off the carboxylic acid used and/or the solvent. Suitable acylating agents are especially anhydrides of the carboxylic acids mentioned, such as symmetric anhydrides, for example acetic anhydride, or mixed anhydrides, preferably those with halogen hydracids, that is the corresponding carboxylic acid halides, for example the chlorides and bromides, such as acetylbromide. For example, a compound of the formula X may be converted with zinc in a mixture of acetic acid and acetic anhydride at 0° to approximately 20° into a compound of the formula XI, in which $R_1$ is methyl. Owing to the reduced risk of racemisation, the zinc/carboxylic acid reduction is preferred. The alkyne can also be added to the reduction solution from the beginning or when reduction is complete. The addition of the 4-mercaptoazetidin-2-one, produced as an intermediate product in the reduction, to the triple bond of the alkyne takes place spontaneously at the reduction temperature.

Stage 2.3a

A thio compound of the formula XI is also obtained by isomerising a compound of the formula Xa in accordance with the reaction conditions of stage 2.3 by treating with a suitable basic agent, if desired converting a group $R_1$ in a compound obtained into a different group $R_1$, and/or, if desired, converting an optionally substituted methylidene group $Z'$ into an oxo group $Z$.

Stage 2.4a

A compound of the formula Xa is obtained by treating a 3-methylenebutyric acid compound of the formula IX in accordance with the reaction conditions of stage 2.4 with a suitable reducing agent, and simultaneously or subsequently reacting with an acylating derivative of a carboxylic acid of the formula $R_1$—C(=Z)—OH, or, when $Z'$ represents a methylidene group optionally substituted by Y, with an alkyne of the formula $R_1$—C≡C—Y, and, if desired, converting a group $R_1$ in a compound obtained into a different group $R_1$, and/or, if desired, converting an optionally substituted methylidene group $Z'$ into an oxo group $Z$.

Stage 2.5

A 2-oxoacetic acid compound of the formula XII is obtained by ozonising a compound of the formula XI and splitting the ozonide formed to the oxo group by means of reduction, and if desired converting a group $R_1$ in a compound obtained into a different group $R_1$, and/or, if desired, converting an optionally subsituted methylidene group $Z'$ into an oxo group $Z$.

The ozonisation is usually carried out with an ozone/oxygen mixture in an inert solvent, such as a lower alkanol, for example methanol or ethanol, a lower alkanone, for example acetone, an optionally halogenated aliphatic, cycloaliphatic or aromatic hydrocarbon, for example a halogen-lower alkane, such as methylene chloride or carbon tetrachloride, or in a solvent mixture, including an aqueous mixture, preferably while cooling, for example at temperatures of approximately $-90°$ to approximately $0°$.

An ozonide obtained as intermediate product is, usually without having to be isolated, split reductively to form a compound of the formula XII, wherein catalytically activated hydrogen, for example hydrogen in the presence of a heavy metal hydrogenating catalyst, such as a nickel catalyst or palladium catalyst, preferably on a suitable carrier material, such as calcium carbonate or carbon, is used; or chemical reducing agents, such as reducing heavy metals, including heavy metal alloys or amalgams, for example zinc, in the presence of a hydrogen donor such as an acid, for example acetic acid, or of an alcohol, for example a lower alkanol, are used; or reducing inorganic salts, such as alkali metal iodides, for example sodium iodide, or alkali metal bisulphites, for example, sodium bisulphite, in the presence of a hydrogen donor, such as an acid, for example acetic acid, or water, are used; or reducing organic compounds such as formic acid are used. It is also possible to use as reducing agents compounds that may readily be converted into corresponding epoxy compounds or oxides, wherein the epoxide formation can take place on account of a C,C-double bond and the oxide formation on account of an oxide-forming hetero atom, such as a sulphur, phosphorus or nitrogen atom. Compounds of this type are, for example, suitably substituted ethylene compounds (which are converted into ethylene oxide compounds in the reaction) such as tetracyanoethylene, in paricular suitable sulphide compounds (which in the reaction are converted into sulphoxide compounds), such as di-lower alkyl sulphides, especially dimethyl sulphide, suitable organic phosphorus compounds, such as a phosphine, which may contain optionally substituted aliphatic or aromatic hydrocarbon radicals as substituents (and which in the reaction is converted into a phosphine oxide), such as tri-lower alkylphosphines, for example tri-n-butylphosphine, or triarylphosphines, for example triphenylphosphine, or phosphites, which contain optionally substituted aliphatic hydrocarbon radicals as substituents (and in the reaction are converted into phosphoric acid triesters), such as tri-lower alkyl phosphites, usually in the form of corresponding alcohol adduct compounds, such as trimethyl phosphite, or phosphorous acid triamides, which contain optionally substituted aliphatic hydrocarbon radicals as substituents such as hexa-lower alkyl phosphorous acid triamides, for example hexamethyl phosphorus acid triamide, the latter preferably in the form of a methanol adduct, or suitable nitrogen bases (which in the reaction are converted into the corresponding N-oxides), such as heterocyclic nitrogen bases of aromatic character, for example bases of the pyridine type and especially pyridine itself. The splitting of the usually unisolated ozonide is normally carried out under the conditions used for its manufacture, that is to say, in the presence of a suitable solvent or solvent mixture, and while cooling or heating gently, wherein preferably temperatures of approximately $-10°$ C. to approximately $+25°$ C. are used and the reaction usually terminates at room temperature.

Stage 2.6

A compound of the formula IVa is obtained by solvolysing a compound of the formula XII and, if desired, converting a group $R_1$ in a compound so obtained into a different group $R_1$, and/or, if desired, converting an optionally substituted methylidene group $Z'$ into an oxo group $Z$.

The solvolysis may be carried out by hydrolysis or preferably alcoholysis, wherein the reaction is usually carried out with a lower alkanol, for example methanol or ethanol. The alcoholysis is preferably carried out in the presence of water and an organic solvent, such as a lower alkanecarboxylic acid-lower alkyl ester, for example ethyl acetate, preferably at room temperature, if necessary while cooling or heating. The α-ketocarboxylic acid of the formula XIII does not necessarily have to be isolated. If, for example, the ozonide is split in the presence of a solvolysing agent, such as, for example, water, a compound of the formula IVa can be obtained directly.

In the compounds IV to XII, II and IVa, a group $R_1$ or $R_2^4$ can be converted according to methods known per se into a different $R_1$ or $R_2^4$ group respectively, wherein it is possible to use the same methods as are given for converting these substituents in the compounds of the formula I.

In the compounds IV to VI and II, an optionally substituted methylidene group $Z'$ may be converted into an oxo group $Z$ by ozonisation and subsequent reduction of the ozonide formed, according to the process described in stage 2.5.

The invention likewise includes the new intermediate products, such as those of the formulae IV to XIII and especially of the formula II, and the processes for their production.

The pharmacologically usable compounds of the invention may be used, for example, for the production of pharmaceutical preparations that contain an effective amount of the active substance together or in admixture with inorganic or organic, solid or liquid, pharmaceutically usuable carrier substances that are suitable for enteral or parenteral administration. For example, tablets or gelatin capsules that contain the active substance together with diluents, for example lactose, dextrose, sucrose, mannitol, sorbitol, cellulose and/or glycine, and lubricants, for example silica, talcum, stearic acid or salts thereof, such as magnesium or calcium stearate, and/or polyethyleneglycol; tablets also contain binders, for example magnesium aluminium silicate, starches such as maize, wheat, rice or arrowroot starch, gelatin, tragacanth, methylcellulose, sodium carboxymethylcellulose and/or polyvinylpyrrolidone, and, if desired, disintegrating agents, for example starches, agar, alginic acid or a salt thereof, such as sodium alginate, and/or effervescing mixtures, or adsorbents, dyestuffs, flavouring substances and sweeteners. Also, the new pharmacologically active compounds can be used in the form of injectable, for example intravenously administrable, preparations or in the form of infusion solutions. Solutions of this type are preferably isotonic aqueous solutions or suspensions, wherein these can be produced before use for example from lyophilised preparations that contain the active substance alone or together with a carrier material, for example mannitol. The pharmaceutical preparations may be sterilised and/or contain auxiliary substances, for example preservatives, stabilisers, wetting agents and/or emulsifiers, solubilisers, salts for regulating the osmotic pressure and/or buffers. The pharmaceutical preparations of the invention which, if desired, may contain other pharmacologically valuable substances are produced in a manner known per se, for example by means of conventional mixing, granulating, pill-coating, dissolving or lyophilising processes and contain from approximately 0.1% to 100%, especially from approximately 1% to approximately 50%, in the case of the lyophilisate up to 100%, of the active substance.

Referring to the present description, organic radicals referred to as "lower", unless expressly defined, contain up to 7, preferably up to 4, carbon atoms; acyl radicals contain up to 20, preferably up to 12, and primarily up to 7, carbon atoms.

The following Examples serve to illustrate the invention; temperatures are in degrees Centigrade. The following abbreviations are used: TLC=thin layer chromatogram over silica gel; sh=shoulder.

EXAMPLE 1

(4R,S)-4Acetylthio-2-oxoazetidine

A solution of 0.12 ml of thioacetic acid in 1.6 ml of 1 N sodium hydroxide solution is added dropwise, at room temperature, to a solution of 138 mg (1.07 mmol) of (4R,S)-4-acetoxyazetidin-2-one in 0.4 ml of water and 0.1 ml of acetone, and the mixture is stirred at the same temperature overnight. The reaction mixture is exhaustively extracted with methylene chloride. The combined organic phases are dried over sodium sulphate and concentrated in vacuo. The residue is chromatographed over silica gel with toluene/ethyl acetate (4:1 to 3:2) and yields the title compound with the following physico-chemical properties:

TLC: $R_f$=0.29 (toluene/ethyl acetate 2:3); IR spectrum ($CH_2Cl_2$): absorption bands at 2.95, 5.6, 5.9 and 8.85μ.

EXAMPLE 2

2-[(4R,S)-4-Acetylthio-2-oxo-1-azetidinyl]-2-hydroxyacetic acid p-nitrobenzyl ester A solution of 12.9 g of 2-ethoxy-2-hydroxyacetic acid p-nitrobenzyl ester in a mixture of 240 ml of toluene and 60 ml of dimethylformamide is added at room temperature to 3.3 g (22.75 mmol) of (4R,S)-4-acetylthio-2-oxoazetidine. After adding freshly dried molecular sieves, the mixture is stirred under nitrogen overnight at room temperature and subsequently for 2 hours at 50°. The molecular sieves are filtered off, washed with toluene and the filtrate and washing liquid are concentrated together in vacuo. The residue is dried under high vacuum and chromatographed over silica gel with toluene/ethyl acetate (9:1). After elution of the unreacted 2-ethoxy-2-hydroxyacetic acid p-nitrobenzyl ester, the title compound having the following physico-chemical properties is eluted:

TLC: $R_f$=0.31 (toluene/ethyl acetate 2:3); IR spectrum ($CH_2Cl_2$): absorption bands at 2.8, 5.6, 5.7, 5.87, 6.55 and 7.4μ.

EXAMPLE 3

2-[(4R,S)-4-Acetylthio-2-oxo-1-azetidinyl]-2-triphenylphosphoranylideneacetic acid p-nitrobenzyl ester (a) A solution of 2 g of 2-[(4R,S)-4-acetylthio-2-oxo-1-azetidinyl]-2-hydroxyacetic acid p-nitrobenzyl ester in 40 ml of absolute dioxan is added to a solution of 5.5 g of poly-Hünig base in 20 ml of absolute dioxan that has already been stirred for 30 minutes. After adding a solution of 1.87 ml (3.5 equivalents) of thionyl chloride in 30 ml of absolute dioxan, the reaction mixture is stirred for 5 hours at room temperature under nitrogen. The poly-Hünig base is filtered off and the filtrate is concentrated in vacuo.

(b) The crude 2-[(4R,S)-4-acetylthio-2-oxo-1-azetidinyl]-2-chloroacetic acid p-nitrobenzyl ester obtained is dissolved in 107 ml of absolute dioxan, 7 g of poly-H/ünig base and 2.85 g of triphenylphosphine are added and the mixture is stirred under nitrogen for 15 hours at 50°. The poly-H/ünig base is filtered off, washed with dioxan and the filtrate and washing liquid are concentrated together in vacuo. The residue is chromatographed over silica gel with toluene/ethyl acetate and yields the title compound having the following physico-chemical properties:

TLC: $R_f$=0.24 (toluene/ethyl acetate 2:3); IR spectrum ($CH_2Cl_2$): absorption bands at 5.67, 5.9, 6.15, 6.55, 7.42, 9.05 and 9.25μ.

(c) The same title compound may alternatively be obtained by stirring 0.44 mmol of 2-[(4R,S)-4-acetylthio-2-oxo-1-azetidinyl]-2-hydroxyacetic acid p-nitrobenzyl ester in a mixture of 2 ml of methylene chloride and 0.2 ml of carbon tetrachloride with 1 mmol of triphenylphosphine for 4 hours at room temperature and for 30 minutes at 40° C., diluting the reaction mixture with methylene chloride, washing with aqueous sodium bicarbonate solution, drying over sodium sulphate, concentrating in vacuo and chromatographing the residue over silica gel with toluene/ethyl acetate (2:3).

EXAMPLE 4

(5R,S)-2-Methyl-2-penem-3-carboxylic acid p-nitrobenzyl ester

A catalytic amount of hydroquinone is added to a solution of 100 mg (0.167 mmol) of 2-[(4R,S)-4-acetylthio-2-oxo-1-azetidinyl]-2-triphenylphosphoranylideneacetic acid p-nitrobenzyl ester in 50 ml of absolute toluene, and the mixture is stirred overnight at 90° under nitrogen. The solvent is evaporated off in vacuo and the residue is chromatographed over silica gel with toluene/ethyl acetate (19:1). The title compound is obtained in the form of yellowish crystals having the following physico-chemical properties:

Melting point: 130°–132°; TLC: $R_f$=0.54 (toluene-/ethyl acetate 2:3); UV spectrum (ethanol): $\lambda_{max}$=308 nm ($\epsilon$=10036), 262 nm ($\epsilon$=13090); IR spectrum ($CH_2Cl_2$): absorption bands at 5.57, 5.82, 6.3, 6.55, 7.4, 7.6 and 8.3μ; NMR spectrum (in $CDCl_3$/100 Mc, in ppm): 8.25=2H, m; 7.65=2H, m; 5.65=1H, q; 5.35=2H, m; 3.4–3.9=2H, m; 2.4–3H, s.

EXAMPLE 5

(5R,S)-2-Methyl-2-penem-3-carboxylic acid (a) 2 ml of 0.2 M aqueous sodium bicarbonate solution and 100 mg of 10% palladium/carbon catalyst are added to a solution of 50 mg of (5R,S)-2-methyl-2-penem-3-carboxylic acid p-nitrobenzyl ester in 3 ml of absolute ethyl acetate and the mixture is stirred at normal pressure for 35 minutes under hydrogen. The hydrogenated mixture is filtered off from the catalyst over diatomaceous earth, the residue is washed with 0.7 ml of 0.2 M sodium bicarbonate solution and ethyl acetate, and the filtrate and washing liquid are freed of ethyl acetate in vacuo. The remaining aqueous solution is acidified with 5 ml of 5% aqueous citric acid solution and exhaustively extracted with methylene chloride. The combined organic phases are dried over sodium sulphate, filtered, concentrated in vacuo and dried under high vacuum. The title compound obtained has the following physico-chemical properties:

IR spectrum ($CH_2Cl_2$): absorption bands at 5.57 and 5.95μ; NMR spectrum (DMSO d6/100 Mc, in ppm): 5.65=1H, q; 3.3–3.9=2H, m (+$H_2O$); 2.28=3H, s.

(b) 28 ml of 0.2 M aqueous sodium bicarbonate solution and 1 g of 10% palladium/carbon catalyst are added to a solution of 700 mg (2.18 mmol) of (5R,S)-2-methyl-2-penem-3-carboxylic acid p-nitrobenzyl ester in 42 ml of absolute ethyl acetate and the mixture is stirred at normal pressure for 90 minutes under hydrogen. The hydrogenated mixture is filtered off from the catalyst over diatomaceous earth, the residue is washed with 0.2 M sodium bicarbonate solution and ethyl acetate, and the filtrate and washing liquid are combined. The aqueous phase is separated off, washed with methylene chloride, acidified with 5 ml of 5% aqueous citric acid solution and exhaustively extracted with methylene chloride. The combined organic phases are dried over sodium sulphate, filtered, concentrated in vacuo and dried under high vacuum. The title compound obtained is crystallised from diethyl ether/acetone and has the following physico-chemical properties:

Melting point: 140°–167° (undefined, with decomposition); TLC: $R_f$=0.17 (toluene/ethyl acetate 3:2+5% acetic acid), IR spectrum (KBr): absorption bands at 3.4, 3.6, 3.95, 5.62, 6.0, 6.37, 7.0, 7.6, 7.85 and 8.15μ; NMR spectrum as above.

In a similar manner it is possible starting from a corresponding optically active (5R)- or (5S)-compound, to produce the optically active (5R)- and (5S)-2-methyl-2-penem-3-carboxylic acid respectively, which can also be obtained by resolving the racemic compound with an optically active base.

EXAMPLE 6

Sodium salt of (5R,S)-2-methyl-2-penem-3-carboxylic acid

A solution of 50 mg of (5R,S)-2-methyl-2-penem-3-carboxylic acid in the equivalent amount of aqueous sodium bicarbonate solution is concentrated in vacuo and dried under high vacuum.

EXAMPLE 7

(4R,S)-4-Phenylacetylthio-2-oxoazetidine

A solution of 5 g (33 mmol) of phenylthioacetic acid in 33 ml of 1 N aqueous sodium hydroxide solution is added dropwise, at room temperature, to a solution of 4.24 g (33 mmol) of (4R,S)-4-acetoxyazetidin-2-one in 20 ml of water and the mixture is stirred overnight at the same temperature. The precipitated title compound is filtered off, and recrystallised twice from ethylene chloride/hexane. Melting point: 78°; IR spectrum ($CH_2Cl_2$): absorption bands at 3.0, 5.65, 5.95, 6.73, 7.15, 7.5, 7.87, 8.65, 9.21, 10.25, 10.6 and 11.15μ.

EXAMPLE 8

2-[(4R,S)-4-Phenylacetylthio-2-oxo-1-azetidinyl]-2-hydroxyacetic acid p-nitrobenzyl ester 2.87 g (11.24 mmol) of 2-ethoxy-2-hydroxyacetic acid p-nitrobenzyl ester is added at room temperature to a solution of 1.244 g (5.62 mmol) of (4R,S)-4-phenylacetylthio-2-oxoazetidine in 42 ml of toluene and 11 ml of dimethylformamide. After the addition of freshly dried molecular sieves A4, the mixture is stirred at room temperature overnight under nitrogen. The molecular sieves are filtered off and the filtrate is concentrated in vacuo. The residue is dried under high vacuum and chromatographed over silica gel with toluene/ethyl acetate (9:1 and 4:1). After eluting the unreacted 2-ethoxy-2-hydroxyacetic acid p-nitrobenzyl ester, the title compound having the following physico-chemical properties is eluted:

TLC: $R_f$=0.38 (toluene/ethyl acetate 1:1); IR spectrum ($CH_2Cl_2$): absorption bands at 2.85, 2.95, 5.6, 5.7 (sh), 5.9, 6.55 and 7.4μ. This product still contains some 2-ethoxy-2-hydroxyacetic acid p-nitrobenzyl ester but can be used in the following reaction without further purification.

EXAMPLE 9

2-[(4R,S)-4-Phenylacetylthio-2-oxo-1-azetidinyl]-2-triphenylphosphoranylideneacetic acid p-nitrobenzyl ester (a) A solution of 522 mg (1.21 mmol) of 2-[(4R,S)-4-phenylacetylthio-2-oxo-1-azetidinyl]-2-hydroxyacetic acid p-nitrobenzyl ester in 10 ml of absolute dioxan is added to a solution of 1.5 g of poly-Hünig base in 5 ml of absolute dioxan that has already been stirred for 30 minutes. After adding a solution of 0.304 ml (3.5 equivalents) of thionyl chloride in 8 ml of absolute dioxan, the reaction mixture is stirred for 3 hours at room temperature under nitrogen. The poly-Hünig base is filtered off and the filtrate is concentrated in vacuo. The 2-[(4R,S)-

4-phenylacetylthio-2-oxo-1-azetidinyl]-2-chloroacetic acid p-nitrobenzyl ester is used in the following reaction without further purification.

TLC: $R_f$=0.62 (toluene/ethyl acetate 1:1); IR spectrum (in $CH_2Cl_2$): absorption bands at 5.61, 5.70, 6.25, 6.55, 7.45 and 9.0µ.

(b) The crude 2-[(4R,S)-4-phenylacetylthio-2-oxo-1-azetidinyl]-2-chloroacetic acid p-nitrobenzyl ester obtained is dissolved in 25 ml of absolute dioxan, 481 mg of triphenylphosphine and 2 g of poly-Hünig base are added and the mixture is stirred overnight at 50° under nitrogen. The poly-Hünig base is filtered off, washed with dioxan and the filtrate and washing liquid are concentrated together in vacuo. The residue is chromatographed over silica gel with toluene/ethyl acetate (9:1, 4:1 and 1:1) and yields the title compound with the following physico-chemical properties:

TLC: $R_f$=0.27 (toluene/ethyl acetate 1:1); IR spectrum ($CH_2Cl_2$): absorption bands at 3.33, 5.70, 5.90, 6.15, 6.57, 6.68, 6.96, 7.29, 7.42, 7.90, 8.25, 8.40, 9.05, 9.25, 9.70, 9.85 and 10.0µ.

EXAMPLE 10

(5R,S)-2-Benzyl-2-penem-3-carboxylic acid p-nitrobenzyl ester

A catalytic amount of hydroquinone is added to a solution of 268 mg (0.167 mmol) of 2-[(4R,S)-4-phenylacetylthio-2-oxo-1-azetidinyl]-2-triphenylphosphoranylideneacetic acid p-nitrobenzyl ester in 75 ml of absolute toluene and the mixture is stirred under nitrogen for 36 hours at 90°. The solvent is evaporated off in vacuo and the residue is chromatographed over silica gel with toluene/ethyl acetate (19:1). The title compound is obtained in the form of colourless crystals having the following physico-chemical properties:

Melting point: 115° (from methylene chloride/diethyl ether). IR spectrum ($CH_2Cl_2$): absorption bands at 3.33, 3.45, 5.6, 5.83, 6.25, 6.36, 6.58, 7.45, 7.65, 8.4, 8.85, 9.45, 9.95 and 11.75µ; NMR spectrum (in $CDCl_3$/100 Mc, in ppm): 8.18, 2H, d, J=9 Hz; 7.58, 2H, d, J=9 Hz; 7.24, 5H, s; 5.57, 1H, qu, $J_{cis}$=4 Hz, $J_{trans}$=2 Hz; 5.35, 2H, AB; 4.17, 2H, AB; 3.59, 2H, ABX; $J_{AX}$=2 Hz, $J_{BX}$=4 Hz.

EXAMPLE 11

(5R,S)-2-Benzyl-2-penem-3-carboxylic acid 3 ml of a 0.2 M aqueous solution of sodium bicarbonate solution and 150 mg of 10% palladium/carbon catalyst are added to a solution of 78 mg of (5R,S)-2-benzyl-2-penem-3-carboxylic acid p-nitrobenzyl ester in 4.5 ml of absolute ethyl acetate and the mixture is stirred at normal pressure for 30 minutes under hydrogen. The hydrogenated mixture is filtered off from the catalyst over diatomaceous earth and the residue is washed with 2 ml of 0.2 M sodium bicarbonate solution and ethyl acetate. The aqueous solution is separated from the filtrate, acidified with 0.1 M aqueous citric acid solution and exhaustively extracted with methylene chloride. The combined methylene chloride extracts are dried over sodium sulphate, filtered, concentrated in vacuo and dried under high vacuum. The title compound is obtained in the form of colourless needles and has the following physico-chemical properties:

Melting point 113°-132°; IR spectrum ($CH_2Cl_2$): absorption bands at 5.6, 6.0, 6.42, 7.45, 7.87 and 8.43µ.

EXAMPLE 12

(4R,S)-4-(2-Furoylthio)-2-oxoazetidine

A solution of 6.4 g (50.7 mmol) of furan-2-thiocarboxylic acid in 51 ml sodium hydroxide solution is added dropwise at room temperature under nitrogen to a solution of 5.15 g (35 mmol) of (4R,S)-4-acetoxyazetidin-2-one in 20 ml of water and the mixture is stirred at the same temperature for 4 to 6 hours. The reaction mixture is exhaustively extracted with methylene chloride. The combined organic phases are dried over sodium sulphate and concentrated in vacuo. The residue is chromatographed over silica gel with toluene/ethyl acetate (4:1) and yields the title compound having a melting point of 94°-95°.

TLC: $R_f$=0.34 (toluene/ethyl acetate 2:3); IR spectrum ($CH_2Cl_2$): absorption bands at 2.97, 5.6, 6.05, 6.37 and 6.85µ.

EXAMPLE 13

2-[(4R,S)-4-(2-Furoylthio)-2-oxo-1-azetidinyl]-2-hydroxyacetic acid p-nitrobenzyl ester A solution of 7.6 g of 2-ethoxy-2-hydroxyacetic acid p-nitrobenzyl ester in 150 ml of toluene and 38 ml of dimethylformamide is added at room temperature to 2.4 g of (4R,S)-4-(2-furoylthio)-2-oxoazetidine. After adding freshly dried molecular sieves, the mixture is stirred under nitrogen for 15 hours at room temperature and then for 2 hours at 50°. The molecular sieves are filtered off, washed with toluene and the filtrate and washing liquid are concentrated together in vacuo. The residue is chromatographed over 200 g of silica gel with toluene/ethyl acetate (9:1 to 8:2). After elution of the unreacted 2-ethoxy-2-hydroxyacetic acid p-nitrobenzyl ester, the title compound with the following physicochemical properties is eluted:

TLC: $R_f$=0.33 (toluene/ethyl acetate 2:3); IR spectrum ($CH_2Cl_2$): absorption bands at 2.87, 5.52, 5.6, 6.05; 6.55; 6.85 and 7.42µ.

EXAMPLE 14

2-[(4R,S)-4-(2-Furoylthio)-2-oxo-1-azetidinyl]-2-triphenylphosphoranylideneacetic acid p-nitrobenzyl ester (a) A solution of 4.9 g of 2-[(4R,S)-4-(2-furoylthio)-2-oxo-1-azetidinyl]-2-hydroxyacetic acid p-nitrobenzyl ester in 90 ml of absolute dioxan is added to a solution of 18 g of poly-Hünig base in 45 ml of absolute dioxane that has already been stirred for 30 minutes. After adding a solution of 3.45 ml of thionyl chloride in 30 ml of absolute dioxan, the reaction mixture is stirred for one hour at room temperature under nitrogen. The poly-Hünig base is filtered off and the filtrate is concentrated in vacuo. IR spectrum (in $CH_2Cl_2$): absorption bands at 5.57, 6.02, 6.55, 7.4, 8.9 and 11.4µ.

(b) The crude 2-[(4R,S)-4-(2-furoylthio)-2-oxo-1-azetidinyl]-2-chloroacetic acid p-nitrobenzyl ester obtained is dissolved in 216 ml of absolute dioxan, stirred together with 18 g of poly-Hünig base for 30 minutes under nitrogen and, after adding 6.15 g of triphenylphosphine, is stirred for a further 15 hours at 50° under nitrogen. The poly-Hünig base is filtered off, washed with dioxan and the filtrate and washing liquid are concentrated together in vacuo. The residue is chromatographed over 200 g of silica gel with toluene/ethyl acetate (8:2 and 7:3) and yields the title compound with the following physico-chemical properties:

TLC: $R_f=0.35$ (toluene/ethyl acetate 2:3); IR spectrum (CH$_2$Cl$_2$): absorption bands at 5.67, 6.02, 6.15, 6.57, 7.42, 9.02, 9.25 and 9.85$\mu$.

EXAMPLE 15

(5R,S)-2-Fur-2-yl-2-penem-3-carboxylic acid p-nitrobenzyl ester

A catalytic amount of hydroquinone is added to a solution of 1 g (1.54 mmol) of 2-[(4R,S)-4-(2-furoylthio)-2-oxo-1-azetidinyl]-2-triphenylphosphoranylideneacetic acid p-nitrobenzyl ester in 450 ml of absolute toluene and the mixture is stirred under nitrogen for 48 hours at 90°. The solvent is evaporated off in vacuo and the residue is chromatographed over 50 g of silica gel with toluene/ethyl acetate (19:1). The title compound is obtained in the form of yellowish crystals having the following physico-chemical properties:

Melting point: 161°-163° (diethyl ether/methylene chloride); TLC: $R_f=0.64$ (toluene/ethyl acetate 2:3); IR spectrum (CH$_2$Cl$_2$): absorption bands at 5.57, 5.85, 6.55, 7.42, 7.62, 8.2, 8.35 and 8.5$\mu$; NMR spectrum (in CDCl$_3$/100 Mc, in ppm): 8.22=2H, m; 7.75-7.5=4H, m; 6.55=1H, dd; 5.68=1H, dd; 5.37, 2H, m; 3.7=2H, m.

EXAMPLE 16

(5R,S)-2-Fur-2-yl-2-penem-3-carboxylic acid 4 ml of 0.2 N aqueous sodium bicarbonate solution and 200 mg of 10% palladium/carbon catalyst are added to a solution of 100 mg of (5R,S)-2-fur-2-yl-2-penem-3-carboxylic acid p-nitrobenzyl ester in 6 ml of absolute ethyl acetate and the mixture is stirred at normal pressure for 75 minutes under hydrogen. The hydrogenated mixture is filtered off from the catalyst over diatomaceous earth, the residue is washed with 0.2 N sodium bicarbonate solution and ethyl acetate, and the filtrate and washing liquid are combined and the phases separated. The aqueous phase is washed with methylene chloride, acidified with 5% aqueous citric acid solution and extracted with methylene chloride. The methylene chloride phases are dried over sodium sulphate, filtered, concentrated in vacuo and dried under high vacuum. The title compound obtained has the following physico-chemical properties:

TLC: $R_f=0.34$ (toluene/ethyl acetate/acetic acid 60:40:5); IR spectrum (KBr): absorption bands at 3.35-3.55, 5.6, 5.95, 6.57, 7.07, 7.7, 7.82, 8.15, 8.35$\mu$; NMR spectrum (DMSO d6/100 Mc, in ppm): 7.9, 1H, m; 7.6, 1H, m; 6.74, 1H, m; 5.75, 1H, m; 4.0-3.4, 2H, m.

EXAMPLE 17

(4R,S)-4-(3-Dimethylaminobenzoylthio)-2-oxoazetidine

A solution of 864 mg (4.77 mmol) of 3-dimethylaminothiobenzoic acid in 4.77 ml of 1 N sodium hydroxide solution and 5 ml of tetrahydrofuran is added dropwise at 0° to a solution of 616 mg (4.77 mmol) of (4R,S)-4-acetoxyazetidin-2-one in 13 ml of water and the mixture is stirred overnight at room temperature. The reaction mixture is extracted with 50 ml of methylene chloride. The organic phase is washed with water, dried over sodium sulphate and concentrated in vacuo. The residue is chromatographed over silica gel with toluene/ethyl acetate (9:1, 4:1 and 2:1) and yields the title compound which after recrystallising from methylene chloride/pentane is obtained in the form of green-yellow crystals melting at 117°.

IR spectrum (CH$_2$Cl$_2$): absorption bands at 2.95, 3.5, 5.63, 6.03, 6.25, 6.68, 7.0, 7.40, 8.28, 8.62, 10.22, 10.82 and 11.10$\mu$.

EXAMPLE 18

2-[(4R,S)-4-(3-Dimethylaminobenzoylthio)-2-oxo-1-azetidinyl]-2-hydroxyacetic acid p-nitrobenzyl ester 714 mg (2.8 mmol) of 2-ethoxy-2-hydroxyacetic acid p-nitrobenzyl ester are added at room temperature to a solution of 305 mg (1.38 mmol) of (4R,S)-(3-dimethylaminobenzoylthio)-2-oxoazetidine in a mixture of 8 ml of toluene and 2 ml of dimethylformamide. After adding freshly dried molecular sieves A4, the mixture is stirred overnight at room temperature under nitrogen. The molecular sieves are filtered off, washed with toluene and the filtrate and washing liquid are concentrated together in vacuo. The residue is chromatographed over silica gel with toluene and toluene/ethyl acetate (9:1 and 4:1). After eluting the unreacted 2-ethoxy-2-hydroxyacetic acid p-nitrobenzyl ester, the title compound is eluted; it still contains some 2-ethoxy-2-hydroxyacetic acid p-nitrobenzyl ester but can be used in the subsequent reaction without further purification:

TLC: $R_f=0.33$ (toluene/ethyl acetate 1:1); IR spectrum (CH$_2$Cl$_2$): absorption bands at 2.86, 3.42, 5.62, 5.69, 6.03, 6.23, 6.54, 7.41, 8.25, 9.15, 10.20, 10.83 and 11.22$\mu$. Recrystallisation from methylene chloride/diethyl ether yields the pure title compound in the form of red-yellow platelets melting at 148°.

EXAMPLE 19

2-[(4R,S)-4-(3-Dimethylaminobenzoylthio)-2-oxo-1-azetidinyl]-2-chloroacetic acid p-nitrobenzyl ester A solution of 699 mg of 2-[(4R,S)-4-(3-dimethylaminobenzoylthio)-2-oxo-1-azetidinyl]-2-hydroxyacetic acid p-nitrobenzyl ester in 10 ml of absolute dioxan is added to a solution of 2 g of poly-Hünig base in 7.5 ml of absolute dioxan that has already been stirred for 30 minutes. After slowly adding 0.38 ml (3.5 equivalents) of thionyl chloride, the reaction mixture is stirred for 1.5 hours at room temperature under nitrogen. The poly-Hünig base is filtered off and the filtrate is concentrated in vacuo. The title compound obtained is used in the subsequent reaction without further purification.

TLC: $R_f=0.62$ (toluene/ethyl acetate 1:1); IR spectrum (in CH$_2$Cl$_2$): absorption bands at 3.4, 5.62, 5.67, 6.0, 6.25, 6.55, 6.68, 7.45, 7.65, 8.30, 8.50, 9.0, 10.4, 10.85, 11.75$\mu$.

EXAMPLE 20

2-[(4R,S)-4-(3-Dimethylaminobenzoylthio)-2-oxo-1-azetidinyl]-2-triphenylphosphoranylideneacetic acid p-nitrobenzyl ester 2 g of poly-Hünig base and 614 mg of triphenylphosphine are added to a solution of 747 mg of the obtained crude 2-[(4R,S)-4-(3-dimethylaminobenzoylthio)-2-oxo-1-azetidinyl]-2-chloroacetic acid p-nitrobenzyl ester in 30 ml of absolute dioxan, and the mixture is stirred overnight at 50° under nitrogen. The poly-Hünig base is filtered off and the filtrate is concentrated in vacuo. The residue is taken up in methylene chloride, washed with aqueous sodium bicarbonate solution, dried over sodium sulphate and concentrated in vacuo. The residue is chromatographed over silica gel with toluene/ethyl acetate (9:1 and 4:1) and yields the title compound in the form of a green-yellow oil having the following physico-chemical properties:

TLC: $R_f=0.23$ (toluene/ethyl acetate 1:1); IR spectrum ($CH_2Cl_2$): absorption bands at 3.45, 5.69, 6.02, 6.23, 6.57, 6.68, 6.97, 7.42, 8.28, 9.03, 9.25 and 10.83μ.

EXAMPLE 21

(5R,S)-2-(3-Dimethylaminophenyl)-2-penem-3-carboxylic acid p-nitrobenzyl ester

A catalytic amount of hydroquinone is added to a solution of 448 mg (0.64 mmol) of 2-[(4R,S)-4-(3-dimethylaminobenzoylthio)-2-oxo-1-azetidinyl]-2-triphenylphosphoranylideneacetic acid p-nitrobenzyl ester in 100 ml of absolute toluene and the mixture is stirred for 90 hours at 90° under nitrogen. The solvent is evaporated off in vacuo and the residue is chromatographed over silica gel with toluene/ethyl acetate (19:1). The title compound is obtained in the form of colourless crystals having the following physico-chemical properties:

Melting point 77° (from methylene chloride/diethyl ether/pentane);

TLC: $R_f=0.55$ (toluene/ethyl acetate 1:1); IR spectrum ($CH_2Cl_2$): absorption bands at 3.45, 5.6, 5.86, 6.25, 6.62, 6.72, 7.40, 7.68, 8.39, 8.45, 8.53, 9.10, 9.75, 10.05 and 11.8μ; NMR spectrum (in $CDCl_3$/100 Mc, in ppm): 8.06, 2H, d, J=10 Hz; 7.25, 4H, m; 6.75, 2H, d, J=10 Hz; 5.75, 1H, dd, $J_1=4$ Hz, $J_2=2$ Hz; 5.18, 2H, AB, J=14 Hz; 3.9, 1H, dd, $J_1=16$ Hz, $J_2=4$ Hz; 3.56, 1H, dd, $J_1=16$ Hz, $J_2=2$ Hz; 2.88, 6H, s.

EXAMPLE 22

(5R,S)-2-(3-Dimethylaminophenyl)-2-penem-3-carboxylic acid 3 ml of 0.2 M aqueous sodium bicarbonate solution and 150 mg of 10% palladium/carbon catalyst are added to a solution of 65 mg (0.15 mmol) of (5R,S)-2-(3-dimethylaminophenyl)-2-penem-3-carboxylic acid p-nitrobenzyl ester in 4 ml of absolute ethyl acetate and the mixture is stirred for 60 minutes at normal pressure under hydrogen. The hydrogenated mixture is filtered off from the catalyst over diatomaceous earth, the residue is washed with 2 ml of 0.2 M sodium bicarbonate solution and ethyl acetate. The aqueous phase is separated from the filtrate and washed with diethyl ether. The washed aqueous solution is acidified with 5% aqueous citric acid solution and exhaustively extracted with methylene chloride. The combined methylene chloride extracts are dried over sodium sulphate, filtered and concentrated in vacuo. The title compound obtained has the following physico-chemical properties: IR spectrum ($CH_2Cl_2$): absorption bands at 3.4, 5.57, 5.77, 5.95, 6.25, 6.70, 7.40, 8.08, 8.28, 8.80, 9.05 and 10.05μ.

EXAMPLE 23

(4R,S)-4-(3-Methoxycarbonylpropionylthio)-2-oxoazetidine

A solution of 1.11 g (7.48 mmol) of 1-thiosuccinic acid 4-monomethyl ester in 7.48 ml of 1 N sodium hydroxide solution is added dropwise at room temperature to a solution of 966 mg (7.48 mmol) of (4R,S)-4-acetoxyazetidin-2-one in 5 ml of water. The reaction solution is adjusted to a pH of 8 by the addition of 1 N sodium hydroxide solution and exhaustively extracted with methylene chloride. The combined organic phases are dried over sodium sulphate and concentrated in vacuo. The residue is chromatographed over silica gel with toluene/ethyl acetate (9:1, 4:1 and 7:3) and yields the title compound with the following physico-chemical properties:

TLC: $R_f=0.23$ (toluene/ethyl acetate 1:1); IR spectrum ($CH_2Cl_2$): absorption bands at 2.95, 3.40, 5.6, 5.77, 5.88, 6.95, 7.10, 7.30, 7.42, 8.10, 8.30, 8.60, 9.35, 10.20, 10.55 and 11.15μ.

EXAMPLE 24

2-[4R,S)-4-(3-Methoxycarbonylpropionylthio)-2-oxo-1-azetidinyl]-2-hydroxyacetic acid p-nitrobenzyl ester A solution of 625 mg (2 equivalents) of 2-ethoxy-2-hydroxyacetic acid p-nitrobenzyl ester in 8 ml of toluene and 2 ml of dimethylformamide is added at room temperature to 266 mg (1.23 mmol) of (4R,S)-4-(3-methoxycarbonylpropionylthio)-2-oxoazetidine. After adding freshly dried molecular sieves A4, the mixture is stirred overnight at room temperature under nitrogen. The molecular sieves are filtered off and the filtrate is concentrated in vacuo. The residue is dried under high vacuum and chromatographed over silica gel with toluene/ethyl acetate (9:1, 4:1 and 7:3). After eluting the unreacted 2-ethoxy-2-hydroxyacetic acid p-nitrobenzyl ester, the title compound with the following physico-chemical properties is eluted:

TLC: $R_f=0.20$ (toluene/ethyl acetate 1:1); IR spectrum ($CH_2Cl_2$): absorption bands at 2.85, 3.4, 5.65, 5.75, 5.95, 6.60, 7.45, 8.30 and 9.15μ.

EXAMPLE 25

2-[(4R,S)-4-(3-Methoxycarbonylpropionylthio)-2-oxo-1-azetidinyl]-2-triphenylphosphoranylideneacetic acid p-nitrobenzyl ester (a) A solution of 446 mg (1.05 mmol) of 2-[(4R,S)-4-(3-methoxycarbonylpropionylthio)-2-oxo-1-azetidinyl]-2-hydroxyacetic acid p-nitrobenzyl ester in 8 ml of absolute dioxan is added to a solution of 2 g of poly-Hünig base in 7 ml of absolute dioxan. After adding a solution of 0.26 ml (3.5 equivalents) of thionyl chloride in 8 ml of absolute dioxan, the reaction mixture is stirred for 100 minutes at room temperature under nitrogen. The poly-Hünig base is filtered off and the filtrate is concentrated in vacuo. The crude 2-[(4R,S)-4-(3-methoxycarbonylpropionylthio)-2-oxo-1-azetidinyl]-2-chloroacetic acid p-nitrobenzyl ester having the following physico-chemical properties:

TLC: $R_f=0.47$ (toluene/ethyl acetate 1:1); IR spectrum (in $CH_2Cl_2$): absorption bands at 3.40, 5.65, 5.80, 5.95, 6.60, 7.45, 7.65, 8.15, 8.35, 8.50, 9.40, 10.0 and 11.4μ is used in the subsequent reaction without further purification.

(b) The crude 2-[(4-R,S)-4-(3-methoxycarbonylpropionylthio)-2-oxo-1-azetidinyl]-2-chloroacetic acid p-nitrobenzyl ester obtained is dissolved in 25 ml of absolute dioxan, 2 g of poly-Hünig base and 433 mg of triphenylphosphine are added and the mixture is stirred overnight at 50° under nitrogen. The poly-Hünig base is filtered off, washed with dioxan and the filtrate and washing liquid are concentrated together in vacuo. The residue is chromatographed over silica gel with toluene/ethyl acetate (9:1, 4:1 and 1:1) and yields the title compound with the following physico-chemical properties:

TLC: $R_f=0.1$ (toluene/ethyl acetate 1:1); IR spectrum ($CH_2Cl_2$): absorption bands at 3.40, 5.70, 5.95, 6.20, 6.60, 7.00, 7.45, 7.90, 8.30, 9.05 and 9.30μ.

EXAMPLE 26

(5R,S)-2-(2-Methoxycarbonylethyl)-2-penem-3-carboxylic acid p-nitrobenzyl ester

A catalytic amount of hydroxyquinone is added to a solution of 272 mg (0.41 mmol) of 2-[(4R,S)-4-(3-methoxycarbonylpropionylthio)-2-oxo-1-azetidinyl]-2-triphenylphosphoranylideneacetic acid p-nitrobenzyl ester in 100 ml of absolute toluene and the mixture is stirred for two days at 90° under nitrogen. The solvent is evaporated off in vacuo and the residue is chromatographed over silica gel with toluene/ethyl acetate (19:1 and 9:1). The title compound is obtained in the form of colourless crystals melting at 125° (from methylene chloride/diethyl ether);

TLC: $R_f=0.47$ (toluene/ethyl acetate 1:1); IR spectrum ($CH_2Cl_2$): absorption bands at 3.30, 3.45, 5.60, 5.78, 5.85, 6.33, 6.56, 7.45, 7.65, 8.35, 8.80 and 9.50$\mu$; NMR spectrum (in $CDCl_3$/100 Mc, in ppm): 8.28, 2H, d, J=9 Hz; 7.65, 2H, d, J=9 Hz; 5.70, 1H, dd, $J_1=2$ Hz, $J_2=4$ Hz; 5.40, 2H, AB, J=14 Hz; 3.85, 1H, ABX, $J_1=16$ Hz, $J_2=4$ Hz; 3.74, 3H, s; 3.55, 1H, ABX, $J_1=16$ Hz, $J_2=2$ Hz; 3.20, 2H; 2.64, 2H.

EXAMPLE 27

(5R,S)-2-(2-Methoxycarbonylethyl)-2-penem-3-carboxylic acid 3 ml of 2 M aqueous sodium bicarbonate solution and 150 mg of 10% palladium/carbon catalyst are added to a solution of 50 mg of (5R,S)-2-(2-methoxycarbonylethyl)-2-penem-3-carboxylic acid p-nitrobenzyl ester in 3 ml of absolute ethyl acetate, and the mixture is stirred for 60 minutes at normal pressure under hydrogen. The hydrogenated mixture is filtered off from the catalyst over diatomaceous earth, the residue is washed with 2 ml of 2 M sodium bicarbonate solution and ethyl acetate and the aqueous phase is separated from the filtrate and washing liquid. The aqueous solution is washed once with diethyl ether, acidified with 5% aqueous citric acid solution and exhaustively extracted with methylene chloride. The combined methylene chloride extracts are dried over sodium sulphate, filtered, concentrated in vacuo and dried under high vacuum. The title compound obtained has the following physico-chemical properties:

IR spectrum ($CH_2Cl_2$): 3.45, 5.57, 5.75, 5.95, 6.35, 7.0, 7.70, 8.35, 8.50 and 9.50$\mu$; UV spectrum in ethanol: $\nu_{max}$ at 262 and 304 nm.

EXAMPLE 28

(4R,S)-4-Benzoylthio-2-oxoazetidine

A solution of 5.5 g (40 mmol) of thiobenzoic acid in 40 ml of 1 N sodium hydroxide solution is added dropwise at 0° to a solution of 5.15 g (40 mmol) of (4R,S)-4-acetoxyazetidin-2-one in 20 ml of water. The reaction mixture is adjusted to a pH of approximately 7 and stirred overnight. The precipitated title compound is filtered off, washed with cold water until free of alkali and recrystallised from methylene chloride/hexane.

Melting point: 104°–105°; TLC: $R_f=0.56$ (toluene/ethyl acetate 1:1); IR spectrum ($CH_2Cl_2$): absorption bands at 2.92, 5.57, 5.95, 6.20, 6.27, 8.22, 8.45, 10.85 and 11.10$\mu$.

EXAMPLE 29

2-[(4R,S)-4-Benzoylthio-2-oxo-1-azetidinyl]-2-hydroxyacetic acid p-nitrobenzyl ester Freshly dried molecular sieves are added to a solution of 2.35 g (11.38 mmol) of (4R,S)-4-benzoylthio-2-oxoazetidine and 6.45 g of 2-ethoxy-2-hydroxyacetic acid p-nitrobenzyl ester in a mixture of 120 ml of dry toluene and 30 ml of dimethylformamide and the mixture is stirred under nitrogen overnight at room temperature and then for 2 hours at 50°. The molecular sieves are filtered off and the filtrate is concentrated in vacuo. The residue is dried under a high vacuum and chromatographed over silica gel with toluene/ethyl acetate (9:1 and 3:1). After eluting the unreacted 2-ethoxy-2-hydroxyacetic acid p-nitrobenzyl ester, the title compound having the following physico-chemical properties is eluted:

TLC: $R_f=0.56$ (toluene/ethyl acetate 1:1); IR spectrum ($CH_2Cl_2$): absorption bands at 2.85, 5.6, 5.67, 5.95, 6.00, 6.52, 7.40, 8.25, 9.00, 9.15, 10.00 and 11.70$\mu$.

EXAMPLE 30

2-[(4R,S)-4-Benzoylthio-2-oxo-1-azetidinyl]-2-triphenylphosphoranylideneacetic acid p-nitrobenzyl ester (a) A solution of 3 g of 2-[(4R,S)-4-benzoylthio-2-oxo-1-azetidinyl]-2-hydroxyacetic acid p-nitrobenzyl ester in 50 ml of dioxan is added to a mixture of 10 g of poly-Hünig base in 50 ml of dioxan. After adding a solution of 3 ml of thionyl chloride in 50 ml of dioxan, the reaction mixture is stirred for 5 hours at room temperature. The poly-Hünig base is filtered off and the filtrate is concentrated in vacuo.

(b) The crude 2-[(4R,S)-4-benzoylthio-2-oxo-1-azetidinyl]-2-chloroacetic acid p-nitrobenzyl ester obtained is dissolved in 100 ml of dioxan, 10 g of poly-Hünig base and 3.5 g of triphenylphosphine are added and the mixture is stirred for 15 hours at 50°. The poly-Hünig base is filtered off and the filtrate is concentrated in vacuo. The residue is chromatographed over silica gel with toluene/ethyl acetate (9:1 and 3:2) and yields the title compound with the following physico-chemical properties:

TLC: $R_f=0.28$ (toluene/ethyl acetate 1:1); IR spectrum ($CH_2Cl_2$): absorption bands at 5.67, 6.00, 6.15, 6.55, 7.42, 8.30, 9.05, 9.25 and 11.05$\mu$.

EXAMPLE 31

(5R,S)-2-Phenyl-2-penem-3-carboxylic acid p-nitrobenzyl ester

A catalytic amount of hydroquinone is added to a solution of 2.40 g (3.63 mmol) of 2-[(4R,S)-4-benzoylthio-2-oxo-1-azetidinyl]-2-triphenylphosphoranylideneacetic acid p-nitrobenzyl ester in 800 ml of dry toluene and the mixture is stirred for two days at 90°. The solvent is evaporated off in vacuo and the residue is chromatographed over silica gel with toluene/ethyl acetate (19:1). The title compound is obtained in the form of colourless crystals having the following physico-chemical properties:

Melting point 182°–183° (from methylene chloride/diethyl ether); TLC: $R_f=0.67$ (toluene/ethyl acetate 1:1); UV spectrum (ethanol): $\nu_{max}=258$ nm ($\delta=17256$); 327 nm ($\epsilon=8112$); IR spectrum ($CH_2Cl_2$): absorption bands at 5.55, 5.82, 6.55, 7.40, 7.65, 8.35, 8.45, 9.15, 9.85μ; NMR spectrum (in CDCl$_3$/100 Mc, in ppm): 8.10, d, J=9 Hz, 2H; 7.38, m, 7H; 5.78, qu, J=4 Hz, J$_2$=2 Hz, 1H; 5.29, d, J=14 Hz, 1H; 5.12, J=14 Hz, 1H; 3.88, qu, J$_1$=16 Hz, J$_2$=4 Hz, 1H; 3.60, qu, J$_1$=16 Hz, J$_2$=2 Hz, 1H.

EXAMPLE 32

(5R,S)-2-Phenyl-2-penem-3-carboxylic acid

A suspension of 200 mg of (5R,S)-2-phenyl-2-penem-3-carboxylic acid p-nitrobenzyl ester in 12 ml of ethyl acetate and 8 ml of 0.2 M aqueous sodium bicarbonate solution is rinsed with nitrogen, 350 mg of 10% palladium/carbon catalyst are added and the mixture is stirred at normal pressure for 1 hour and 30 minutes under hydrogen. The hydrogenated mixture is filtered off from the catalyst over diatomaceous earth, the residue is washed with 2 ml of water and 5 ml of ethyl acetate, and the filtrate and washing liquid are combined. The aqueous phase is separated, acidified with 5% aqueous citric acid solution and extracted with methylene chloride. The organic phase is dried over sodium sulphate, filtered, concentrated in vacuo and dried under high vacuum. The title compound obtained has the following physico-chemical properties:

Melting point: 127°–128° (from acetone/diethyl ether); UV spectrum (ethanol): λ$_{max}$=323 mμ (ε=7310); 246 mμ (sh) (ε=9570); 235 mμ (ε=10470); IR spectrum (KBr): absorption bands at 3.50, 5.60, 6.00, 6.45, 6.72, 6.97, 7.67, 7.85, 8.27, 9.65, 11.05, 13.10, 13.30, 13.95 and 14.45μ; NMR spectrum (CDCl$_3$/100 Mc, in ppm): 7.42, m, 5H; 5.78, qu, J$_1$=4 Hz, J$_2$=2 Hz, 1H; 3.88, qu, J$_1$=16 Hz, J$_2$=4 Hz, 1H; 3.60, qu, J$_1$=16 Hz, J$_2$=2 Hz, 1H.

EXAMPLE 33

(4R,S)-4-Acetoxyacetylthio-2-oxoazetidine

A precooled solution of 13.4 g (0.1 mol) of acetoxythioacetic acid in 100 ml of 1 N sodium hydroxide solution is added to a solution of 8.5 g (0.065 mol) of (4R,S)-4-acetoxyazetidin-2-one in 50 ml of acetone and the mixture is stirred at room temperature for 3 hours. The reaction mixture is extracted 3 times with 100 ml of methylene chloride each time. The combined organic phases are dried over sodium sulphate and concentrated in vacuo. The residue is chromatographed over silica gel with toluene/ethyl acetate (4:1) and yields the title compound having the following physico-chemical properties:

TLC: R$_f$=0.34 (toluene/ethyl acetate 1:1); IR spectrum (CH$_2$Cl$_2$): absorption bands at 2.95, 5.6, 5.72, 5.9 and 8.20μ.

The acetoxythioacetic acid used as starting material may be produced as follows:

Hydrogen sulphide is conducted through an ice-cold solution of 6.11 g (0.1 mol) of potassium hydroxide in 3 ml of water and 55 ml of ethanol for 45 minutes. A solution of 3.73 g (0.027 mol) of acetoacetyl chloride in 20 ml of dry dioxan is added dropwise over a period of 20 minutes, while stirring, to the so-obtained ice-cold solution of potassium hydrogen sulphide. After stirring for one hour at room temperature, the reaction mixture is extracted with diethyl ether, acidified with cooled 2 N sulphuric acid and extracted with diethyl ether. The organic phase is dried and concentrated and the resulting acetoxythioacetic acid is used in the above reaction without further purification.

EXAMPLE 34

2-[(4R,S)-4-Acetoxyacetylthio-2-oxo-1-azetidinyl]-2-hydroxyacetic acid p-nitrobenzyl ester Freshly dried molecular sieves are added to a solution of 0.44 g (2.17 mmol) of (4R,S)-acetoxyacetylthio-2-oxoazetidine and 1.23 g of 2-ethoxy-2-hydroxyacetic acid p-nitrobenzyl ester in a mixture of 25 ml of toluene and 5 ml of dimethylformamide and the mixture is stirred under nitrogen overnight at room temperature and then for 4 hours at 50°. The molecular sieves are filtered off and the filtrate is concentrated in vacuo. The residue is dried under high vacuum and chromatographed over silica gel with toluene/ethyl acetate (9:1 to 4:1). After eluting the unreacted 2-ethoxy-2-hydroxyacetic acid p-nitrobenzyl ester, the title compound having the following physico-chemical properties is eluted:

TLC: R$_f$=0.31 (toluene/ethyl acetate 1:1); IR spectrum (CH$_2$Cl$_2$): absorption bands at 2.9, 5.6, 5.7, 5.90, 6.25, 6.55, 7.45 and 8.25μ.

EXAMPLE 35

2-[(4R,S)-4-Acetoxyacetylthio-2-oxo-1-azetidinyl]-2-triphenylphosphoranylideneacetic acid p-nitrobenzyl ester (a) A solution of 0.26 ml of thionyl chloride in 5 ml of dioxan is added to a stirred mixture of 0.82 g (2 mmol) of 2-[(4R,S)-4-acetoxyacetylthio-2-oxo-1-azetidinyl]-2-hydroxyacetic acid p-nitrobenzyl ester and 2 g of poly-Hünig base in 20 ml of dry dioxan. The reaction mixture is stirred for one hour at room temperature, the poly-Hünig base is filtered off and the filtrate is concentrated in vacuo.

(b) The crude 2-[(4R,S)-4-acetoxyacetylthio-2-oxo-1-azetidinyl]-2-chloroacetic acid p-nitrobenzyl ester so obtained is dissolved in 20 ml of dry dioxan, 2 g of poly-Hünig base and 0.5 g of triphenylphosphine are added and the mixture is stirred overnight at 50°. The poly-Hünig base is filtered off and the filtrate is concentrated in vacuo. The residue is chromatographed over silica gel with toluene/ethyl acetate (9:1 to 1:1) and yields the title compound with the following physico-chemical properties:

TLC: R$_f$=0.15 (toluene/ethyl acetate 1:1); IR spectrum (CH$_2$Cl$_2$): absorption bands at 5.70, 6.15, 6.55, 6.98, 7.45, 8.20, 8.85 and 9.05μ.

EXAMPLE 36

(5R,S)-Acetoxymethyl-2-penem-3-carboxylic acid p-nitrobenzyl ester

A catalytic amount of hydroquinone is added to a solution of 0.656 g (1 mmol) of 2-[(4R,S)-4-acetoxyacetylthio-2-oxo-1-azetidinyl]-2-triphenylphosphoranylideneacetic acid p-nitrobenzyl ester in 100 ml of dry toluene and the mixture is stirred for 36 hours at 90°. The solvent is evaporated off in vacuo and the residue is chromatographed over silica gel with toluene/ethyl acetate (9:1). The title compound is obtained in the form of colourless crystals having the following physico-chemical properties:

Melting point 127°–128° (from methylene chloride/diethyl ether); TLC: R$_f$=0.53 (toluene/ethyl acetate 1:1); UV spectrum (ethanol): ν$_{max}$=319 nm (ε=9173); 262 nm (ε=11897); IR spectrum (CH$_2$Cl$_2$): absorption bands at 5.60, 5.75, 5.85, 6.30, 6.55, 7.45, 7.60, 8.20μ;

NMR spectrum (in CDCl$_3$/100 Mc, in ppm): 2.14, s, 3H; 3.58, dd, J$_A$=16 Hz, J$_B$=2 Hz, 1H; 3.84, dd, J$_A$=16 Hz, J$_C$=4 Hz, 1H; 5.00–5.60, two overlapping AB quartets, 4H; 5.72, qu, J$_B$=2 Hz; J$_C$=4 Hz, 1H; 7.63, d, J=8 Hz, 2H; 8.22, d, J=8 Hz, 2H.

EXAMPLE 37

(5R,S)-2-Acetoxymethyl-2-penem-3-carboxylic acid 4 ml of 0.2 M aqueous sodium bicarbonate solution and 200 mg of 10% palladium/carbon catalyst are added to a solution of 100 mg (0.26 mmol) of (5R,S)-2-acetoxymethyl-2-penem-3-carboxylic acid p-nitrobenzyl ester in 6 ml of ethyl acetate and the mixture is stirred under hydrogen at normal pressure for 40 minutes. The hydrogenated mixture is filtered off from the catalyst over diatomaceous earth. The aqueous phase is acidified with 10 ml of 5% aqueous citric acid solution and extracted 3 times with 20 ml of methylene chloride each time. The organic phase is dried over sodium sulphate, filtered, concentrated in vacuo and dried under high vacuum. The title compound obtained has the following physico-chemical properties:

TLC: R$_f$=0.16 (toluene/ethyl acetate/acetic acid 60:40:5); UV spectrum (ethanol): $\nu_{max}$=312 and 247 m$\mu$; IR spectrum (KBr): absorption bands at 3.45 b, 5.60, 5.72, 6.00, 6.40, 6.85, 7.25, 7.60, 7.80, 8.20, 8.30, and 9.65$\mu$; NMR spectrum (DMSO d6/100 Mc, in ppm): 2.00, s, 3H; 3.4, dd, J$_A$=16 Hz, J$_B$=2 Hz, 1H; 3.74, dd, J$_A$=16 Hz, J$_C$=4 Hz, 1H; 5.04, d, J=15 Hz, 2H; 5.63, qu, J$_B$=2 Hz, J$_C$=4 Hz, 1H.

EXAMPLE 38

(4R,S)-4-Hexanoylthio-2-oxoazetidine

A solution, prepared in the cold, of 2.64 g (20 mmol) of thiohexanoic acid in 10 ml of 2 N sodium hydroxide solution is added dropwise to an ice-cooled solution of 2.58 g (20 mmol) of (4R,S)-4-acetoxyazetidin-2-one in 10 ml of dioxan, and the mixture is stirred at room temperature for 30 minutes. The reaction mixture is extraced with methylene chloride. The combined organic phases are dried over sodium sulphate and concentrated in vacuo. The residue is chromatographed over silica gel with toluene/ethyl acetate and yields the title compound having the following physico-chemical properties:

TLC: R$_f$=0.43 (toluene/ethyl acetate 1:1); IR spectrum (CH$_2$Cl$_2$): absorption bands at 3.00, 5.65 and 5.85$\mu$.

EXAMPLE 39

2-[(4R,S)-4-Hexanoylthio-2-oxo-1-azetidinyl]-2-hydroxyacetic acid p-nitrobenzyl ester 2.38 g (11.84 mmol) of (4R,S)-4-hexanoylthio-2-oxoazetidine and 6 g of 2-ethoxy-2-hydroxyacetic acid p-nitrobenzyl ester are dissolved at room temperature in a mixture of 120 ml of toluene and 30 ml of dimethylformamide. After adding freshly dried molecular sieves, the mixture is stirred under nitrogen for 15 hours at room temperature and then for 2 hours at 50°. The molecular sieves are filtered off, the filtrate is concentrated in vacuo and the residue is chromatographed over silica gel with toluene/ethyl acetate (9:1 to 4:1). After eluting the unreacted 2-ethoxy-2-hydroxyacetic acid p-nitrobenzyl ester, the crude title compound having the following physico-chemical properties is eluted:

TLC: R$_f$=0.47 (toluene/ethyl acetate 1:1); IR spectrum (CH$_2$Cl$_2$): absorption bands at 2.85, 5.65, 5.75, 5.85, 6.25, 6.58 and 7.45$\mu$.

EXAMPLE 40

2-[(4R,S)-4-Hexanoylthio-2-oxo-1-azetidinyl]-2-triphenylphosphoranylideneacetic acid p-nitrobenzyl ester (a) A solution of 6.70 g of 2-[(4R,S)-4-hexanoylthio-2-oxo-1-azetidinyl]-2-hydroxyacetic acid p-nitrobenzyl ester in 100 ml of dioxan is stirred with 15 g of poly-Hünig base, and a solution of 6 ml of thionyl chloride in 50 ml of dioxan is added dropwise. The reaction mixture is stirred for 5 hours at room temperature, the poly-Hünig base is filtered off and the filtrate is concentrated in vacuo.

(b) The crude 2-[(4R,S)-4-hexanoylthio-2-oxo-1-azetidinyl]-2-chloroacetic acid p-nitrobenzyl ester obtained is dissolved in 150 ml of dioxan, 15 g of poly-Hünig base and 6 g of triphenylphosphine are added, and the mixture is stirred overnight at 50°. The poly-Hünig base is filtered off and the filtrate is concentrated in vacuo. The residue is chromatographed over silica gel with toluene/ethyl acetate (9:1 to 1:1) and yields the title compound having the following physico-chemical properties:

TLC: R$_f$=0.33 (toluene/ethyl acetate 1:1); IR spectrum (CH$_2$Cl$_2$): absorption bands at 5.70, 5.9, 6.15, 6.57, 6.96, 7.45, 9.05 and 9.25$\mu$.

EXAMPLE 41

(5R,S)-2-Pentyl-2-penem-3-carboxylic acid p-nitrobenzyl ester

A catalytic amount of hydroquinone is added to a solution of 4.4 g (6.7 mmol) of 2-[(4R,S)-4-hexanoylthio-2-oxo-1-azetidinyl]-2-triphenylphosphoranylideneacetic acid p-nitrobenzyl ester in 2 liters of dry toluene and the mixture is stirred for 2 days at 90°. The solvent is evaporated off in vacuo and the residue is chromatographed over silica gel with toluene/ethyl acetate (19:1). The title compound having the following physico-chemical properties is obtained:

TLC: R$_f$=0.68 (toluene/ethyl acetate 1:1); UV spectrum (ethanol): $\nu_{max}$=310 nm ($\epsilon$=9759); 270 nm ($\epsilon$=13 593); IR spectrum (CH$_2$Cl$_2$): absorption bands at 5.60, 5.85, 6.35, 6.57, 7.43, 7.65, 8.37 and 9.05$\mu$; NMR spectrum (in CDCl$_3$/100 Mc, in ppm): 8.20, d, J=8 Hz, 2H; 7.60, d, J=8 Hz, 2H; 5.62, qu, J$_{cis}$=4 Hz, J$_{trans}$=2 Hz, 1H; 5.44, d, J=14 Hz, 1H; 5.20, d, J=14 Hz, 1H; 3.80, qu, J=16 Hz, J$_{cis}$=4 Hz, 1H; 3.48, qu, J=16 Hz, J$_{trans}$=2 Hz, 1H; 2.84, m, J=14 Hz, J=7 Hz, 2H; 1.10–1.70, m, 6H; 0.88, t, 3H.

EXAMPLE 42

(5R,S)-2-Pentyl-2-penem-3-carboxylic acid 32 ml of 0.2 M aqueous sodium bicarbonate solution and 1.60 g of 10% palladium/carbon catalyst are added to a solution of 800 mg (2.1 mmol) of (5R,S)-2-pentyl-2-penem-3-carboxylic acid p-nitrobenzyl ester in 48 ml of ethyl acetate and the mixture is stirred at normal pressure for 60 minutes under hydrogen. The hydrogenated mixture is filtered off from the catalyst over diatomaceous earth. The aqueous phase is acidified with 80 ml of 5% aqueous citric acid solution and extracted with methylene chloride. The organic phase is dried over sodium sulphate, filtered, concentrated in vacuo and dried under high vacuum. The title compound obtained is recrystallised from diethyl ether. Melting point: 99°–100°; UV spectrum (ethanol): $\lambda_{max}=307$ mµ ($\epsilon=5321$); 257 mµ ($\epsilon=3712$); IR spectrum ($CH_2Cl_2$): absorption bands at 2.75–4.25 (b); 5.60, 5.97, 6.40, 7.05, 7.70, 8.25, 8.32µ; NMR spectrum ($CDCl_3$/100 Mc, in ppm): 8.20, b, 1H; 5.63, qu, $J_{cis}=4$ Hz, $J_{trans}=2$ Hz, 1H; 3.80, qu, $J_{gem}=16$ Hz, $J_{cis}=4$ Hz, 1H; 3.46, qu, $J_{gem}=16$ Hz, $J_{trans}=2$ Hz, 1H; 283, m,$J_{gem}=14$ Hz, $J_{H,CH_2}=7$ Hz, 2H; 1.10–1.80, m, 6H; 0.89, t, 3H.

EXAMPLE 43

(4R,S)-4-tert.-Butylthioacetylthio-2-oxoazetidine

A solution, prepared in the cold, of 5.74 g (35 mmol) of tert.-butylthiothioacetic acid in 35 ml of 1 N sodium hydroxide solution is added dropwise, while cooling, to a solution of 3.79 g (28.3 mmol) of (4R,S)-4-acetoxyazetidin-2-one in 15 ml of dioxan and the mixture is stirred for two hours at room temperature. The reaction mixture is extracted with methylene chloride. The organic phase is dried over sodium sulphate and concentrated in vacuo. The residue is chromatographed over silica gel with toluene/ethyl acetate (9:1 to 3:1) and yields the title compound with the following physico-chemical properties:

TLC: $R_f=0.39$ (toluene/ethyl acetate 1:1); IR spectrum ($CH_2Cl_2$); absorption bands at 2.97, 3.42, 5.65, 5.87, 8.62 and 10.22µ.

The thiocarboxylic acid used as starting material is obtained as follows:

A mixture of 50 ml of pyridine and 150 ml of dry methylene chloride is saturated with hydrogen sulphide while cooling, and over a period of 30 minutes a solution of 10 g (0.06 mol) of tert.-butylthioacetyl chloride in 50 ml of dry methylene chloride is added dropwise. The reaction mixture is heated to room temperature whilst passing through hydrogen sulphide and is stirred for 2 hours. After acidifying with 2 N sulphuric acid, the organic phase is separated, dried and concentrated in vacuo. The residue is used in the above reaction without further purification.

EXAMPLE 44

2-[(4R,S)-4-tert.-Butylthioacetylthio-2-oxo-1-azetidinyl]-2-hydroxyacetic acid p-nitrobenzyl ester Freshly dried molecular sieves are added to a solution of 4.8 g (20.5 mmol) of (4R,S)-4-tert.-butylthioacetylthio-2-oxoazetidine and 11.6 g of 2-ethoxy-2-hydroxyacetic acid p-nitrobenzyl ester in a mixture of 250 ml of dry toluene and 55 ml of dimethylformamide and the mixture is stirred for 16 hours at room temperature and then for 2 hours at 50°. The molecular sieves are filtered off, the filtrate is concentrated in vacuo and the residue is chromatographed over silica gel with toluene/ethyl acetate (4:1). After eluting the unreacted 2-ethoxy-2-hydroxyacetic acid p-nitrobenzyl ester, the title compound having the following physico-chemical properties is eluted:

TLC: $R_f=0.38$ (toluene/ethyl acetate 1:1); IR-spectrum ($CH_2Cl_2$): absorption bands at 2.85, 5.62, 5.70, 5.95, 6.22, 6.55, 7.42, 8.30, 9.25 and 11.75µ.

EXAMPLE 45

2-[(4R,S)-4-tert.-Butylthioacetylthio-2-oxo-1-azetidinyl]-2-triphenylphosphoranylideneacetic acid p-nitrobenzyl ester (a) A mixture of 9.46 g of 2-[(4R,S)-4-acetylthio-2-oxo-1-azetidinyl]-2-hydroxyacetic acid p-nitrobenzyl ester, contaminated by some 2-ethoxy-2-hydroxyacetic acid p-nitrobenzyl ester, and 1.52 g of poly-Hünig base in 180 ml of dioxan, is stirred for 30 minutes, and a solution of 2.6 ml of thionyl chloride in 50 ml of dioxan is added. The reaction mixture is stirred for 2 hours at room temperature, the poly-Hünig base is filtered off and the filtrate is concentrated in vacuo.

(b) The crude 2-[(4R,S)-4-tert.-butylthioacetylthio-2-oxo-1-azetidinyl]-2-chloroacetic acid p-nitrobenzyl ester so obtained is dissolved in 200 ml of dioxan, 15 g of poly-Hünig base and 6.125 g of triphenylphosphine are added and the mixture is stirred for 16 hours at 50°. The poly-Hünig base is filtered off and the filtrate is concentrated in vacuo. The residue is chromatographed over silica gel with toluene/ethyl acetate (9:1 to 4:1) and yields the title compound having the following physico-chemical properties:

TLC: $R_f=0.27$ (toluene/ethyl acetate 1:1); IR-spectrum ($CH_2Cl_2$): absorption bands at 3.40, 5.65, 5.95, 6.12, 6.55, 7.40, 8.00 and 8.20µ.

EXAMPLE 46

(5R,S)-2-tert.-Butylthiomethyl-2-penem-3-carboxylic acid p-nitrobenzyl ester

A catalytic amount of hydroquinone is added to a solution of 2.57 g (3.75 mmol) of 2-[(4R,S)-4-tert.-butylthio-2-oxo-1-azetidinyl]-2-triphenylphosphoranylideneacetic acid p-nitrobenzyl ester in 800 ml of dry toluene and the mixture is stirred for 17 hours at 90°. The solvent is evaporated off in vacuo and the residue is chromatographed over silica gel with toluene/ethyl acetate (9:1). The title compound is obtained by crystallisation from methylene chloride/petroleum ether and has the following physico-chemical properties:

Melting point 150°–152°; TLC: $R_f=0.59$ (toluene/ethyl acetate 1:1); UV spectrum (ethanol): $\lambda_{max}=323$ nm ($\epsilon=8084$); 263 nm ($\epsilon=13313$); IR spectrum ($CH_2Cl_2$): absorption bands at 3.37, 5.60, 5.85, 6.58, 7.45, 7.65, 8.45 and 8.85µ; NMR spectrum (in $CDCl_3$/100 Mc, in ppm): 8.20, d, J=8 Hz, 2H; 7.60, d, J=8 Hz, 2H; 5.61, qu, $J_{cis}=4$ Hz, $J_{trans}=2$ Hz, 1H; 5.46, d, $J_{gem}=14$ Hz, 1H; 5.24, d, $J_{gem}=14$ Hz, 1H; 4.08, d, $J_{gem}=14$ Hz, 1H; 3.86, d, $J_{gem}=14$ Hz, 1H; 3.80, m, $J_{gem}=16$ Hz, $J_{cis}=4$ Hz, 1H; 3.52, m, $J_{gem}=16$ Hz, $J_{trans}=2$ Hz, 1H; 1.32, s, 9H.

EXAMPLE 47

(5R,S)-2-tert.-Butylthiomethyl-2-penem-3-carboxylic acid 3.6 ml of 0.2 M aqueous sodium bicarbonate solution and 183 mg of 10% palladium/carbon catalyst are added to a solution of 116 mg (0.28 mmol) of (5R,S)-2-tert.-butylthiomethyl-2-penem-3-carboxylic acid p-nitrobenzyl ester in 10 ml of ethyl acetate and the mixture is stirred at normal pressure for 60 minutes under hydrogen. The hydrogenated mixture is filtered off from the catalyst over diatomaceous earth. The aqueous phase is washed with diethyl ether, acidified with 5% aqueous citric acid solution and extracted with methylene chloride. The organic phase is dried over sodium sulphate, filtered, concentrated in vacuo and dried under high vacuum. The title compound obtained has the following physico-chemical properties: melting point 132°–133° (from acetone/diethyl ether); UV spectrum (ethanol): $\lambda_{max}=314$ mμ ($\epsilon=3918$); 259 mμ (3667); IR spectrum (KBr): absorption bands at 2.95, 3.40, 3.95, 5.60, 6.02, 6.47, 6.95, 7.52, 7.87, 8.20 and 14.05μ; NMR spectrum (DMSO d6/100 Mc, in ppm): 5.62, qu, $J_{cis}=4$ Hz, $J_{trans}=\sim 2$ Hz, 1H; 4.20, d, $J_{gem}=14$ Hz, 1H; 3.83, d, $J_{gem}=14$ Hz, 1H; 3.80, $J_{gem}=16$ Hz, $J_{cis}=4$ Hz, 1H; 3.44, qu, $J_{gem}=16$ Hz, $J_{trans}=\sim 2$ Hz, 1H; 1.30, s, 9H.

EXAMPLE 48

(4R,S)-4-(4-p-Nitrobenzyloxycarbonylaminobutyrylthio)-2-oxoazetidine

A solution, prepared in the cold, of 2.98 g (10 mmol) of 4-p-nitrobenzyloxycarbonylaminothiobutyric acid in 10 ml of 1 N sodium hydroxide solution is added dropwise to a precooled solution of 1.1 g (8.52 mmol) of (4R,S)-4-acetoxyazetidin-2-one in 10 ml of dioxan and the mixture is stirred at room temperature for 1½ hours. The reaction mixture is exhaustively extracted with methylene chloride. The combined organic phases are dried over sodium sulphate and concentrated in vacuo. The residue is chromatographed over silica gel with toluene/ethyl acetate (9:1, 7:2 and 1:1) and yields the title compound with the following physico-chemical properties:

TLC: $R_f=0.33$ (toluene/ethyl acetate 1:2); IR spectrum ($CH_2Cl_2$): absorption bands at 2.95, 5.65, 5.80, 5.92, 6.25, 6.60, 7.45 and 8.15μ.

The thiocarboxylic acid used as starting material is obtained as follows:

(a) A solution of 25.87 g (0.12 mmol) of p-nitrobenzyl chloroformate in 100 ml of dry dioxan is added dropwise in a period of 20 minutes to a solution of 10.30 g (0.1 mmol) of 4-aminobutyric acid in 300 ml of 1 N sodium hydroxide solution in an ice bath. The reaction mixture is stirred for 3 hours at room temperature, washed with ethyl acetate and acidified with 2 N hydrochloric acid. The precipitated 4-p-nitrobenzyloxycarbonylaminobutyric acid is filtered off and recrystallised from ethyl acetate; melting point: 145°–146°.

(b) 2.2 g (20 mmol) of triethylamine and a solution of 1.4 ml (10 mmol) of isobutyl chloroformate in 20 ml of dry methylene chloride are added dropwise in succession to a solution, cooled to −10°, of 2.82 g (10 mmol) of 4-p-nitrobenzyloxycarbonylaminobutyric acid in 50 ml of dry methylene chloride. The reaction mixture is stirred for one hour and subsequently a strong current of hydrogen sulphide is passed through for a period of 2 hours. After acidifying with 2 N sulphuric acid, the organic phase is separated, dried and concentrated in vacuo. The 4-p-nitrobenzyloxycarbonylaminothiobutyric acid obtained can be used without further purification.

EXAMPLE 49

2-[(4R,S)-4-(4-p-Nitrobenzyloxycarbonylaminobutyrylthio)-2-oxo-1-azetidinyl]-2-hydroxyacetic acid p-nitrobenzyl ester 2.724 g (7.42 mmol) of (4R,S)-4-p-nitrobenzyloxycarbonylaminobutyrylthio)-2-oxoazetidine and 4.35 g of 2-ethoxy-2-hydroxyacetic acid p-nitrobenzyl ester are dissolved at room temperature in 120 ml of toluene and 30 ml of dimethylformamide. After adding freshly dried molecular sieves the mixture is stirred under nitrogen overnight at room temperature and then for 2 hours at 50°. The molecular sieves, are filtered off, the filtrate is concentrated in vacuo and the residue is chromatographed over silica gel with toluene/ethyl acetate (9:1, 8:1 and 1:1). After eluting the unreacted 2-ethoxy-2-hydroxyacetic acid p-nitrobenzyl ester, the title compound with the following physico-chemical properties is eluted:

TLC: $R_f=0.23$ (toluene/ethyl acetate 1:2); IR spectrum ($CH_2Cl_2$): absorption bands at 2.95, 5.65, 5.75, 5.82, 6.25, 6.60, 7.45, 8.25, 9.05, 9.80 and 11.75μ.

EXAMPLE 50

2-[(4R,S)-4-(4-p-Nitrobenzyloxycarbonylaminobutyrylthio)-2-oxo-1-azetidinyl]-2-triphenylphosphoranylideneacetic acid p-nitrobenzyl ester (a) A solution of 4 ml of thionyl chloride in 25 ml of absolute dioxane is added dropwise at room temperature to a mixture of 3.676 (6.38 mmol) of 2-[(4R,S)-4-(4-p-nitrobenzyloxycarbonylaminobutyrylthio)-2-oxo-1-azetidinyl]-2-hydroxyacetic acid p-nitrobenzyl ester and 8 g of poly-Hünig base in 50 ml of absolute dioxan. The reaction mixture is stirred for 3 hours at room temperature under nitrogen, the poly-Hünig base is filtered off and the filtrate is concentrated in vacuo.

(b) The crude 2-[(4R,S)-4-(4-p-nitrobenzyloxycarbonylaminobutyrylthio)-2-oxo-1-azetidinyl]-2-chloroacetic acid p-nitrobenzyl ester so obtained is dissolved in 100 ml of absolute dioxan, 9 g of poly-Hünig base and 3 g of triphenylphosphine are added and the mixture is stirred overnight at 50° under nitrogen. The poly-Hünig base is filtered off and the filtrate is concentrated in vacuo. The residue is chromatographed over silica gel with toluene/ethyl acetate (9:1, 8:2 and 1:1) and yields the title compound with the following physico-chemical properties:

IR spectrum ($CH_2Cl_2$): absorption bands at 5.70, 5.80, 5.95, 6.25, 6.60, 7.00, 7.45, 8.15, 8.95, 9.05 and 9.25μ.

EXAMPLE 51

(5R,S)-2-(3-p-Nitrobenzyloxycarbonylaminopropyl)-2-penem-3-carboxylic acid-p-nitrobenzyl ester A catalytic amount of hydroquinone is added to a solution of 1.50 g (1.83 mmol) of 2-[(4R,S)-4-(4-p-nitrobenzyloxycarbonylaminobutyrylthio)-2-oxo-1-azetidinyl]-2-triphenylphosphoranylideneacetic acid p-nitrobenzyl ester in 500 ml of dry toluene and the mixture is stirred under nitrogen for 24 hours at 90°. The solvent is evaporated in vacuo and the residue is chromatographed over silica gel with toluene/ethyl acetate (4:1). The title compound with the following physico-chemical properties is obtained:

TLC: $R_f=0.43$ (toluene/ethyl acetate 1:2); UV spectrum (ethanol): $\lambda_{max}=300$ nm; 264 nm; IR spectrum ($CH_2Cl_2$): absorption bands at 2.80, 5.55, 5.80, 6.20, 6.37, 6.55, 7.40, 7.60 and 8.35μ; NMR spectrum (in $CDCl_3$/100 Mc, in ppm): 1.80, quintet, J=7 Hz, 2H; 2.80, m, 2H; 3.24, qu, J=7 Hz, 2H; 3.47, dd, $J_1=16$ Hz, $J_2=2$ Hz; 3.82, dd, $J_1=16$ Hz, $J_2=4$ Hz; ;b 5.17, s, 2H; 5.18, d, J=14 Hz, 1H; 5.43, d, J=14 Hz, 1H; 5.64, qu, $J_1=2$ Hz, $J_2=4$ Hz, 1H; 5.10–5.70, b, 1H; 7.40–8.20, m, 8H.

EXAMPLE 52

(5R,S)-2-(3-Aminopropyl)-2-penem-3-carboxylic acid 80 mg of 10% palladium/carbon catalyst are added to a solution of 30 mg (0.055 mmol) of (5R,S)-2-(3-p-nitrobenzyloxycarbonylaminopropyl)-2-penem-3-carboxylic acid p-nitrobenzyl ester in 3 ml of methanol and the mixture is stirred at normal pressure for 1½ hours under hydrogen. The hydrogenated mixture is filtered off from the catalyst over diatomaceous earth and the filtrate is concentrated in vacuo. The title compound obtained has the following physico-chemical properties: IR spectrum (KBr): absorption bands at 2.95, 3.45, 5.65, 5.85 (sh), 6.35 and 7.30μ; UV spectrum (ethanol): $\lambda_{max}=299$ nm.

EXAMPLE 53

(4R,S)-3-(4-p-Nitrobenzyloxycarbonylaminopropionyl-thio)-2-oxoazetidine

A solution, prepared in the cold, of 5.60 g (~20 mmol) of 3-p-nitrobenzyloxycarbonylaminothiopropionic acid in 20 ml of 1 N sodium hydroxide solution is added dropwise to a precooled solution of 2.2 g (17 mmol) of (4R,S)-4-acetoxyazetidin-2-one in 10 ml of dioxan and the mixture is stirred at room temperature for 3 hours. The reaction mixture is exhaustively extracted with methylene chloride. The combined organic phases are dried over sodium sulphate and concentrated in vacuo. The residue is chromatographed over silica gel with toluene/ethyl acetate (9:1 to 1:1) and yields the title compound with the following physico-chemical properties:

TLC: $R_f=0.22$ (toluene/ethyl acetate 1:1); IR spectrum (CH$_2$Cl$_2$): absorption bands at 2.95, 5.65, 5.80, 5.95, 6.60, 7.45 and 8.17μ.

The thiocarboxylic acid used as starting material is obtained as follows:

(a) A solution of 21.56 g (0.1 mmol) of p-nitrobenzyl chloroformate in 30 ml of dry dioxan is added dropwise over a period of 20 minutes to a solution of 8.90 g (0.1 mmol) of 3-aminopropionic acid in 100 ml of 2 N sodium hydroxide solution in an ice bath. The reaction mixture is stirred for 2 hours at room temperature and acidified with 2 N hydrochloric acid. The precipitated 3-p-nitrobenzyloxycarbonylaminopropionic acid is filtered off and dried. Melting point: 97°-98° (from ethyl acetate/diethyl ether).

(b) 4.4 g (40 mmol) of triethylamine and a solution of 2.8 ml (2 mmol) of isobutyl chloroformate in 20 ml of dry methylene chloride are added dropwise, in succession, to a solution, cooled to −10°, of 5.36 g (20 mmol) of 3-p-nitrobenzyloxycarbonylaminopropionic acid in 100 l of dry methylene chloride. The reaction mixture is stirred for one hour at −18°, then for 1½ hours a strong current of hydrogen sulphide is passed through and the mixture allowed to heat up to room temperature. After acidifying with 2 N sulphuric acid, again in the cold, the organic phase is separated, dried and concentrated in vacuo. The 3-p-nitrobenzyloxycarbonylaminothiopropionic acid obtained can be used without further purification.

EXAMPLE 54

2-[(4R,S)-4-(3-p-Nitrobenzyloxycarbonylaminopropionylthio)-2-oxo-1-azetidinyl]-2-hydroxyacetic acid p-nitrobenzyl ester 4.10 g (11.6 mmol) of (4R,S)-4-(3-p-nitrobenzyloxycarbonylaminopropionylthio)-2-oxoazetidine and 6.5 g of 2-ethoxy-2-hydroxyacetic acid p-nitrobenzyl ester are dissolved at room temperature in 120 ml of dry toluene and 50 ml of dry dimethylformamide. After adding freshly dried molecular sieves, the mixture is stirred under nitrogen overnight at room temperature and then for 2 hours at 50°. The molecular sieves are filtered off, the filtrate is concentrated in vacuo and the residue is chromatographed over silica gel with toluene/ethyl acetate (9:1 to 1:1). After eluting unreacted 2-ethoxy-2-hydroxyacetic acid p-nitrobenzyl ester, the title compound with the following physico-chemical properties is eluted:

TLC: $R_f=0.23$ (toluene/ethyl acetate 1:1); IR spectrum (CH$_2$Cl$_2$): absorption bands at 2.95, 5.65, 5.75, 5.80, 6.25, 6.55, 7.45, 8.20 and 9.20μ.

EXAMPLE 55

2-[(4R,S)-4-(3-p-Nitrobenzyloxycarbonylaminopropionylthio)-2-oxo-1-azetidinyl]-2-triphenylphosphoranylideneacetic acid p-nitrobenzyl ester (a) A solution of 6 ml of thionyl chloride in 50 ml of dry dioxan is added dropwise at room temperature to a stirred mixture of 6.33 g (11.2 mmol) of 2-[(4R,S)-4-(3-p-nitrobenzyloxycarbonylaminopropionylthio)-2-oxo-1-azetidinyl]-2-hydroxyacetic acid p-nitrobenzyl ester and 12 g of poly-Hünig base in 50 ml of dry dioxan. The reaction mixture is stirred for 1 hour at room temperature under nitrogen, the poly-Hünig base is filtered off and the filtrate is concentrated in vacuo.

(b) The crude 2-[(4R,S)-4-(3-p-nitrobenzyloxycarbonylaminopropionylthio)-2-oxo-1-azetidinyl]-2-chloroacetic acid p-nitrobenzyl ester obtained is dissolved in 50 ml of dry dioxan, 12 g of poly-Hünig base and 4 g of triphenylphosphine are added and the mixture is stirred overnight at 50° under nitrogen. The poly-Hünig base is filtered off and the filtrate is concentrated in vacuo. The residue is chromatographed over silica gel with toluene/ethyl acetate (9:1, 8:2 and 1:1) and yields the title compound with the following physico-chemical properties:

IR spectrum (CH$_2$Cl$_2$): absorption bands at 2.90, 4.67, 5.77, 5.90, 6.12, 6.55, 6.95, 7.40, 9.00 and 9.25μ.

EXAMPLE 56

(5R,S)-2-(2-p-Nitrobenzyloxycarbonylaminoethyl)-2-penem-3-carboxylic acid p-nitrobenzyl ester A catalytic amount of hydroquinone is added to a solution of 3 g (3.7 mmol) of 2-[(4R,S)-4-(3-p-nitrobenzyloxycarbonylaminopropionylthio)-2-oxo-1-azetidinyl]-2-triphenylphosphoranylideneacetic acid p-nitrobenzyl ester in 250 ml of dry toluene and the mixture is stirred under nitrogen for 24 hours at 90°. The solvent is evaporated off in vacuo and the residue is chromatographed over silica gel with toluene/ethyl acetate (9:1 to 4:1). The title compound with the following physico-chemical properties is obtained: TLC: $R_f=0.44$ (toluene/ethyl acetate 1:1); UV spectrum (dioxan): $\lambda_{max}=315$ nm ($\epsilon=8536$); 264 nm ($\epsilon=22114$); IR spectrum (CH$_2$Cl$_2$): absorption bands at 2.95, 5.58, 5.80, 6.22, 6.32, 6.57, 7.42, 7.62 and 8.35μ; NMR spectrum (in CDCl$_3$/100 Mc, in ppm): 2.80–3.60, m, 5H; 3.84, dd, J$_1$=16 Hz, J$_2$=4 Hz, 1H; 5.18, s, 2H; 5.22, d, J$_1$=14 Hz, 1H; 5.44, d, J=14 Hz, 1H; 5.65, qu, J$_2$=4 Hz, J$_3$=2 Hz, 1H; 7.40–8.30, m, 8H.

EXAMPLE 57

(5R,S)-2-(2-Aminoethyl)-2-penem-3-carboxylic acid 200 mg of 10% palladium/carbon catalyst are added to a solution of 90 mg (0.19 mmol) of (5R,S)-2-(2-p-nitrobenzyloxycarbonylaminoethyl)-2-penem-3-carboxylic acid p-nitrobenzyl ester in 3 ml of methanol and the mixture is stirred at normal pressure for one hour under hydrogen. The hydrogenated mixture is filtered off from the catalyst over diatomaceous earth, the filtrate is concentrated in vacuo and the residue is washed once with diethyl ether. The title compound obtained has the following physico-chemical properties:

IR spectrum (KBr): absorption bands at 3.00, 5.67, 5.90, 6.25, 6.30 and 7.30μ.

EXAMPLE 58

(4R,S)-4-(4-Benzyloxycarbonylaminobutyrylthio)-2-oxoazetidine

A solution, prepared in the cold, of 2.53 g (10 mmol) of 4-benzyloxycarbonylaminothiobutyric acid in 10 ml of 1 N sodium hydroxide solution is added dropwise to a solution of 1.29 g (10 mmol) of (4R,S)-4-acetoxyazetidin-2-one in 10 ml of dioxan, and the mixture is stirred at room temperature for 20 minutes. The reaction mixture is exhaustively extracted with methylene chloride. The combined organic phases are dried over sodium sulphate and concentrated in vacuo. The residue is chromatographed over silica gel with toluene/ethyl acetate (1:1) and yields the title compound with the following physico-chemical properties:

TLC: R$_f$=0.38 (toluene/ethyl acetate 1:2); IR spectrum (CH$_2$Cl$_2$): absorption bands at 2.95, 5.60, 5.80, 5.90, 6.60 and 8.10μ.

The thiocarboxylic acid used as starting material is obtained as follows:

(a) A solution of 5.16 g (0.103 mmol) of benzyl chloroformate in 100 ml of dry dioxan is added dropwise over a period of 30 minutes to a solution of 10.60 g (0.1 mmol) of 4-aminobutyric acid in 300 ml of 1 N sodium hydroxide solution in an ice bath. The reaction mixture is stirred for 30 minutes at room temperature, acidified with 2 N hydrochloric acid and extracted with methylene chloride. The organic phase is dried with sodium sulphate and concentrated in vacuo. The 4-benzyloxycarbonylaminobutyric acid obtained is recrystallised from ethyl acetate, methylene chloride and hexane; melting point 61°–62°.

(b) 2.2 g (20 mmol) of triethylamine and a solution of 1.4 ml (10 mmol) of isobutyl chloroformate in 20 ml of dry methylene chloride are added dropwise, in succession, to a solution, cooled to −10°, of 2.37 g (10 mmol) of 4-benzyloxycarbonylaminobutyric acid in 50 ml of dry methylene chloride. The reaction mixture is stirred for one hour at −10° and then a strong current of hydrogen sulphide is passed through for 1½ hours. After warming to room temperature, the mixture is cooled again and acidified with 2 N sulphuric acid. The organic phase is separated, dried and concentrated in vacuo. The 4-benzyloxycarbonylaminothiobutyric acid obtained can be used without further purification.

EXAMPLE 59

2-[(4R,S)-4-(4-Benzyloxycarbonylaminobutyrylthio)-2-oxo-1-azetidinyl]-2-hydroxyacetic acid p-nitrobenzyl ester 2.60 g (8 mmol) of (4R,S)-4-(4-benzyloxycarbonylaminobutyrylthio)-2-oxoazetidine and 4.84 g of 2-ethoxy-2-hydroxyacetic acid p-nitrobenzyl ester are dissolved at room temperature in a mixture of 100 ml of dry toluene and 35 ml of dry dimethylformamide. After adding freshly dried molecular sieves, the mixture is stirred under nitrogen overnight at room temperature and then for 2 hours at 50°. The molecular sieves are filtered off, the filtrate is concentrated in vacuo and the residue is chromatographed over silica gel with toluene/ethyl acetate (4:1). After eluting the unreacted 2-ethoxy-2-hydroxyacetic acid p-nitrobenzyl ester, the title compound with the following physico-chemical properties is eluted:

TLC: R$_f$=0.38 (toluene/ethyl acetate 1:2); IR spectrum (CH$_2$Cl$_2$): absorption bands at 2.85, 2.95, 5.60, 5.70, 5.82, 5.97, 6.22, 6.55, 7.42, 8.25 and 9.15μ.

EXAMPLE 60

2-[(4R,S)-4-(4-Benzyloxycarbonylaminobutyrylthio)-2-oxo-1-azetidinyl]-2-triphenylphosphoranylideneacetic acid p-nitrobenzyl ester (a) A solution of 6 ml of thionyl chloride in 50 ml of dioxan is added dropwise at room temperature to a mixture of 7 g of 2-[(4R,S)-4-(4-benzyloxycarbonylaminobutyrylthio)-2-oxo-1-azetidinyl]-2-hydroxyacetic acid p-nitrobenzyl ester and 15 g of poly-Hünig base in 200 ml of dioxan. The reaction mixture is stirred for 2 hours at room temperature, the poly-Hünig base is filtered off and the filtrate is concentrated in vacuo.

(b) The crude 2-[(4R,S)-4-(4-benzyloxycarbonylaminobutyrylthio)-2-oxo-1-azetidinyl]-2-chloroacetic acid p-nitrobenzyl ester obtained is dissolved in 150 ml of dry dioxan, 15 g of poly-Hünig base and 6 g of triphenylphosphine are added and the mixture is stirred overnight at 50°. The poly-Hünig base is filtered off and the filtrate is concentrated in vacuo. The residue is chromatographed over silica gel with toluene/ethyl acetate (9:1 to 1:1), and yields the title compound with the following physico-chemical properties:

TLC: R$_f$=0.37 (toluene/ethyl acetate 1:2); IR spectrum (CH$_2$Cl$_2$): absorption bands at 2.92, 5.70, 5.78, 5.92, 6.15, 6.60, 6.97, 7.45, 8.40, 8.95, 9.05 and 9.25μ.

EXAMPLE 61

(5R,S)-2-(3-Benzyloxycarbonylaminopropyl)-2-penem-3-carboxylic acid p-nitrobenzyl ester A catalytic amount of hydroquinone is added to a solution of 1 g (1.29 mmol) of 1-[(4R,S)-4-(4-benzyloxycarbonylaminobutyrylthio)-2-oxo-1-azetidinyl]-2-triphenylphosphoranylideneacetic acid p-nitrobenzyl ester in 500 ml of dry toluene and the mixture is stirred under nitrogen for 36 hours at 90°. The solvent is evaporated off in vacuo and the residue is chromatographed over silica gel with toluene/ethyl acetate (4:1). The title compound with the following physico-chemical properties is obtained:

TLC: R$_f$=0.42 (toluene/ethyl acetate 1:1) UV spectrum (ethanol): λ$_{max}$=311 nm; 260 nm; IR spectrum (CH$_2$Cl$_2$): absorption bands at 2.95, 5.60, 5.85, 6.20, 7.45, 7.65, 8.10 and 8.38μ; NMR spectrum (in CDCl$_3$/100 Mc, in ppm): 1.75, quintet, 2H; 2.85 m, 2H; 3.19, qu, J=7 Hz, 2H; 3.40, dd, J$_1$=16 Hz, J$_2$=2 Hz, 1H; 3.74, dd, J$_1$=16 Hz, J$_2$=4 Hz, 1H; 5.06, s, 2H; 5.14, d, J=14 Hz and 5.38, d, J=14 Hz, 2H; 5.60, qu, J$_1$=2 Hz, J$_2$=4 Hz, 1H; 7.28, s, 5H; 7.54, d, J=9 Hz, 2H; 8.12, d, J=9 Hz, 2H.

EXAMPLE 62

(5R,S)-2-(3-Benzyloxycarbonylaminopropyl)-2-penem-3-carboxylic acid 200 mg of 10% palladium/carbon catalyst is added to a solution of 105 mg (0.21 mmol) of (5R,S)-2-(3-benzyloxycarbonylaminopropyl)-2-penem-3-carboxylic acid p-nitrobenzyl ester in 6 ml of ethyl acetate and 4 ml of 0.2 M sodium bicarbonate solution, and the mixture is stirred at normal pressure for one hour under hydrogen. The hydrogenated mixture is filtered off from the catalyst over diatomaceous earth, the aqueous phase is separated, acidified with 5% aqueous citric acid solution and extracted with methylene chloride. The organic phase is dried over sodium sulphate and concentrated in vacuo. The title compound obtained has the following physico-chemical properties:

TLC: R$_f$=0.41 (toluene/ethyl acetate/acetic acid 60:40:5); IR spectrum (CH$_2$Cl$_2$): absorption bands at 2.95, 5.60, 5.85, 6.40, 6.65 and 8.10$\mu$; UV spectrum (ethanol): $\lambda_{max}$=307 and 255 nm.

EXAMPLE 63

(4R,S)-4-[2-(2-Phenoxyacetylamino)-acetylthio]-2-oxoazetidine

A solution, prepared in the cold, of 6 g (26.6 mmol) of 2-(2-phenoxyacetylamino)-thioacetic acid in 26 ml of 1 N sodium hydroxide solution is added dropwise to a precooled solution of 3.43 g (26.5 mmol) of (4R,S)-4-acetoxyazetidin-2-one in 20 ml of dioxan and the mixture is stirred at room temperature for 30 minutes. The reaction mixture is exhaustively extracted with methylene chloride. The combined organic phases are dried over sodium sulphate and concentrated in vacuo. The residue is chromatographed over silica gel with toluene/ethyl acetate (1:1) and yields the title compound with the following physico-chemical properties:

Melting point: 114°–115° (from methylene chloride/petroleum ether);

TLC: R$_f$=0.41 (ethyl acetate); IR-spectrum (CH$_2$Cl$_2$): absorption bands at 2.95, 5.60, 5.90, 6.25, 6.60, 6.70, 8.10, 9.25, 9.42 and 10.20$\mu$.

The thiocarboxylic acid used as starting material is obtained as follows:

7.4 ml (53.8 mmol) of triethylamine and a solution of 3.7 ml (26.9 mmol) of isobutyl chloroformate in 60 ml of methylene chloride are added dropwise, in succession, to a solution, cooled to −10°, of 5.63 g (26.9 mmol) of 2-(2-phenoxyacetylamino)-acetic acid in 50 ml of dry methylene chloride. The reaction mixture is stirred for 1½ hours at −10° and at the same temperature a current of hydrogen sulphide is passed through for a period of 2 hours. After warming to room temperature, the mixture is acidified with 2 N sulphuric acid, the organic phase is separated, dried and concentrated in vacuo. The 2-(2-phenoxyacetylamino)-acetic acid obtained can be used without further purification.

EXAMPLE 64

2-{(4R,S)-4-[2-(2-Phenoxyacetylamino)-acetylthio]-2-oxo-1-azetidinyl}-2-hydroxyacetic acid p-nitrobenzyl ester.

1.40 g (4.76 mmol) of (4R,S)-4-[2-(2-phenoxyacetylamino)acetylthio]-2-oxoazetidine and 3.2 g of 2-ethoxy-2-hydroxyacetic acid p-nitrobenzyl ester are dissolved at room temperature in a mixture of 60 ml of toluene and 15 ml of dimethylformamide. After adding freshly dried molecular sieves, the mixture is stirred under nitrogen overnight at room temperature and then for two hours at 50°. The molecular sieves are filtered off, the filtrate is concentrated in vacuo and the residue is chromatographed over silica gel with toluene/ethyl acetate (1:2). After eluting the unreacted 2-ethoxy-2-hydroxyacetic acid p-nitrobenzyl ester, the title compound with the following physico-chemical properties is eluted:

TLC: R$_f$=0.43 (ethyl acetate); IR spectrum (CH$_2$Cl$_2$): absorption bands at 2.95, 5.60, 5.70, 5.90, 6.25, 6.55, 7.42 and 8.20$\mu$.

EXAMPLE 65

2-{(4R,S)-4-[2-(2-Phenoxyacetylamino)-acetylthio]-2-oxo-1-azetidinyl}-2-triphenylphosphoranylideneacetic acid p-nitrobenzyl ester (a) A solution of 0.76 ml of thionyl chloride in 25 ml of dioxan is added dropwise at room temperature to a mixture of 3.01 g (5.88 mmol) of 2-{(4R,S)-4-[2-(2-phenoxyacetylamino)-acetylthio]-2-oxo-1-azetidinyl}-2-hydroxyacetic acid p-nitrobenzyl ester and 4.45 g of poly-Eünig base in 65 ml of dry dioxan. The reaction mixture is stirred for 2 hours at room temperature under nitrogen, the poly-Hünig base is filtered off and the filtrate is concentrated in vacuo.

(b) The crude 2-{(4R,S)-4-[2-(2-phenoxyacetylamino)acetylthio]-2-oxo-1-azetidinyl}-2-chloroacetic acid p-nitrobenzyl ester obtained is dissolved in 100 ml of dioxan, 5.62 g of poly-Hünig base and 2.30 g of triphenylphosphine are added and the mixture is stirred for 17 hours at 50° under nitrogen. The poly-Hünig base is filtered off and the filtrate is concentrated in vacuo. The residue is chromatographed over silica gel with toluene/ethyl acetate (3:2) and yields the title compound with the following physico-chemical properties:

TLC: R$_f$=0.09 (toluene/ethyl acetate 1:1); IR spectrum (CH$_2$Cl$_2$): absorption bands at 2.95, 5.70, 5.80, 6.20, 6.70, 6.98, 7.45, 8.40 and 8.95$\mu$.

EXAMPLE 66

(5R,S)-2-(2-Phenoxyacetylaminomethyl)-2-penem-3-carboxylic acid p-nitrobenzyl ester A catalytic amount of hydroquinone is added to a solution of 600 mg (0.8 mmol) of 2-{(4R,S)-4-[2-(2-phenoxyacetylamino)-acetylthio]-2-oxo-1-azetidinyl}-2-triphenylphosphoranylideneacetic acid p-nitrobenzyl ester in 300 ml of dry toluene and the mixture is stirred under nitrogen for 17 hours at 90°. The solvent is evaporated off in vacuo, the residue is dissolved in methylene chloride and washed with cold 1 N sodium hydroxide solution. The organic phase is dried over sodium sulphate and concentrated in vacuo. The residue is chromatographed over silica gel with toluene/ethyl acetate (4:1). The title compound with the following physicochemical properties is obtained: melting point: 163°–165° (methylene chloride/petroleum ether);

TLC: $R_f=0.35$ (toluene/ethyl acetate 1:1); UV spectrum (dioxan): $\lambda_{max}=318$ nm ($\epsilon=10019$); 272 nm (sh) ($\epsilon=12684$), 266 nm ($\epsilon=14869$); 261 nm ($\epsilon=14869$); IR spectrum ($CH_2Cl_2$): absorption bands at 2.95, 5.55, 5.85, 5.90, 6.30, 6.55, 6.70, 7.40, 7.60, 8.10, 8.25, 8.65 and 9.40µ; NMR spectrum (in $CDCl_3$/100 Mc, in ppm): 3.44, dd, $J_1=16$ Hz, $J_2=2$ Hz, 1H; 3.84, dd, $J_1=16$ Hz, $J_3=4$ Hz, 1H; 4.52, s, 2H; 4.34–4.80, m, 2H; 5.22, d, $J=14$ Hz, 1H; 5.44, d, $J=14$ Hz, 1H; 4.66, qu, $J_2=2$ Hz, $J_3=4$ Hz, 1H; 6.80–8.30, m, 10H.

EXAMPLE 67

(5R,S)-2-(2-Phenoxyacetylaminomethyl)-2-penem-3-carboxylic acid 135 mg of 10% palladium/carbon catalyst is added to a solution of 100 mg (0.21 mmol) of (5R,S)-2-(2-phenoxyacetylaminomethyl)-2-penem-3-carboxylic acid p-nitrobenzyl ester in 10 ml of ethyl acetate and 2.7 ml of 0.2 N sodium bicarbonate solution and the mixture is stirred at normal pressure for 45 minutes under hydrogen. The hydrogenated mixture is filtered off from the catalyst over diatomaceous earth. The aqueous phase is separated, acidified with 5% citric acid solution and extracted with methylene chloride. The combined methylene chloride phases are dried over sodium sulphate and concentrated in vacuo. The title compound obtained has the following physico-chemical properties:

TLC: $R_f=0.08$ (toluene/ethyl acetate/acetic acid 60:40:5); IR spectrum (methylene chloride): absorption bands at 2.8–3.60 (b), 5.55, 5.75, 5.85, 6.25, 6.55, 6.70 and 8.10µ.

EXAMPLE 68

(4R,S)-4-Ethylthiothiocarbonylthio-2-oxoazetidine

A solution of 2.25 g of potassium ethyltrithiocarbonate in 12 ml of water is added dropwise at room temperature, under a nitrogen atmosphere, to a solution of 1.32 g of (4R,S)-4-acetoxyazetidin-2-one in 3.5 ml of water and 1 ml of acetone and the mixture is stirred at the same temperature for 30 minutes. The reaction mixture is exhaustively extracted with methylene chloride, the combined organic phases are washed with saturated, aqueous sodium chloride solution, dried over sodium sulphate and concentrated in vacuo. The residue is recrystallised from diethyl ether and yields the title compound in the form of yellow needles.

Melting point: 99.5°–101.5°; TLC: $R_f=0.315$ (toluene/ethyl acetate 2:3); IR spectrum ($CH_2Cl_2$): absorption bands at 2.95, 5.6, 8.12, 9.15 and 9.3µ; NMR spectrum (in $CDCl_3$/100 Mc, in ppm): 6.85, 1H, m (exchange with $D_2O$); 5.55, 1H, m; 3.35, 2H, q; 3.6–2.9, 2H, m; 1.35, 3H, t.

EXAMPLE 69

2-[(4R,S)-4-Ethylthiothiocarbonylthio-2-oxo-1-azetidinyl]-2-hydroxy acetic acid p-nitrobenzyl ester 1.7 g of 2-ethoxy-2-hydroxyacetic acid p-nitrobenzyl ester is added at room temperature to a solution of 621 mg (3 mmol) of (4R,S)-4-ethylthiothiocarbonylthio-3-oxoazetidine in 35 ml of toluene and 9 ml of dimethylformamide. After adding freshly dried molecular sieves, the mixture is stirred under nitrogen for 15 hours at room temperature and then for 2 hours at 50°. The molecular sieves are filtered off, washed with toluene and the filtrate and washing liquid are evaporated together in vacuo. The residue is dried under high vacuum and chromatographed over 80 g of silica gel with toluene/ethyl acetate (9:1). The title compound with the following physico-chemical properties is obtained:

TLC: $R_f=0.26$ (toluene/ethyl acetate 2:3); IR spectrum ($CH_2Cl_2$): absorption bands at 5.62, 5.7, 6.55 and 7.45µ; NMR spectrum (in $CDCl_3$/100 Mc, in ppm): 8.3–8.15, 2H, m; 7.6–7.45, 2H, m; 6.1–5.9, 1H, m; 5.55, 1H, d; 5.4–5.3, 2H, m; 4.2–4, 1H, m (exchange with $D_2O$); 3.8–3, 4H, m; 1.35, 3H, t.

EXAMPLE 70

2-[(4R,S)-4-Ethylthiothiocarbonylthio-2-oxo-1-azetidinyl]-2-triphenylphosphoranylideneacetic acid p-nitrobenzyl ester (a) A solution of 1.1 g of 2-[(4R,S)-ethylthiothiocarbonylthio-2-oxo-1-azetidinyl]-2-hydroxyacetic acid p-nitrobenzyl ester in 23 ml of absolute dioxan is added to a solution of 4.55 g of poly-Hünig base in 11 ml of absolute dioxan that has already been stirred for 30 minutes. After adding dropwise a solution of 0.8 ml of thionyl chloride, the reaction mixture is stirred for 3 hours at room temperature under nitrogen. The poly-Hünig base is filtered off, washed with dioxan and the filtrate is concentrated in vacuo. The crude 2-[(4R,S)-4-ethylthiothiocarbonylthio-2-oxo-1-azetidinyl]-2-chloroacetic acid p-nitrobenzyl ester obtained can be used in the next stage without further purification.

(b) The crude 2[(4R,S)-4-ethylthiothiocarbonylthio-2-oxo-1-azetidinyl]-2-chloroacetic acid p-nitrobenzyl ester obtained is dissolved in 54 ml of absolute dioxan, 4.55 g of poly-Hünig base and then 1.42 g of triphenylphosphine are added and the mixture is stirred for 15 hours at 50° under nitrogen. The poly-Hünig base is filtered off, washed with dioxan and the filtrate and washing liquid are concentrated together in vacuo. The residue is chromatographed over 60 g of silica gel with toluene/ethyl acetate (7:3) and yields the title compound with the following physico-chemical properties:

TLC: $R_f=0.43$ (toluene/ethyl acetate 2:3); IR spectrum ($CH_2Cl_2$): absorption bands at 5.67, 6.15, 6.57, 6.97, 7.43 and 9.05µ.

EXAMPLE 71

(5R,S)-2-Ethylthio-2-penem-3-carboxylic acid p-nitrobenzyl ester

A solution of 9.8 g (14.85 mmol) of 2[(4R,S)-4-ethylthiothiocarbonylthio-2-oxo-1-azetidinyl]-2-triphenylphosphoranylideneacetic acid p-nitrobenzyl ester in 3 l of dry o-xylene is stirred under reflux for 10 hours under nitrogen. The solvent is evaporated off in vacuo and the residue is chromatographed over 400 g of silica gel with toluene/ethyl acetate (19:1 and then 9:1). The title compound is obtained in the form of colourless crystals by crystallisation from diethyl ether/methylene chloride;

Melting point: 133°–134° C.; TLC: $R_f=0.69$ (toluene/ethyl acetate 2:3); IR spectrum ($CH_2Cl_2$): absorption bands at 5.57, 5.9, 6.22, 6.55, 6.65, 7.42, 7.55, 8.37, 9.0 and 9.7µ; NMR spectrum (in $CDCl_3$/100 Mc, in ppm): 8.25–8.15, 2H, m; 7.65–7.55, 2H, m; 5.7, 1H, m; 5.32, 2H, m(AB); 3.9–3.4, 2H, m; 3.1–2.8, 2H, m; 2.3–1.5, 3H, t.

The reaction may alternatively be carried out in boiling toluene, the reaction time of course being prolonged to 120 hours. If desired, a catalytic amount of hydroquinone can be added to the reaction solution.

EXAMPLE 72

(5R,S)-2-Ethylthio-2-penem-3-carboxylic acid 40 ml of 0.2 M aqueous sodium bicarbonate solution and 2 g of 10% palladium/carbon catalyst are added to a solution of 1 g (2.73 mmol) of (5R,S)-2-ethylthio-2-penem-3-carboxylic acid p-nitrobenzyl ester in 70 ml of absolute ethyl acetate and the mixture is stirred at normal pressure for 50 minutes under hydrogen. The hydrogenated mixture is filtered off from the catalyst over diatomaceous earth, the residue is washed with 0.2 N sodium bicarbonate solution and washed several times with ethyl acetate. The aqueous phase is washed with methylene chloride, acidified with 5% aqueous citric acid solution and exhaustively extracted with methylene chloride. The combined organic phases are dried over sodium sulphate, filtered, concentrated in vacuo, and dried under high vacuum. The title compound obtained has the following physico-chemical properties:

Melting point: 143°–145° (from diethyl ether/acetone); TLC: $R_f$=0.27 (toluene/ethyl acetate/acetic acid 60:40:5); IR spectrum (KBr): absorption bands at 3.6–3.3, 5.6, 6.0, 6.75, 6.97, 7.5, 7.9, 8.15 and 8.8$\mu$; NMR spectrum (DMSO d6/100 Mc, in ppm): 5.75, 1H, m; 4–3.3, 2H, m; 3.1–2.8, 2H, m; 1.4–1.2, 3H, t.

EXAMPLE 73

(4R,S)-4-(cis-2-Methoxycarbonylvinylthio)-azetidin-2-one 2 ml of precooled 1 N sodium hydroxide solution are slowly added to a solution, cooled to −15° to −10°, of 206 mg (1.05 mmol) of cis-2-methoxycarbonylvinylisothiouronium hydrochloride (E. G. Kako et al., J. Org. Chem. USSR, 1969, 610, English edition) in 2 ml of methanol, and then, at approximately −12°, 130 mg (1 mmol) of (4R,S)-4-acetoxyazetidin-2-one dissolved in 1 ml of methanol are slowly added. The reaction mixture is stirred for 30 minutes at −10°, diluted with water, saturated with common salt and extracted with ethyl acetate. The combined ethyl acetate extracts are dried with sodium sulphate and concentrated in vacuo. The residue is chromatographed over silica gel with toluene-/ethyl acetate (2:1) and yields the title compound, which after recrystallisation from hot benzene has a melting point of 92°–93°.

IR spectrum (in $CH_2Cl_2$): absorption bands at 5.6, 5.9, 6.3, 8.2 and 8.5$\mu$.

EXAMPLE 74

2-[(4R,S)-4-(cis-2-methoxycarbonylvinylthio)-2-oxo-1-azetidinyl]-2-hydroxyacetic acid acetonyl ester 1.66 g (12.5 mmol) of glyoxylic acid acetonyl ester and 15 g of well dried molecular sieves A4 are added to a solution of 936 mg (5 mmol) of (4R,S)-4-(cis-2-methoxycarbonylvinylthioazetidin-2-one in 5 ml of dry dimethylformamide and 10 ml of xylene and the mixture is stirred overnight at room temperature. The molecular sieves are filtered off and washed with 30 ml of dry tetrahydrofuran. The filtrate and washing liquid are concentrated together in vacuo, and the residue is evaporated a few times again in a vacuum of less than 0.01 mm Hg at 80° with xylene. The amorphous title compound obtained has in the IR spectrum ($CH_2Cl_2$) absorption bands 5.6, 5.75, 5.85, 6.8 and 7.3$\mu$.

The glyoxylic acid acetonyl ester is produced as follows:

(a) 35 ml of chloroacetone is slowly added to a suspension of 32 g of disodium fumarate in 300 ml of dry dimethylformamide and the mixture is then stirred overnight at 100°. The reaction mixture is cooled, 1.52 l of methylene chloride is added and washing is carried out with 1 N hydrochloric acid and water. The organic phase is dried over sodium sulphate, concentrated in vacuo and freed from the rest of the solvent under high vacuum. The fumaric acid diacetonyl ester obtained is recrystallised from methylene chloride/diethyl ether. Melting point: 121°–123°.

(b) A solution of 22.8 g of fumaric acid diacetonyl ester in 400 ml of methylene chloride and 200 ml of methanol is ozonised at −15° for approximately 9 hours until no more starting material can be detected. 100 ml of dimethyl sulphide is added to the ozonised mixture which is allowed to stand overnight at room temperature. Evaporation of the solvent in vacuo and distillation of the residue at 70°–80°/0.05 mm Hg yields the glyoxylic acid acetonyl ester.

EXAMPLE 75

2-[(4R,S)-4-(cis-2-Methoxycarbonylvinylthio)-2-oxo-1-azetidinyl]-2-chloroacetic acid acetonyl ester.

While stirring, 0.43 ml (6 mmol) of thionyl chloride and subsequently, over a period of 5 minutes, a solution of 0.83 ml (6 mmol) of triethylamine in 2 ml of dry tetrahydrofuran are added to a solution, cooled to −15°, of 1.7 g of 2-[(4R,S)-4-(cis-2-methoxycarbonylvinylthio)-2-oxo-1-azetidinyl]-2-hydroxyacetic acid acetonyl ester in 25 ml of dry tetrahydrofuran. The reaction mixture is stirred for a further 15 minutes at 0°, 150 ml of cold methylene chloride are added and washing is carried out with hydrochloric acid/ice water. The organic phase is dried over sodium sulphate and concentrated in vacuo. The residue is chromatographed over 60 g of silica gel with toluene/ethyl acetate 1:1 and yields the title compound. IR spectrum (in $CH_2Cl_2$): absorption bands at 5.6, 5.75, 5.85, 7.3, 8.15 and 8.5$\mu$.

EXAMPLE 76

2-[(4R,S)-4-(cis-2-Methoxycarbonylvinylthio)-2-oxo-1-azetidinyl]-2-triphenylphosphoranylideneacetic acid acetonyl ester 1.73 g (6.6 mmol) of triphenylphosphine is added to a solution of 1.15 g (3.3 mmol) of 2-[(4R,S)-4-(cis-2-methoxycarbonylvinylthio)-3-oxo-1-azetidinyl]-2-chloroacetic acid acetonyl ester in 3 ml of dry tetrahydrofuran and the mixture is allowed to stand at room temperature for 15 hours in a nitrogen atmosphere. The reaction mixture is diluted with 50 ml of methylene chloride, washed with cold, saturated aqueous sodium bicarbonate solution, dried over sodium sulphate and concentrated in vacuo. The residue is chromatographed over 40 g of silica gel with toluene/ethyl acetate (1:1) and yields the title compound.

IR spectrum (in $CH_2Cl_2$): absorption bands at 5.65, 5.85, 6.1 and 6.3$\mu$.

EXAMPLE 77

(5R,S)-2-Penem-3-carboxylic acid acetonyl ester 1 ml of trifluoroacetic acid is added at −20° to a solution of 1.15 g (2 mmol) of 2-[(4R,S)-(cis-2-methoxycarbonylvinylthio)-2-oxo-1-azetidinyl]-2-triphenylphosphoranylideneacetic acid acetonyl ester in 30 ml of dry methylene chloride, whereupon an ozone/oxygen current (0.33 mmol $O_3$/minute) is passed through for a period of 10 minutes. The ozonised solution is rinsed with nitrogen, 1.5 ml of dimethyl sulphide is added, and, after warming to room temperature, the mixture is shaken with 30 ml of methylene chloride and 60 ml of cold, saturated, aqueous sodium bicarbonate solution. The organic phase is separated off, washed again with 20 ml of cold, saturated, aqueous sodium bicarbonate solution, dried over sodium sulphate and concentrated in vacuo. The colourless foam, containing the 2-[(4R,S)-4-formylthio-2-oxo-1-azetidinyl]-2-triphenylphosphoranylideneacetic acid acetonyl ester, is dried under high vacuum, heated under reflux for 30 minutes in 50 ml of dry acid-free methylene chloride and freed of solvent in vacuo. The residue is chromatographed over 20 g of silica gel with toluene/ethyl acetate (1:1) and yields the title compound. A sample recrystallised from methylene chloride/diethyl ether has a melting point of 115°-116°. IR spectrum (in $CH_2Cl_2$): absorption bands at 5.55, 5.75 (sh); 5.8 and 6.4μ; NMR spectrum (in $CDCl_3$/100 Mc, in ppm): 2.2, 3H, s; 3.7, 2H, m; 4.8, 2H, s; 5.8, 1H, m; 7.4, 1H, s.

EXAMPLE 78

(5R,S)-2-Penem-3-carboxylic acid 1 ml of 0.1 N aqueous sodium hydroxide solution is added at 0° over a period of 30 minutes to a solution of 23 mg (0.1 mmol) of (5R,S)-2-penem-3-carboxylic acid acetonyl ester in 3 ml of tetrahydrofuran and the mixture is stirred for 15 minutes at the same temperature. The reaction mixture is washed with 2 ml of diethyl ether and shaken with 20 ml of methylene chloride and 0.5 ml of 20% aqueous citric acid. The organic phase is dried over sodium sulphate and concentrated in vacuo. The residue is digested with methylene chloride and the crystals are filtered off.

Melting point: 230°; TLC: $R_f$=0.3 (acetic acid/toluene/water 5:5:1); IR spectrum (in KBr): absorption bands at 5.6, 5.95, 6.45, 6.9 and 12.2μ; NMR spectrum (in DMSO d6/100 Mc, in ppm): 3.7, 2H, m; 5.8, 1H, m; 7.6, 1H, s.

EXAMPLE 79

(4R,S)-, (4R)- and (4S)-4-[cis-2-(1)-menthyloxycarbonylvinylthio]-azetidin-2-one 2 ml of 1 N aqueous sodium hydroxide solution and then 130 mg (1 mmol) of (4R,S)-4-acetoxyazetidin-2-one dissolved in 2 ml of ethanol are slowly added to a solution, cooled to −10°, of 321 mg (1 mmol) of cis-2-(1)-menthyloxycarbonylvinylisothiouronium hydrochloride in 4 ml of ethanol. The reaction mixture is stirred for 15 minutes at −10° and for 15 minutes at room temperature and extracted with methylene chloride. The organic phase is dried over sodium sulphate and concentrated in vacuo. The residue is chromatographed over 10 g of silica gel with toluene/ethyl acetate (2:1) and yields the (4R,S)-title compound in crystalline form.

The pure (4S)-isomer is obtained by recrystallising the (4R,S)-compound from methylene chloride/pentane at 0°. Further quantities of this isomer can be obtained by recrystallisation of the mother liquor from methanol at −70°. Melting point: 134°-135°; $[\alpha]_D^{20}$= −82°±0.2° (c=1%, $CHCl_3$); TLC: $R_f$=0.2 (toluene/ethyl acetate 1:1); IR spectrum (in $CH_2Cl_2$): absorption bands at 2.95, 3.4, 5.6, 5.9, 8.2 and 8.5μ.

The pure (4R)-isomer is obtained from the combined mother liquors by repeated (6 times) recrystallisation from methanol at −70° and finally from methylene chloride/pentane at 0°. Melting point: 139°-141°; $[\alpha]_D^{20}$= −91°±1°(c=1%; $CHCl_3$).

The isothiouronium salt used is produced as follows:

(a) 8 drops of concentrated sulphuric acid are added to a solution of 62.4 g of (1)-menthol and 42 g of propiolic acid in 120 ml of benzene, and the mixture is boiled under reflux in a water separator for 2½ days. After separating approximately 9.5 ml of water, the benzene solution is diluted with 120 ml of benzene, washed in succession with saturated aqueous sodium bicarbonate solution and saturated aqueous sodium chloride solution, dried over sodium sulphate and concentrated in vacuo. The faintly-yellow residue is chromatographed over 1 kg of silica gel with toluene/ethyl acetate (19:1) and yields the propiolic acid (1)-menthyl ester; melting point 90°-92°; $[\alpha]_D^{20}$= −82°±1°(c=1%; $CHCl_3$).

(b) A solution of 0.76 g (10 mmol) of thiourea in a mixture of 5 ml of 2 N hydrochloric acid and 5 ml of ethanol is slowly added to a solution of 2.04 g (10 mmol) of propiolic acid (1)-menthyl ester in 10 ml of ethanol so that the temperature does not exceed 40°. The reaction mixture is stirred at room temperature until clear and concentrated in vacuo. The residue is washed with acetone on a glass suction filter, recrystallised from hot water and the crystals obtained after filtration are washed with acetone. A sample, recrystallised from isopropanol, of the cis-2-(1)-menthyloxycarbonylvinylisothiouronium hydrochloride obtained has a melting point of 176°-179°; $[\alpha]_D^{20}$= −74°±1° (c=1%; ethanol).

EXAMPLE 80

(4S)- and (4R)-4-[trans-2-(1)-menthyloxycarbonylvinylthio]-azetidin-2-one

A solution of 64 mg (0.2 mmol) of (4S)-4-(cis-2-(1)-menthyloxycarbonylvinylthio)-azetidin-2-one in 1.5 ml of octane is refluxed at a bath temperature of 150° for 90 minutes. Chromatography over silica gel of the cis-trans-(1:4)-isomeric mixture obtained yields the quicker running trans-isomer; $[\alpha]_D^{20}$= −159°±1° (c=1%; $CHCl_3$); TLC: $R_f$=0.4 (toluene/ethyl acetate 1:1); IR spectrum (in $CH_2Cl_2$): absorption bands at 2.95, 3.4, 5.6, 5.85, 6.25 and 8.5μ.

Using (4R)-4-(cis-2-(1)-menthyloxycarbonylvinylthio)-azetidin-2-one as the starting material, (4R)-4-(trans-2-(1)-menthyl-oxycarbonylvinylthio)-azetidin-2-one is obtained in the same manner.

$[\alpha]_D^{20}$= +26°±1° (c=1%; $CHCl_3$); TLC: $R_f$=0.4 (toluene/ethyl acetate 1:1); IR spectrum (in $CHCl_3$): absorption bands at 2.95, 3.4, 5.6, 5.85, 6.25 and 8.5μ.

EXAMPLE 81

2-[(4S)-(cis-2-(1)-menthyloxycarbonylvinylthio)-2-oxo-1-azetidinyl]-2-hydroxyacetic acid acetonyl ester.

12 g of molecular sieves A4 are added to a mixture of 935 mg (3 mmol) of (4S)-4-(cis-2-(1)-menthyloxycarbonylvinylthio)-azetidin-2-one and 1 g (7.5 mmol) of glyoxylic acid acetonyl ester in 3 ml of dry dimethylformamide and 6 ml of toluene, and the mixture is stirred overnight at room temperature. The molecular sieves are filtered off, washed with dry tetrahydrofuran and the filtrate and washing liquid are concentrated together in vacuo and dried under high vacuum at 70°.

The residue is evaporated several times in vacuo with xylene, and is used in the subsequent reaction without further purification.

IR spectrum (in CH$_2$Cl$_2$): absorption bands at 5.6, 5.75, 5.9, 6.3, 8.15 and 8.5µ.

EXAMPLE 82

2-[(4R)-(cis-2-(1)-Menthyloxycarbonylvinylthio)-2-oxo-1-azetidinyl]-2-hydroxyacetic acid acetonyl ester Using (4R)-4-(cis-2-(1)-menthyloxycarbonylvinylthio)-azetidin-2-one as starting material, the (4R)-isomer is obtained in a manner analogous to that in Example 81. IR spectrum (in CH$_2$Cl$_2$): absorption bands at 5.6, 5.75, 5.9, 6.3, 8.15 and 8.5µ.

EXAMPLE 83

2-[(4S)-(trans-2-(1)-Menthyloxycarbonylvinylthio)-2-oxo-1-azetidinyl]-2-hydroxyacetic acid acetonyl ester Using (4S)-4-(trans-2-(1)-menthyloxycarbonylvinylthio)-azetidin-2-one as starting material, the (4S)-trans-isomer is produced in a manner analogous to that in Example 81. IR spectrum: the same absorption bands as in Example 82.

EXAMPLE 84

2-[(4R)-(trans-2-(1)-Menthyloxycarbonylvinylthio)-2-oxo-1-azetidinyl]-2-hydroxyacetic acid acetonyl ester Using (4R)-4-(trans-2-(1)-menthyloxycarbonylvinylthio)azetidinone as starting material, the (4R)-trans-isomer is produced in a manner analogous to that in Example 81. IR spectrum: the same absorption bands as in Example 82.

EXAMPLE 85

2-[(4S)-4-(cis-2-(1)-Menthyloxycarbonylvinylthio)-2-oxo-1-azetidinyl]-2-chloroacetic acid acetonyl ester While stirring, 0.26 ml (3.6 mmol) of thionyl chloride and, over a period of 5 minutes, a solution of 0.5 ml (3.6 mmol) of triethylamine in 1.5 ml of tetrahydrofuran, are added to a solution, cooled to −15°, of 1.54 g of 2-[(4S)-4-(cis-2-(1)-menthyloxycarbonylvinylthio)-2-oxo-1-azetidinyl]-2-hydroxyacetic acid acetonyl ester in 15 ml of dry tetrahydrofuran. The reaction mixture is stirred for a further 15 minutes at 0°, 100 ml of cold methylene chloride are added and the mixture is washed with 30 ml of ice-cold aqueous hydrochloric acid. The organic phase is dried over sodium sulphate and concentrated in vacuo. The residue is chromatographed over 40 g of silica gel with toluene/ethyl acetate (1:1) and yields the title compound.

IR spectrum (in CH$_2$Cl$_2$): absorption bands at 3.4, 5.6, 5.75, 5.9, 6.3, 8.2 and 8.5µ.

EXAMPLE 86

2-[(4R)-4-(cis-2-(1)-Menthyloxycarbonylvinylthio)-2-oxo-1-azetidinyl]-2-chloroacetic acid acetonyl ester Using 2-[(4R)-4-(cis-2-(1)-menthyloxycarbonylvinylthio)-2-oxo-1-azetidinyl]-2-hydroxyacetic acid acetonyl ester as starting material, the (4R)-isomer is produced in a manner analogous to that in Example 85.

IR spectrum (in CH$_2$Cl$_2$): absorption bands at 3.4, 5.6, 5.75, 5.9, 6.3, 8.2 and 8.5µ.

EXAMPLE 87

2-[(4S)-4-(trans-2-(1)-Menthyloxycarbonylvinylthio)-2-oxo-1-azetidinyl]-2-chloroacetic acid acetonyl ester Using 2-[(4S)-4-(trans-2-(1)-menthyloxycarbonylvinylthio)-2-oxo-1-azetidinyl]-2-hydroxyacetic acid acetonyl ester as starting material, the (4S)-trans-isomer is produced in a manner analogous to that in Example 85.

IR spectrum (in CH$_2$Cl$_2$): absorption bands at 3.4, 5.6, 5.75, 5.9, 6.3, 8.2 and 8.5µ.

EXAMPLE 88

2-[(4R)-4-(trans-2-(1)-Menthyloxycarbonylvinylthio)-2-oxo-1-azetidinyl]-2-chloroacetic acid acetonyl ester Using 2-[(4R)-4-(cis-2-(1)-menthyloxycarbonylvinylthio)-2-oxo-1-azetidinyl]-2-hydroxyacetic acid acetonyl ester as starting material, the (4R)-trans-isomer is produced in a manner analogous to that in Example 85.

IR spectrum (in CH$_2$Cl$_2$): absorption bands at 3.4, 5.6, 5.75, 5.9, 6.3, 8.2 and 8.5µ.

EXAMPLE 89

2-[(4S)-4-(cis-2-(1)-Menthyloxycarbonylvinylthio)-2-oxo-1-azetidinyl]-2-triphenylphosphoranylideneacetic acid acetonyl ester 1.57 g (6 mmol) of triphenylphosphine is added to a solution of 1.40 g (3.3 mmol) of 2-[(4S)-4-(cis-2-(1)-menthyloxycarbonylvinylthio)-2-oxo-1-azetidinyl]-2-chloroacetic acid acetonyl ester in 2.5 ml of dry tetrahydrofuran, and the mixture is allowed to stand at room temperature for 24 hours in a nitrogen atmosphere. The reaction mixture is diluted with 50 ml of methylene chloride, washed with 20 ml of cold, saturated, aqueous sodium bicarbonate solution, dried over sodium sulphate and concentrated in vacuo. The residue is chromatographed over 40 g of silica gel with toluene/ethyl acetate (1:1 and 1:2) and yields the title compound, which is contaminated with approximately 10% of the quicker-running corresponding trans-compound.

IR spectrum (in CH$_2$Cl$_2$): absorption bands at 5.7, 5.9, 6.15 and 6.85µ; NMR spectrum (in CDCl$_3$/100 Mc, in ppm): 5.9, d, 1H, J=10 Hz (ROOC—CH=).

EXAMPLE 90

2-[(4R)-4-(cis-2-(1)-Menthyloxycarbonylvinylthio)-2-oxo-1-azetidinyl]-2-triphenylphosphoranylideneacetic acid acetonyl ester Using 2-[(4R)-4-(cis-2-(1)-menthyloxycarbonylvinylthio)-2-oxo-1-azetidinyl]-2-chloroacetic acid acetonyl ester as starting material, the (4R)-cis-isomer is produced in a manner analogous to that in Example 89.

IR spectrum (in CH$_2$Cl$_2$): absorption bands at 5.7, 5.9, 6.15 and 6.85µ; NMR spectrum: the same bands as in Example 89.

EXAMPLE 91

2-[(4S)-4-(trans-2-(1)-Menthyloxycarbonylvinylthio)-2-oxo-1-azetidinyl]-2-triphenylphosphoranylideneacetic acid acetonyl ester Using 2-[(4S)-4-(trans-2-(1)-menthyloxycarbonylvinylthio)-2-oxo-1-azetidinyl]-2-chloroacetic acid acetonyl ester as starting material, the (4S)-trans-isomer is produced in a manner analogous to that in Example 89.

IR spectrum (in CH$_2$Cl$_2$): absorption bands at 5.7, 5.9, 6.15 and 6.85μ; NMR spectrum (in CDCl$_3$/100 Mc, in ppm): 5.8, d, 1H, J=15 Hz (ROOC—CH=).

EXAMPLE 92

2-[(4R)-4-(trans-2-(1)-Menthyloxycarbonylvinylthio)-2-oxo-1-azetidinyl]-2-triphenylphosphoranylideneacetic acid acetonyl ester Using 2-[(4R)-4-(trans-2-(1)-Menthyloxycarbonylvinylthio)-2-oxo-1-azetidinyl]-2-chloroacetic acid acetonyl ester as starting material, the (4R)-trans-isomer is produced in a manner analogous to that in Example 89.

IR spectrum (in CH$_2$Cl$_2$) absorption bands at 5.7, 5.9, 6.15 and 6.85μ; NMR spectrum: the same bands as in Example 91.

EXAMPLE 93

(5S)-2-Penem-3-carboxylic acid acetonyl ester 1 ml of trifluoroacetic acid is added at −20° to a solution of 1.38 g (2 mmol) of 2-[(4S)-(cis-2-(1)-menthyloxycarbonylvinylthio)-2-oxo-1-azetidinyl]-2-triphenylphosphoranylideneacetic acid acetonyl ester in 30 ml of dry methylene chloride, whereupon an ozone/oxygen current (0.33 mmol O$_3$/minute) is passed through for a period of 10 minutes. The ozonised solution is rinsed with nitrogen, 1.5 ml of dimethyl sulphide is added, and after warming to room temperature the mixture is shaken with 30 ml of methylene chloride and 60 ml of cold, saturated, aqueous sodium bicarbonate solution. The organic phase is separated, washed again with 15 ml of cold, saturated, aqueous sodium bicarbonate solution, dried over sodium sulphate and concentrated in vacuo. The colourless foam, containing the 2-[(4S)-4-formylthio-2-oxo-1-azetidinyl]-2-triphenylphosphoranylideneacetic acid acetonyl ester, is dried under high vacuum, heated under reflux in an argon atmosphere in 50 ml of dry, acid-free methylene chloride for 75 minutes and freed of solvent in vacuo. The residue is chromatographed over 20 g of silica gel with toluene/ethyl acetate (3:1) and yields the title compound, which, recrystallised from methylene chloride/diethyl ether/pentane, has a melting point of 105°–107°.

IR spectrum (in CH$_2$Cl$_2$): absorption bands at 5.55, 5.75 (sh), 5.8, 6.4, 8.25 and 8.5μ; NMR spectrum (in CDCl$_3$/100 Mc, in ppm): 2.2, 3H, s; 3.7, 2H, m; 4.8, 2H, s; 5.8, 1H, m; 7.4, 1H, s, $[\alpha]_D^{20}$=−249°±0.5° (c=1%, CHCl$_3$).

The same compound is obtained if 2-[(4S)-(trans-2-(1)-menthyloxycarbonylvinylthio)-2-oxo-1-azetidinyl]-2-triphenylphosphoranylideneacetic acid acetonyl ester is reacted in an analogous manner.

EXAMPLE 94

(5R)-2-Penem-3-carboxylic acid acetonyl ester

Using 2-[(4R)-(cis-2-(1)-menthyloxycarbonylvinylthio)-2-oxo-1-azetidinyl]-2-triphenylphosphoranylideneacetic acid acetonyl ester as starting material, the (5R)-title compound is produced in a manner analogous to that in Example 93.

Melting point 93°–94°; IR spectrum (in CH$_2$Cl$_2$): absorption bands at 5.55, 5.8, 6.4, 8.25 and 8.5μ; NMR spectrum (in CDCl$_3$/100 Mc, in ppm): 2.2, 3H, s; 3.7, 2H, m; 4.8, 2H, s; 5.8, 1H, m; 7.4, 1H, s; $[\alpha]_D^{20}$=+251°±1° (c=1%, CHCl$_3$).

The same compound is obtained if the 2-[(4R)-(trans-2-(1)-menthyloxycarbonylvinylthio)-2-oxo-1-azetidinyl]-2-triphenylphosphoranylideneacetic acid acetonyl ester is reacted in a similar manner.

EXAMPLE 95

(5S)-2-Penem-3-carboxylic acid 4 ml of 0.1 N aqueous sodium hydroxide solution is added dropwise at 0° in a period of 15 minutes to a solution of 91 mg (0.4 mmol) of (5S)-2-penem-3-carboxylic acid acetonyl ester in 9 ml of tetrahydrofuran and 1 ml of water and the mixture is stirred for a further 30 minutes at the same temperature. The reaction mixture is diluted with 4 ml of water, washed with 8 ml of diethyl ether and shaken with 80 ml of methylene chloride and 2 ml of 20% aqueous citric acid. The organic phase is dried over sodium sulphate and concentrated in vacuo. The residue is chromatographed over 4 g of silica gel with methylene chloride/glacial acetic acid (9:1). The fractions containing the title compound are evaporated under high vacuum together with toluene and yield the crystalline product having a melting point of >300°; IR spectrum (in CH$_2$Cl$_2$): absorption bands at 5.55, 5.9 and 6.4μ; $[\alpha]_D^{20}$=−383° (c=1%, CH$_2$Cl$_2$).

EXAMPLE 96

(5R)-2-Penem-3-carboxylic acid

Using (5R)-2-penem-3-carboxylic acid acetonyl ester as starting material, the (5R)-title compound is obtained in a manner analogous to that in Example 95.

Melting point: >300°; IR spectrum (in CH$_2$Cl$_2$): absorption bands at 5.55, 5.9 and 6.4μ; $[\alpha]_D^{20}$=+384°±1° (c=1%, CH$_2$Cl$_2$).

EXAMPLE 97

Penicillanic acid methyl ester 1-oxide

A solution of 6.5 g of penicillanic acid methyl ester (produced by catalytic hydrogenation of 6α-bromopenicillanic acid methyl ester by means of 5% palladium/barium carbonate catalyst in aqueous dioxan) in 220 ml of methylene chloride is cooled to −15° under nitrogen, a solution of 6.14 g of 18% m-chloroperbenzoic acid (30.23 mmol) in 140 ml of methylene chloride is added dropwise and the mixture is stirred for 2 hours at the same temperature. The reaction mixture is diluted with methylene chloride, washed in succession with 3% aqueous sodium bisulphite solution and 8% aqueous sodium bicarbonate solution, and dried over sodium sulphate. The solvent is evaporated off in vacuo and the residue is used in the subsequent reaction in this crude form. A sample is chromatographed over silica gel (10% H$_2$O). With toluene/ethyl acetate (2:1) the title compound is obtained in the form of an oil, which after repeating the purification by thin layer chromatography over silica gel plates with toluene/ethyl acetate (1:1) has the following physicochemical properties:

$[\alpha]_D^{20}$=+280°±1° (c=1.005% in CHCl$_3$); IR spectrum (in methylene chloride): characteristic absorption bands at 3.25-3.50, 5.61, 5.72, 6.86, 7.00, 7.10 (sh), 7.21, 7.32, 7.42, 7.81-8.01 (broad), 8.22 (sh), 8.30-8.36, 8.47 (sh), 9.21, 9.46, 9.88 (sh) and 9.96μ; NMR spectrum (in CDCl$_3$/100 Mc, in ppm): 1.23, 3H, s; 1.70, 3H, s; 3.34, 2H, d; 3.80, 3H, s; 4.51, 1H, s; 4.97, 1H, t.

EXAMPLE 98

2-[(4R)-4-(Benzthiazol-2-yldithio)-2-oxoazetidin-1-yl]-3-methylenebutyric acid methyl ester A solution of 685 mg of penicillanic acid methyl ester 1-oxide and 496 mg (2.97 mmol) of 2-mercaptobenz-thiazole in 30 ml of toluene is heated under reflux for 2.5 hours. The solvent is distilled off in vacuo and the residue is chromatographed over 60 g of silica gel. The title compound is obtained in amorphous form by elution with toluene/ethyl acetate (9:1).

TLC: $R_f=0.47$ (ethyl acetate/toluene 1:1); IR spectrum (in methylene chloride): absorption bands at 5.66, 5.75, 5.97-6.05, 6.75 (sh), 6.84, 7.03, 7.28, 7.53, 7.60 (sh), 7.65 (sh); 8.10, 8.35, 8.50, 8.89, 9.25, 9.81 and 9.93μ; $[\alpha]_D^{20}=-392°\pm1°$ (c=0.777% in CHCl$_3$).

EXAMPLE 99

2-[(4R)-4-(Benzthiazol-2-yldithio)-2-oxoazetidin-1-yl]-3-methylcrotonic acid methyl ester 5 ml of triethylamine are added to a solution of 12 g of 2-[(4R)-4-(benzthiazol-2-yldithio)-2-oxoazetidin-1-yl]-3-methylenebutyric acid methyl ester in 500 ml of methylene chloride and the mixture is allowed to stand at room temperature for 90 minutes. The reaction mixture is washed with 5% aqueous citric acid solution, dried over sodium sulphate and freed of solvent in vacuo. The residue is purified by chromatography over silica gel (deactivated with 10% water) with toluene and toluene/ethyl acetate (19:1) and yields the title compound, which after recrystallisation from diethyl ether/pentane has a melting point of 63°-66°.

TLC: $R_f=0.44$ (ethyl acetate/toluene 1:1); IR spectrum (in methylene chloride): characteristic absorption bands at 3.35-3.60, 5.66, 5.81, 5.87 (sh), 5.93 (sh), 6.15, 6.85, 7.04, 7.26, 7.36, 7.65 (sh), 7.73, 8.17, 8.25 (sh), 8.35 (sh), 8.90, 9.18 (sh), 9.26, 9.42 (sh), 9.81 (sh), 9.92, 10.25 and 10.95 (broad) μ; $[\alpha]_D^{20}=-153°\pm1°$ (c=0.916%, in CHCl$_3$).

EXAMPLE 100

2-[(4R)-4-Acetylthio-2-oxoazetidin-1-yl]-3-methylcrotonic acid methyl ester (a) A solution of 4.6 g of 2-[(4R)-4-benzthiazol-2-yldithio)-2-oxoazetidin-1-yl]-3-methylcrotonic acid methyl ester in 120 ml of dimethylformamide is cooled to −20°, a solution of 670 mg of sodium borohydride in 80 ml of dimethylformamide is added and the mixture is stirred for 10 minutes at the same temperature. The temperature of the reaction mixture is increased to 0° for 60 minutes, then cooled again to −20°, whereupon 40 ml of freshly distilled acetyl bromide are added dropwise and the mixture is further stirred at 0° for 2 hours. After adding 1.5 l of benzene, the reaction mixture is washed in succession with ice water, water, 8% aqueous sodium bicarbonate solution and water, dried over sodium sulphate and concentrated in vacuo. After chromatography over silica gel (deactivated with 10% water) with toluene and toluene/ethyl acetate (19:1), the residue yields the title compound which is slightly contaminated by the (4S)-enantiomer. Repeated chromatography and recrystallisation from diethyl ether/pentane yields the pure title compound having a melting point of 81°-82°; $[\alpha]_D^{20}=+149°\pm1°$ (c=0.994%, CHCl$_3$); TLC: $R_f=0.40$ (ethyl acetate/toluene 1:1); IR spectrum (in methylene chloride): absorption bands at 3.35-3.57, 5.66, 5.81, 5.89, 5.96 (sh), 6.15, 7.00, 7.07 (sh), 7.25, 7.35, 7.72, 8.15, 8.22 (sh), 8.35 (sh), 8.86, 9.15, 9.26, 9.42, 9.95, 10.11, 10.50 (broad) and 10.80μ.

(b) The partial racemisation can be prevented by the following method of operation:

1 g of zinc powder is added in portions over a period of one hour to a solution, stirred under nitrogen and in an ice bath, of 380 mg (1 mmol) of 2-[(4R)-4-(benzthiazol-2-yl-dithio)-2-oxoazetidin-1yl]-3-methylcrotonic acid methyl ester in 3 ml of acetic anhydride and 5 ml of glacial acetic acid. The reaction mixture is further stirred for one hour at room temperature, filtered and concentrated in vacuo. The residue is taken up in methylene chloride and washed in succession with 25% aqueous ammonium chloride solution and aqueous sodium bicarbonate solution. The combined aqueous phases are reextracted with methylene chloride, all the methylene chloride phases are combined, dried with sodium sulphate and concentrated in vacuo. The residue is chromatographed over 40 g of silica gel (deactivated with 10% water) with toluene and toluene/ethyl acetate (19:1) and yields the optically pure title compound having a melting point of 78°-80°; $[\alpha]_D^{20}=+149°\pm1°$ (c=1.007%; in CHCl$_3$).

EXAMPLE 101

2-[(4R)-4-Acetylthio-2-oxoazetidin-1-yl]-2-oxoacetic acid methyl ester 4 equivalents of ozone are introduced over a period of 60 minutes into a solution, cooled to −15°, of 150 mg of 2-[(4R)-4-acetylthio-2-oxoazetidin-1-yl]-3-methylcrotonic acid methyl ester in 3 ml of methanol. The reaction mixture is rinsed with nitrogen, diluted with methylene chloride and washed for 2 minutes with a 5% aqueous sodium bisulphite solution. The organic phase is dried over sodium sulphate and concentrated in vacuo. IR spectrum of the resulting oily title compound (in methylene chloride): characteristic bands at 3.30-3.40, 5.52, 5.70, 5.83 (sh), 5.86, 6.98, 7.08 (sh), 7.40, 7.82-8.00 (broad, sh), 8.07, 8.19, 8.30 (sh), 8.46, 8.90, 9.22, 9.52, 9.91, 10.30 and 10.73μ.

The produce obtained can be used in the next stage without further purification.

EXAMPLE 102

(4R)-4-Acetylthio-2-oxoazetidine

A solution of 140 mg of 2-[(4R)-4acetylthio-2-oxoazetidin-1-yl]-2-oxoacetic acid methyl ester (crude product) in a mixture of 20 ml of methanol, 2 ml of methyl acetate and 0.4 ml of water is allowed to stand for 20 hours at room temperature, concentrated in vacuo and evaporated again with benzene. The residue is chromatographed over silica gel thick layer plates with toluene/ethyl acetate (2:1) and yields the title compound.

TLC: $R_f=0.29$ (ethyl acetate/toluene 1:1); IR spectrum (in methylene chloride): characteristic absorption bands at 2.98, 5.62, 5.91, 7.13, 7.41 (sh), 7.46, 7.83-8.15 (broad), 8.62, 8.89, 9.07 (sh), 9.20 (sh), 10.19, 10.58 and 11.05-11.15 (broad)μ; $[\alpha]_D^{20}=+359°\pm1°$ (c=0.947%, in CHCl$_3$).

EXAMPLE 103

2-[(4R)-4-Acetylthio-2-oxoazetidin-1-yl]-2-hydroxyacetic acid p-nitrobenzyl ester 200 mg of 2-ethoxy-2-hydroxyacetic acid p-nitrobenzyl ester and 2 g of molecular sieves A4 are added to a solution of 54.5 mg of (3S,4R)-4-acetylthio-3-methoxy-2-oxoazetidine in a mixture of 4 ml of toluene and 1 ml of dimethylformamide, and the mixture is stirred for 2 hours at 50°. The molecular sieves are filtered off and the filtrate is concentrated in vacuo. The residue is chromatographed over silica gel, and by elution with toluene/ethyl acetate (9:1) the title compound, contaminated with some glyoxylate, is obtained.

TLC: $R_f$=0.48 (ethyl acetate); IR spectrum (in $CH_2Cl_2$): absorption bands at 2.89 (broad), 5.64, 5.73, 5.91, 6.24, 6.56, 7.44, 7.62, 7.83-8.15 (broad, sh), 8.26, 8.39 and 8.80-9.30 (broad)μ.

EXAMPLE 104

2-[(4R)-4-Acetylthio-2-oxoazetidin-1-yl]-2-triphenyl-phosphoranylideneacetic acid p-nitrobenzyl ester (a) A solution of 2.86 g (~24 mmol) of thionyl chloride in 20 ml of dioxan is added dropwise to a suspension, stirred at room temperature, of 12 g of poly-Hünig base in a solution of 2.83 g (7.59 mmol) of 2-[(4R)-4-acetylthio-2-oxoazetidin-1-yl]-2-hydroxyacetic acid p-nitrobenzyl ester in 100 ml of dioxan. The mixture is stirred for 1.5 hours at room temperature and filtered off from the poly-Hünig base, which is subsequently washed with dioxan. The filtrate is concentrated in vacuo. The 2-[(4R)-4-acetylthio-2-oxoazetidin-1-yl]-2-chloroacetic acid p-nitrobenzyl ester obtained is used in the next stage in crude form.

(b) 3.144 g (~1.5 equivalents) of triphenylphosphine and 12 g of poly-Hünig base are added to a solution of 3.1 g of 2-[(4R)-4-acetylthio-2-oxoazetidin-1-yl]-2-chloroacetic acid p-nitrobenzyl ester in 120 ml of dioxan and the mixture is stirred for 17 hours at 50° under nitrogen. The poly-Hünig base is filtered off, washed with dioxan and the filtrate concentrated in vacuo. The residue is chromatographed twice over silica gel with toluene and toluene/ethyl acetate (4:1 and 3:2) and yields the title compound.

TLC: $R_f$=0.21 (ethyl acetate/toluene 1:1); IR spectrum (in methylene chloride): characteristic absorption bands at 3.30-3.55, 5.70, 5.90, 6.05 (sh), 6.09 (sh), 6.16, 6.22 (sh), 6.57, 6.74, 6.96, 7.05 (sh), 7.20, 7.44, 7.80-8.05 (broad), 8.25, 8.40, 8.85, 9.05 and 9.25μ; $[\alpha]_D^{20}$=+35°±1°(c=1.061% in $CHCl_3$).

EXAMPLE 105

(5R)-2-Methyl-2-penem-3-carboxylic acid p-nitrobenzyl ester

A catalytic amount of hydroquinone is added to a solution of 500 mg of (4R)-2-[4-acetylthio-2-oxoazetidin-1-yl]-2-triphenylphosphoranylideneacetic acid p-nitrobenzyl ester in 500 ml of absolute toluene and the mixture is stirred for 40 hours at 90° under argon. The toluene is evaporated off in vacuo and the residue is chromatographed over 20 g of silica gel with toluene/ethyl acetate (19:1). The title compound is obtained in crystalline form. Melting point: 147.5°-149.5° (from methylene chloride/diethyl ether); TLC: $R_f$=0.54 (ethyl acetate/toluene 1:1); $[\alpha]_D^{20}$=+136°±1° (c=1.034%, in $CHCl_3$); IR spectrum: absorption bands at 3.40-3.55, 5.59, 5.84, 5.95 (sh), 6.22 (sh), 6.30, 6.55, 7.15, 7.28, 7.41, 7.61, 7.69 (sh), 8.28, 8.35, 8.56, 8.63 (sh), 9.02 (sh), 9.10, 9.25, 9.43, 9.62 and 9.84μ.

EXAMPLE 106

(5R)-2-Methyl-2-penem-3-carboxylic acid 140 mg of 10% palladium/carbon catalyst are added to a solution of 100 mg of (5R)-2-methyl-2-penem-3-carboxylic acid p-nitrobenzyl ester in a mixture of 6 ml of ethyl acetate and 4 ml of 0.2 M sodium bicarbonate solution, and the mixture is hydrogenated for 30 minutes at room temperature under atmospheric pressure. After adding a further 70 mg of catalyst, hydrogenation is effected again for 30 minutes. The hydrogenated mixture is filtered through diatomaceous earth; the filter residue is washed with 2 ml of 0.2 M aqueous sodium bicarbonate solution and methyl acetate. The aqueous phase is separated from the filtrate, washed with methylene chloride, acidified with 5% aqueous citric acid and extracted several times with methylene chloride. The combined methylene chloride extracts are dried over sodium sulphate, concentrated in vacuo and recrystallised from acetone at −20°. Melting point: 142°-145° (with decomposition);

$[\alpha]_D^{20}$= +286°±1° (c=0.603%, in acetone); IR spectrum (in KBr): absorption bands at 2.85-4.30 (broad), 5.60 (sh), 5.66, 5.97 (sh), 6.04, 6.42, 6.50 (sh), 7.05 (broad), 7.32, 7.64 (broad), 7.80 (broad), 8.17-8.25 (broad) and 8.40μ; NMR spectrum (in d6-acetone/100 Mc, in ppm): 2.31, 3H, s; 3.39, 1H, dd, $J_1$=16 Hz, $J_2$=2 Hz; 3.82, 1H, dd, $J_1$=16 Hz, $J_3$=4 Hz; 5.69, 1H, dd, $J_2$=2 Hz, $J_3$=4 Hz.

EXAMPLE 107

(4R,S)-4-(Nicotinoylthio)-2-oxoazetidine

A solution of 6.95 g of thionicotinic acid in 50 ml of 1 N sodium hydroxide solution is added dropwise at room temperature under nitrogen to a solution of 5.16 g of (4R,S)-4-acetoxyazetidin-2-one in 30 ml of water (a small excess of sodium hydroxide solution is added to maintain the solution close to a pH of 8) and the mixture is stirred at the same temperature for 1 hour. The reaction mixture is exhaustively extracted with methylene chloride. The combined organic phases are dried over sodium sulphate and concentrated in vacuo. The residue is chromatographed over silica gel with toluene/ethyl acetate (2:3) and yields the title compound having a melting point of 112°-113°.

TLC: $R_f$=0.14 (toluene/ethyl acetate 2:3); IR spectrum ($CH_2Cl_2$): absorption bands at 2.95, 5.6, 5.97, 6.27, 8.15, 8.2, 10.85 and 11.12μ.

EXAMPLE 108

2-[(4R,S)-4-(Nicotinoylthio)-2-oxo-1-azetidinyl]-2-hydroxyacetic acid p-nitrobenzyl ester A solution of 3 g of 2-ethoxy-2-hydroxyacetic acid p-nitrobenzyl ester in 60 ml of dry toluene and 15 ml of dry dimethylformamide is added at room temperature to 1 g (4.8 mmol) of (4R,S)-4-(nicotinoylthio)-2-oxoazetidine. After adding freshly dried molecular sieves, the mixture is stirred under nitrogen for 15 hours at room temperature and then for 2 hours at 50°. The molecular sieves are filtered off, washed with toluene and the filtrate and washing liquid are concentrated together in vacuo. The residue is chromatographed over 200 g of silica gel with toluene/ethyl acetate (9:1 to 6:4). After eluting the unreacted 2-ethoxy-2-hydroxyacetic acid p-nitrobenzyl ester, the title compound having the following physico-chemical properties is eluted:

TLC: $R_f=0.13$ (toluene/ethyl acetate 2:3); IR spectrum (CH$_2$Cl$_2$): absoption bands at 5.62, 5.7, 6.0, 6.55, 7.4 and 8.22μ.

EXAMPLE 109

2-[(4R,S)-4-Nicotinoylthio)-2-oxo-1-azetidinyl]-2-triphenylphosphoranylideneacetic acid p-nitrobenzyl ester.

(a) A solution of 3.6 g (8.64 mmol) of 2-[(4R,S)-4-(nicotinoylthio)-2-oxo-1-azetidinyl]-2-hydroxyacetic acid p-nitrobenzyl ester in 60 ml of absolute dioxan is added to a solution of 13 g of poly-Hünig base in 30 ml of absolute dioxan that has already been stirred for 30 minutes. After adding a solution of 2.5 ml of thionyl chloride in 24 ml of absolute dioxan, the reaction mixture is stirred for one hour at room temperature under nitrogen. The poly-Hünig base is filtered off, washed with dioxan and the filtrate and washing liquid are concentrated together in vacuo.

(b) The crude 2-[(4R,S)-4-(nicotinoylthio)-2-oxo-1-azetidinyl]-2-chloroacetic acid p-nitrobenzyl ester obtained is dissolved in 150 ml of absolute dioxan and stirred overnight at 50° under nitrogen with 12.9 g of poly-Hünig base and 4.5 g of triphenylphosphine. The poly-Hünig base is filtered off, washed with dioxan and the filtrate and washing liquid are concentrated together in vacuo. The residue is chromatographed over 150 g of silica gel with toluene/ethyl acetate (8:2 to 6:4) and yields the title compound with the following physicochemical properties:

TLC: $R_f=0.1$ (toluene/ethyl acetate 2:3); IR spectrum (CH$_2$Cl$_2$): absorption bands at 5.67, 6.0, 6.15, 6.55, 6.95, 7.4, 8.2, 9.05 and 9.25μ.

EXAMPLE 110

(5R,S)-2-Pyrid-3-yl-2-penem-3-carboxylic acid p-nitrobenzyl ester

A catalytic amount of hydroquinone is added to a solution of 2.15 g of 2-[(4R,S)-4-(nicotinoylthio)-2-oxo-1-azetidinyl]-2-triphenylphosphoranylideneacetic acid p-nitrobenzyl ester in 1 l of absolute toluene and the mixture is stirred for 24 hours at 90° under nitrogen. The solvent is evaporated off in vacuo and the residue is chromatographed over 100 g of silica gel with toluene/ethyl acetate (3:2). The title compound is obtained in the form of yellowish crystals having the following physico-chemical properties:

Melting point: 160°-161° (diethyl ether/methylene chloride); TLC: $R_f=0.21$ (toluene/ethyl acetate 2:3); UV spectrum (in ethanol): $\lambda_{max}=333$ nm ($\epsilon=6678$); 259 nm ($\epsilon=15526$); IR spectrum (CH$_2$Cl$_2$): absorption bands at 5.55, 5.78, 6.55, 7.4, 7.6, 8.35 and 8.5μ; NMR spectrum (in CDCl$_3$/100 Mc, in ppm): 8.7-8.6, 2H, m; 8.16, 2H, m; 7.78, 1H, m; 7.5-7.25, 3H, m; 5.84, 1H, m; 5.24, 2H, m; 4.04-3.5, 2H, m.

EXAMPLE 111

(5R,S)-2-Pyrid-3-yl-2-penem-3-carboxylic acid 2 ml of water and 100 mg of 10% palladium/carbon catalyst are added to a solution of 50 mg (0.13 mmol) of (5R, S)-2-pyrid-3-yl-2-penem-3-carboxylic acid p-nitrobenzyl ester in 3 ml of absolute ethyl acetate and the mixture is stirred at normal pressure for 50 minutes under hydrogen. The hydrogenated mixture is filtered off from the catalyst over diatomaceous earth and the filtrate is washed with water, ethyl acetate and again with water. The combined aqueous phases are subjected to freeze-drying. The title compound obtained has the following physico-chemical properties:

UV spectrum (in ethanol): $\lambda_{max}=316$ nm; IR spectrum (KBr): absorption bands at 7.9, 1H, m; 7.6, 1H, m; 2.95, 5.65, 6.2 and 7.3μ.

EXAMPLE 112

In an analogous manner and using suitable intermediate products, optionally with the release of functional groups, the following compounds may be obtained:

(5R,S)-2-Methyl-2-penem-4-carboxylic acid tert.-butyl ester;

TLC: $R_f=0.63$ (toluene/ethyl acetate 1:1); IR spectrum (CH$_2$Cl$_2$): absorption bands at 3.9, 5.6, 5.85, 6.25, 7.3, 7.55 and 8.65μ.

(5R,S)-2-ethyl-2-penem-3-carboxylic acid;
(5R,S)-2-isopropyl-2-penem-3-carboxylic acid;
(5R,S)-2-hydroxymethyl-2-penem-4-carboxylic acid;
(5R,S)-2-acetoxyethyl-2-penem-3-carboxylic acid; and
(5R,S)-2-hydroxyethyl-2-penem-3-carboxylic acid,
as well as the corresponding (5R)- and (5S)-compounds; and their salts.

EXAMPLE 113

Dry ampoules or vials, containing 0.5 g of the sodium salt of (5R,S)-2-methyl-2-penem-3-carboxylic acid, are produced as follows:

Composition (for 1 ampoule or vial)

Sodium salt of (5R,S)-2-methyl-2-penem-3-carboxylic acid: 0.5 g
Mannitol: 0.05 g A sterile aqueous solution of the sodium salt of (5R,S)-2-methyl-2-penem-3-carboxylic acid and of the mannitol is subjected to freeze-drying under aseptic conditions in 5 ml ampoules or 5 ml vials and the ampoules or vials are sealed and examined.

EXAMPLE 114

Capsules, containing 0.25 g of (5R,S)-2-methyl-2-penem-3-carboxylic acid, are produced as follows:

Composition (for 1000 capsules)

(5R,S)-2-methyl-2-penem-3-carboxylic acid: 250,000 g
corn starch: 50,000 g
polyvinylpyrrolidone: 15,000 g
magnesium stearate: 5,000 g
ethanol: q.s.

The (5R,S)-2-methyl-2-penem-3-carboxylic acid and the corn starch are mixed and moistened with a solution of the polyvinylpyrrolidone in 50 g of ethanol. The moist composition is pressed through a sieve having a mesh width of 3 mm and dried at 45°. The dry granulate is forced through a sieve having a mesh width of 1 mm and mixed with 5 g of magnesium stearate. The mixture is introduced into push-fit capsules, size 0, in portions of 0.320 g.

What is claimed is:

1. Compounds of the formula

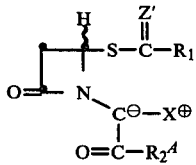

(II)

in which Z' represents oxygen, sulphur or a methylidene group optionally carrying one or two substituents selected from the group consisting of lower alkyl, cycloalkyl, cycloalkyl-lower alkyl, phenyl, phenyl-lower alkyl, lower alkoxycarbonyl, carbamoyl or cyano, $R_1$ represents hydrogen, lower alkyl, lower alkyl monosubstituted by hydroxy, lower alkoxy, lower alkanoyloxy, halogen, lower alkylthio, carboxyl, lower alkoxy-carbonyl, carbamoyl, cyano, nitro, amino, mono- or di-lower alkylamino, lower alkylene-amino or amino acylated by benzyloxycarbonyl, p-nitrobenzyloxycarbonyl or phenoxyacetyl; lower alkoxycarbonyl; aryl-lower alkoxycarbonyl; aryloxycarbonyl; aminocarbonyl; mono- or di-lower alkylaminocarbonyl; cycloalkyl, cycloalkyl-lower alkyl; phenyl; naphthyl; phenyl-lower alkyl; phenyl or phenyl-lower alkyl mono-substituted by lower alkyl, lower alkoxy, halogen, nitro or amino; pyridyl; thienyl; furyl; pyridyl-lower alkyl; thienyl-lower alkyl; furyl-lower alkyl; lower alkylthio; lower alkenylthio; cycloalkylthio; cycloalkyl-lower alkylthio; phenylthio; phenyl-lower alkylthio; or lower alkylthio, lower alkenylthio, cycloalkylthio, cycloalkyl-lower alkylthio, phenylthio or phenyl-lower alkylthio mono-substituted by hydroxy, lower alkoxy, lower alkanoyloxy, halogen, mercapto, lower alkylthio, carboxyl, lower alkoxycarbonyl, carbamoyl, cyano, nitro, amino, mono- or di-lower alkylamino, lower alkanoylamino or lower alkyleneamino, $X^{\oplus}$ represents triarylphosphonio, tri-lower alkylphosphonio or a phosphono group esterified twice by lower alkyl together with an alkali metal cation, and $R_2^A$ represents lower alkoxy, lower alkenyloxy, 2-halo-lower alkoxy, 2-lower alkylsulphonyl-lower alkoxy, 1-phenyl-lower alkoxy; 1-phenyl-lower alkoxy monosubstituted or disubstituted by lower alkoxy or nitro; pentachlorophenoxy, acetonyloxy, 2-cyanoethoxy, 2-tri-lower alkylsilylethoxy, 2-triphenylsilylethoxy or tri-lower alkylsilyloxy, in racemic or optically active form.

2. A compound having the formula

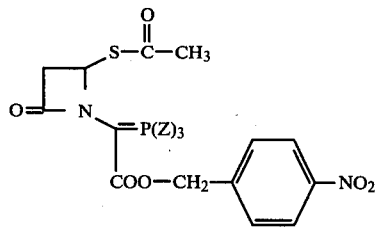

wherein Z is phenyl or lower alkyl.

3. The compound of claim 2, wherein Z is phenyl.

* * * * *